United States Patent
Notsuka et al.

(10) Patent No.: US 12,402,532 B2
(45) Date of Patent: Aug. 26, 2025

(54) LIGHT-EMITTING MATERIAL, COMPOUND, LONG-PERSISTENT PHOSPHOR AND LIGHT-EMITTING ELEMENT

(71) Applicant: KYULUX, INC., Fukuoka (JP)

(72) Inventors: Naoto Notsuka, Fukuoka (JP); Yuseok Yang, Fukuoka (JP); Asuka Yoshizaki, Fukuoka (JP)

(73) Assignee: KYULUX, INC., Fukuoka (JP)

( * ) Notice: Subject to any disclaimer, the term of this patent is extended or adjusted under 35 U.S.C. 154(b) by 0 days.

(21) Appl. No.: 18/475,451

(22) Filed: Sep. 27, 2023

(65) Prior Publication Data
US 2024/0032422 A1 Jan. 25, 2024

Related U.S. Application Data

(62) Division of application No. 16/627,101, filed as application No. PCT/JP2018/024302 on Jun. 27, 2018, now Pat. No. 11,832,516.

(30) Foreign Application Priority Data

Jun. 27, 2017 (JP) .................. 2017-124947
Jun. 15, 2018 (JP) .................. 2018-114758

(51) Int. Cl.
*C07C 255/42* (2006.01)
*C07C 255/52* (2006.01)
(Continued)

(52) U.S. Cl.
CPC ....... *H10K 85/6572* (2023.02); *C07C 255/42* (2013.01); *C07D 209/86* (2013.01);
(Continued)

(58) Field of Classification Search
CPC ............ H10K 85/6572; H10K 85/631; H10K 85/6574; C09K 2211/1029
See application file for complete search history.

(56) References Cited

U.S. PATENT DOCUMENTS

| 5,770,617 A | 6/1998 | Lavoie |
| 10,381,573 B2 | 8/2019 | Adachi et al. |

(Continued)

FOREIGN PATENT DOCUMENTS

| CN | 105209434 A | 12/2015 |
| CN | 106029829 A | 10/2016 |

(Continued)

OTHER PUBLICATIONS

WO-2015080183-A1—translation (Year: 2015).*
(Continued)

*Primary Examiner* — Jennifer A Boyd
*Assistant Examiner* — Rachel Simbana
(74) *Attorney, Agent, or Firm* — FISHERBROYLES, LLP; Roger L. Browdy

(57) ABSTRACT

A compound represented by the following general formula is an excellent light-emitting material. $R^1$ to $R^5$ each independently represent a hydrogen atom or a substituent, and one of $R^1$ to $R^5$ is a cyano group, one to three of $R^1$ to $R^5$ each are an aryl group Ar optionally substituted with an alkyl (Continued)

group or an aryl group, and one to three of $R^1$ to $R^5$ each are a donor group D (but excepting one that corresponds to Ar).

3 Claims, 3 Drawing Sheets

(51) Int. Cl.
  *C07C 255/58* (2006.01)
  *C07D 209/86* (2006.01)
  *C07D 209/88* (2006.01)
  *C07D 405/14* (2006.01)
  *C09K 11/06* (2006.01)
  *H10K 50/11* (2023.01)
  *H10K 50/12* (2023.01)
  *H10K 85/60* (2023.01)
  *H10K 101/10* (2023.01)
  *H10K 101/20* (2023.01)

(52) U.S. Cl.
  CPC ............ *C07D 405/14* (2013.01); *C09K 11/06* (2013.01); *H10K 85/626* (2023.02); *H10K 85/631* (2023.02); *H10K 85/6574* (2023.02); *C09K 2211/1007* (2013.01); *C09K 2211/1014* (2013.01); *C09K 2211/1018* (2013.01); *C09K 2211/1029* (2013.01); *H10K 50/11* (2023.02)

(56) References Cited

U.S. PATENT DOCUMENTS

| | | | |
|---|---|---|---|
| 2015/0105564 A1* | 4/2015 | Adachi | C07D 209/08 548/440 |
| 2016/0046563 A1* | 2/2016 | Stoessel | C07D 209/86 548/440 |
| 2016/0072076 A1* | 3/2016 | Stoessel | C07D 279/26 548/440 |
| 2016/0172599 A1 | 6/2016 | Ogiwara et al. | |
| 2016/0211466 A1 | 7/2016 | Ogiwara et al. | |
| 2016/0380205 A1 | 12/2016 | Adachi | |
| 2017/0098780 A1 | 4/2017 | Kim et al. | |
| 2018/0016493 A1 | 1/2018 | Lygaitis et al. | |
| 2019/0296246 A1 | 9/2019 | Hayano et al. | |

FOREIGN PATENT DOCUMENTS

| | | | |
|---|---|---|---|
| EP | 2039737 A2 | 3/2009 | |
| EP | 3015457 A1 | 5/2016 | |
| EP | 3 093 326 A1 | 11/2016 | |
| EP | 3 112 439 A1 | 1/2017 | |
| JP | 2009-94486 A | 4/2009 | |
| JP | 2011176250 A | 9/2011 | |
| JP | 2016-516085 A | 6/2016 | |
| KR | 10-2016-0126792 | 11/2016 | |
| KR | 2017035376 A * | 3/2017 | |
| KR | 10-2018-0001290 | 1/2018 | |
| KR | 2015-0132872 A | 3/2021 | |
| KR | 2016-0023655 A | 8/2021 | |
| WO | 2014/146752 A1 | 9/2014 | |
| WO | 2014/208698 A1 | 12/2014 | |
| WO | 2015/060352 A1 | 4/2015 | |
| WO | WO-2015080183 A1 * | 6/2015 | ........... C07C 211/61 |
| WO | 2015/159706 A1 | 10/2015 | |
| WO | 2015/199303 A1 | 12/2015 | |
| WO | 2016-010380 A1 | 1/2016 | |
| WO | 2016-105525 A2 | 6/2016 | |
| WO | 2016124704 A1 | 8/2016 | |
| WO | 2016181772 A1 | 11/2016 | |
| WO | 2016208240 A1 | 12/2016 | |

OTHER PUBLICATIONS

KR-2017035376-A—translation (Year: 2017).*
Notice of Final Rejection dated Dec. 19, 2023 issued in the corresponding Korean patent application No. 10-2020-700317 with its English Machine Translation.
Hansch, et al., A Survey of Hammett Substituent Constants and Resonance and Field Parameters, Chem. Rev., 1991, pp. 165-195, vol. 91.
Masui, et al., Analysis of exciton annihilation in high-efficiency sky-blue organic light-emitting diodes with thermally activated delayed fluorescence, Organic Electronics, 2013, pp. 2721-2726, vol. 14.
International Preliminary Report on Patentability dated Dec. 31, 2019 in PCT/JP2018/024302.
International Search Report dated Sep. 11, 2018, in PCT/JP2018/024302.
Extended European Search Report dated May 6, 2020 issued in the corresponding European patent application No. 18824986.6.
Chen X-H, et al., Synthes[s anit tsropertles of 1-(4-Aminophenyl)-2,4-dicyano-3-diethylamino-9,g-diethytfluorenes: Potential Fluorescent Material, 37(6):570-571Chemistry Letters (2008).
Japanese Office Action dated Apr. 12, 2022 issued in corresponding Japanese patent application No. 2018-114758 with its English Machine Translation.
Communication of a notice of opposition dated Jun. 10, 2022 issued in the corresponding European patent No. 3647392.
Submission form for publications, etc. dated Jun. 23, 2022 issued in the corresponding Japanese patent application No. 2018-114758 with partial Englsih Machine Translation.
Notice of fact for providing information_1 dated Aug. 8, 2022 issued in the corresponding Korean patent application No. 10-2020-700317 with its English Machine Translation.
Notice of fact for providing information_2 dated Aug. 8, 2022 issued in the corresponding Korean patent application No. 10-2020-700317 with its English Machine Translation.
Office Action dated Aug. 9, 2022 issued in the corresponding Japanese patent application No. 2018-114758 with its English Machine Translation.
Office Action dated Sep. 27, 2022 issued in the corresponding Chinese patent application No. 201880042612.3 with its English Machine Translation.
Office Action dated Mar. 22, 2023 issued in the corresponding Chinese patent application No. 201880042612.3 with its English Machine Translation.
Office Action dated Jun. 22, 2023 issued in the corresponding Korean patent application No. 10-2020-700317 with its English Machine Translation.
Summons to attend oral proceedings dated Jul. 13, 2023 issued in the corresponding European patent application No. 18824986.6.
Rafik Omar-Amrani et al., "Novel Synthetic Strategy of N-Arylated Heterocycles via Sequential Palladium-Catalyzed Intra- and Inter-Arylamination Reactions", Synthesis, 2004, No. 15, pp. 2527-2534.
Makoto Fujita et al., "Palladium(0)ILiCl Promoted Cross-Coupling Reaction of (4-Pyridyl) stannanes and Aromatic Bromides: Easy Access to Poly(4-pyridyl)-Substituted Aromatics", Tetrahedron letters, 1995, vol. 36, No. 29, pp. 5247-5250.
John R. Nabera, "Palladium-Catalyzed Stille Cross-CouplingReaction of Aryl Chlorides usinga Pre-Milled Palladium Acetate and XPhos Catalyst System", Adv. Synth. Catal., 2008, 350, pp. 957-961.
Interlocutory decision in Opposition proceedings dated Jan. 10, 2025 issued in the corresponding European patent No. 3647392.

* cited by examiner

LIGHT-EMITTING MATERIAL, COMPOUND, LONG-PERSISTENT PHOSPHOR AND LIGHT-EMITTING ELEMENT

TECHNICAL FIELD

The present invention relates to a compound useful as a light-emitting material and to a light-emitting device using the compound. The invention also relates to a delayed fluorescent material that emits delayed fluorescence.

BACKGROUND ART

Studies for enhancing the light emission efficiency of organic light-emitting devices such as organic electroluminescent devices (organic EL devices) are being made actively. In particular, various kinds of efforts have been made for increasing light emission efficiency by newly developing and combining an electron transfer material, a hole transfer material, a light-emitting material and others to constitute an organic electroluminescent device. Among them, there is known a study relating to an organic electroluminescent device that utilizes a delayed fluorescent material.

A delayed fluorescent material is a compound which, in an excited state, after having undergone reverse intersystem crossing from an excited triplet state to an excited singlet state, emits fluorescence when returning back from the excited singlet state to a ground state thereof. Fluorescence through the route is observed later than fluorescence from the excited singlet state directly occurring from the ground state (ordinary fluorescence), and is therefore referred to as delayed fluorescence. Here, for example, in the case where a light-emitting compound is excited through carrier injection thereinto, the occurring probability of the excited singlet state to the excited triplet state is statistically 25%/75%, and therefore improvement of light emission efficiency by the fluorescence alone from the directly occurring excited singlet state is limited. On the other hand, in a delayed fluorescent material, not only the excited singlet state thereof but also the excited triplet state can be utilized for fluorescent emission through the route via the above-mentioned reverse intersystem crossing, and therefore as compared with an ordinary fluorescent material, a delayed fluorescent material can realize a higher emission efficiency.

After such principles have been revealed, various delayed fluorescent materials have been invented by various studies. However, any and all materials capable of emitting delayed fluorescence could not be directly said to be useful as a light-emitting material. Among delayed fluorescent materials, some could relatively hardly undergo reverse intersystem crossing, and some others may have a long delayed fluorescence lifetime. Further, still some others may suffer from emission efficiency reduction owing to accumulation of excitons in a high-current density region, and may therefore rapidly degrade in continuous long-term driving. Accordingly, in fact, most delayed fluorescent materials are still desired to be further improved in point of practical use thereof. Consequently, even cyanobenzene derivatives known as a delayed fluorescent material are pointed out to have problems to be solved. For example, 2CzPN having the following structure is a material that emits delayed fluorescence, but has a problem in that its emission efficiency is not high and the emission efficiency thereof in a high-current density region is great (see NPL 1).

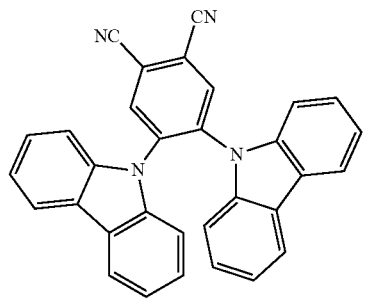 [SMILES: N#Cc1cc(-n2c3ccccc3c3ccccc32)c(-n2c3ccccc3c3ccccc32)cc1C#N]

CITATION LIST

Non-Patent Literature

NPL 1: Organic Electronics 14 (2013)2721-2726

SUMMARY OF INVENTION

Technical Problem

Though delayed fluorescent materials are pointed out to have such problems, the relation between chemical structures of delayed fluorescent materials and properties thereof could not be said to have been sufficiently clarified. Consequently, at present, it is difficult to generalize the chemical structure of a compound useful as a light emitting material, and there are many unclear points.

Given the situation, the present inventors have made assiduous studies for the purpose of providing a compound more useful as a light-emitting material for light-emitting devices. With that, the present inventors have further made assiduous studies for the purpose of deriving a general formula of a compound more useful as a light-emitting material and generalizing such a compound.

Solution to Problem

As a result of assiduous studies made for the purpose of attaining the above-mentioned object, the present inventors have found that a compound a dicyanobenzene derivative substituted with a donor group and further substituted with a specific aryl group is useful as a material for light-emitting devices. The present invention has been proposed on the basis of such findings, and specifically has the following constitution.

[1] A light-emitting material containing a compound represented by the following general formula (1):

General Formula (1)

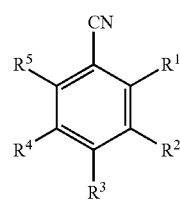

In the general formula (1), $R^1$ to $R^5$ each independently represent a hydrogen atom or a substituent;

one of $R^1$ to $R^5$ is a cyano group,
one to three of $R^1$ to $R^5$ each are an aryl group Ar optionally substituted with an alkyl group or an aryl group (in which the benzene ring to constitute the aryl group Ar may be condensed with a ring that may optionally contain an oxygen atom or a sulfur atom in addition to carbon atoms as a ring skeleton-constituting atom, but is not condensed with a ring containing any other hetero atom than an oxygen atom and a sulfur atom as a ring skeleton-constituting atom), and when two or more of $R^1$ to $R^5$ are Ar's, these Ar's may be the same as or different from each other,
one to three of $R^1$ to $R^5$ each are a donor group D (but excepting one that corresponds to Ar), and when two or more of $R^1$ to $R^5$ are D's, these D's may be the same as or different from each other.

[2] The light-emitting material according to [11], wherein $R^1$ to $R^5$ each independently represent a cyano group, Ar or D.

[3] The light-emitting material according to [1] or [2], wherein D contains a substituted amino group.

[4] The light-emitting material according to [3], wherein D is a group represented by the following general formula (2a):

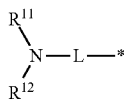

General Formula (2a)

In the general formula (2a), $R^{11}$ and $R^{12}$ each independently represent a substituted or unsubstituted alkyl group, a substituted or unsubstituted alkenyl group, a substituted or unsubstituted aryl group, or a substituted or unsubstituted heteroaryl group; L represents a single bond, a substituted or unsubstituted arylene group, or a substituted or unsubstituted heteroarylene group; * indicates a bonding position to the carbon atom (C) constituting a ring skeleton of the benzene ring in the general formula (1); and $R^{11}$ and $R^{12}$ may bond to each other to form a cyclic structure.

[5] The light-emitting material according to [3], wherein D is a group represented by the following general formula (2b):

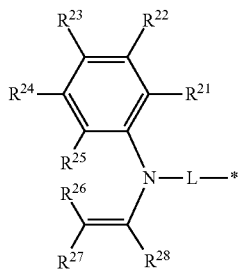

General Formula (2b)

In the general formula (2b), $R^{21}$ to $R^{28}$ each independently represent a hydrogen atom or a substituent; L represents a single bond, a substituted or unsubstituted arylene group, or a substituted or unsubstituted heteroarylene group; $R^{21}$ and $R^{22}$, $R^{22}$ and $R^{23}$, $R^{23}$ and $R^{24}$, $R^{24}$ and $R^{25}$, $R^{26}$ and $R^{27}$, and $R^{27}$ and $R^{28}$ each may bond to each other to form a linking group necessary for forming a cyclic structure; and $R^{25}$ and $R^{26}$ may bond to each other to form a single bond or a linking group.

[6] The light-emitting material according to [3], wherein D is a group represented by the following general formula (2c):

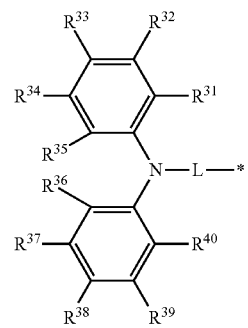

General Formula (2c)

In the general formula (2c), $R^{31}$ to $R^{40}$ each independently represent a hydrogen atom or a substituent; L represents a single bond, a substituted or unsubstituted arylene group, or a substituted or unsubstituted heteroarylene group; $R^{31}$ and $R^{32}$, $R^{32}$ and $R^{33}$, $R^{33}$ and $R^{34}$, $R^{34}$ and $R^{35}$, $R^{36}$ and $R^{37}$, $R^{37}$ and $R^{38}$, $R^{38}$ and $R^{39}$, and $R^{39}$ and $R^{40}$ each may bond to each other to form a linking group necessary for forming a cyclic structure; and $R^{35}$ and $R^{36}$ may bond to each other to form a single bond or a linking group; and * indicates a bonding position to the carbon atom (C) constituting the ring skeleton of the benzene ring in the general formula (1).

[7] The light-emitting material according to any one of [4] to [6], wherein L is a single bond.

[8] The light-emitting material according to any one of [4] to [6], wherein $R^3$ is a cyano group, and L is a substituted or unsubstituted phenylene group.

[9] The light-emitting material according to any one of [4] to [8], wherein D is a group represented by any of the following general formulae (3) to (6):

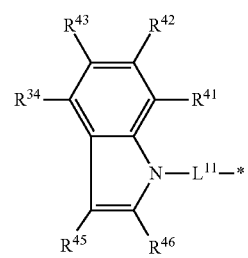

General Formula (3)

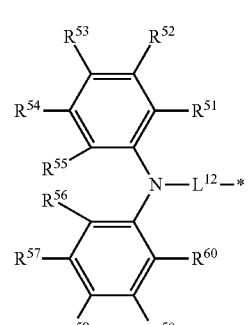

General Formula (4)

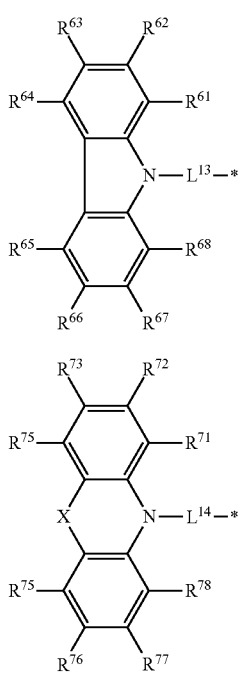

General Formula (5)

General Formula (6)

In the general formulae (3) to (6), $R^{41}$ to $R^{46}$, $R^{51}$ to $R^{60}$, $R^{61}$ to $R^{68}$, and $R^{71}$ to $R^{78}$ each independently represent a hydrogen atom or a substituent; $L^{11}$ to $L^{14}$ each independently represent a single bond, a substituted or unsubstituted arylene group, or a substituted or unsubstituted heteroarylene group. In the general formula (6), X represents an oxygen atom, a sulfur atom, a substituted or unsubstituted nitrogen atom, a substituted or unsubstituted carbon atom, a substituted or unsubstituted silicon atom or a carbonyl group, which is divalent and which has a linking chain length of one atom, or represents a substituted or unsubstituted ethylene group, a substituted or unsubstituted vinylene group, a substituted or unsubstituted o-arylene group or a substituted or unsubstituted o-heteroarylene group, which is divalent and which has a bonding chain length of two atoms.

[10] A compound represented by the general formula (1).
[11] A delayed fluorescent material containing a compound represented by the general formula (1).
[12] A light-emitting device containing a compound represented by the general formula (1).
[13] The light-emitting device according to [12], which emits delayed fluorescence.
[14] The light-emitting device according to [12] or [13], wherein the light-emitting device has a light-emitting layer and the light-emitting layer contains the compound and a host material.
[15] The light-emitting device according to any one of [12] to [14], wherein the light-emitting device has a light-emitting layer and the light-emitting layer contains the compound and a light-emitting material.

Advantageous Effects of Invention

The compound of the present invention is useful as a light-emitting material. The compound of the present invention includes compounds capable of emitting delayed fluorescence and capable of effectively utilizing the excited triplet energy thereof for light emission. Accordingly, an organic light-emitting device using the compound of the present invention as a light-emitting material therein can realize high emission efficiency.

DESCRIPTION OF EMBODIMENTS

Figure 1:
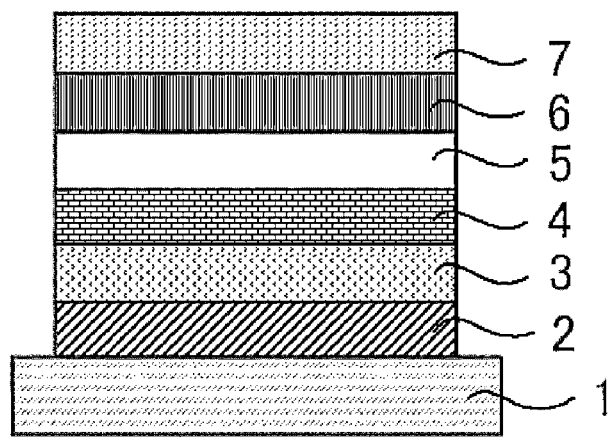
FIG. 1 This is a schematic cross-sectional view showing a layer configuration example of an organic electroluminescent device.

The contents of the invention will be described in detail below. The constitutional elements may be described below with reference to representative embodiments and specific examples of the invention, but the invention is not limited to the embodiments and the examples. In the description herein, a numerical range expressed as "to" means a range that includes the upper limit and/or the lower limit. In the invention, the hydrogen atom that is present in the compound used in the invention is not particularly limited in isotope species, and for example, all the hydrogen atoms in the molecule may be $^1H$, and all or a part of them may be $^2H$ (deuterium (D)). The matters described in Japanese Patent Application 2018-114758, especially Tables 1 to 5 in the specification of the patent application are incorporated herein by reference.

[Compound Represented by General Formula (1)]

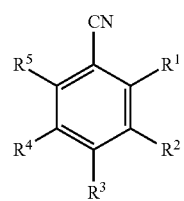

General Formula (1)

In the general formula (1), $R^1$ to $R^5$ each represent a hydrogen atom or a substituent.

One alone of $R^1$ to $R^5$ is a cyano group. The substituent that represents a cyano group may be $R^1$, or $R^2$, or $R^3$.

One to three of $R^1$ to $R^5$ in the general formula (1) each are an aryl group Ar optionally substituted with an alkyl group or an aryl group. Among $R^1$ to $R^5$, the number of the substituents each representing an aryl group Ar may be one to three, but is preferably one or two. The benzene ring that has a bond of Ar may be a single ring or a part of a condensed ring. In the case where a ring is further condensed with a benzene ring, the condensed ring may be a ring composed of carbon atoms alone as the ring skeleton-constituting atoms, or may contain an oxygen atom or a sulfur atom as a ring skeleton-constituting atom. However, in the case where a ring is further condensed with a benzene ring, the condensed ring is not a ring that contains any other hetero atom than an oxygen atom and a sulfur atom as a ring skeleton-constituting atom. Examples of the ring that may be condensed with a benzene ring having a bond of Ar include a benzene ring, a furan ring, a thiophene ring, a cyclopentene ring, a cyclopentadiene ring, a cyclohexene ring, a cyclohexadiene ring, a cycloheptene ring, a cycloheptadiene ring, and a cycloheptatriene ring. The benzene ring having a bond of Ar may be condensed with one ring, or may be condensed with two or more rings. A ring may be further condensed with the ring condensed with the benzene ring having a bond of Ar. Even in such a case where multiple rings are condensed, the resultant condensed ring is a ring where ring skeleton-constituting atoms are carbon atoms alone or is a ring that contains an oxygen atom or a sulfur atom as a ring skeleton-constituting atom. In the case where two or more rings are condensed, these two or more rings may be the same as or different from each other.

The benzene ring having a bond of Ar or the condensed ring containing the benzene ring as a part thereof may be substituted with at least one substituent of an alkyl group and an aryl group. The substituent as referred to herein means a monovalent group capable of substituting for a hydrogen atom, and is not a concept to include condensation.

The "alkyl group" to be a substituent as referred to herein may be any of a linear, branched or cyclic one. The group may have two or more kinds of a linear moiety, a cyclic moiety and a branched moiety as combined. The carbon number of the alkyl group may be, for example, 1 or more, 2 or more, or 4 or more. The carbon number may be 30 or less, 20 or less, 10 or less, 6 or less, or 4 or less. Specific examples of the alkyl group include a methyl group, an ethyl group, an n-propyl group, an isopropyl group, an n-butyl group, an isobutyl group, a tert-butyl group, an n-pentyl group, an isopentyl group, an n-hexyl group, an isohexyl group, a 2-ethylhexyl group, an n-heptyl group, an isoheptyl group, an n-octyl group, an isooctyl group, an n-nonyl group, an isononyl group, an n-decanyl group, an isodecanyl group, a cyclopentyl group, a cyclohexyl group, and a cycloheptyl group. The alkyl group to be a substituent may be further substituted with an aryl group.

The "aryl group" to be a substituent as referred to herein may be a group composed of one aromatic hydrocarbon ring alone, or may be a group of an aromatic hydrocarbon ring further condensed with one or more rings. The group of an aromatic hydrocarbon ring further condensed with one or more rings for use herein may be a group of an aromatic hydrocarbon ring further condensed with one or more of an aromatic hydrocarbon ring, an aliphatic hydrocarbon ring and a non-aromatic heterocyclic ring. The carbon number of the aryl group may be, for example, 6 or more, or 10 or more. The carbon number may be 30 or less, 18 or less, 14 or less, or 10 or less. Specific examples of the aryl group include a phenyl group, a 1-naphthyl group, a 2-naphthyl group, a 1-anthracenyl group, a 2-anthracenyl group, and a 9-anthracenyl group. The aryl group to be a substituent may be further substituted with an alkyl group and an aryl group.

In the case where the benzene ring having a bond of Ar has a substituent, the substitution position of the substituent is preferably any of 3- to 5-positions. For example, preferred examples include a case having a substituent at the 3-position, a case having a substituent at the 4-position, a case having a substituent at the 3-position and the 5-position, and a case having a substituent at the 3-position, the 4-position and the 5-position.

The total carbon number of the group represented by Ar is preferably 6 to 50, more preferably 6 to 30, even more preferably 6 to 18, and further more preferably 6 to 12.

A preferred group of Ar includes a phenyl group, a phenyl group substituted with an alkyl group, a phenyl group substituted with a phenyl group, a phenyl group substituted with an alkyl group and a phenyl group, a naphthyl group, a naphthyl group substituted with an alkyl group, a naphthyl group substituted with a phenyl group, a naphthyl group substituted with an alkyl group and a phenyl group, a dibenzofuryl group, a dibenzofuryl group substituted with an alkyl group, a dibenzofuryl group substituted with an alkyl group and a phenyl group, a dibenzothiophenyl group, a dibenzothiophenyl group substituted with an alkyl group, a dibenzothiophenyl group substituted with an alkyl group and a phenyl group, a fluorenyl group, a fluorenyl group substituted with an alkyl group, a fluorenyl group substituted with a phenyl group, and a fluorenyl group substituted with an alkyl group and a phenyl group. Another preferred group of Ar includes a phenyl group, a monoalkylphenyl group, a dialkylphenyl group, a trialkylphenyl group, a tetraalkylphenyl group, a pentaalkylphenyl group, a monophenylphenyl group, a diphenylphenyl group, a naphthyl group, a monoalkylnaphthyl group, a dialkylnaphthyl group, a trialkylnaphthyl group, a tetraalkylnaphthyl group, a pentaalkylnaphthyl group, a monophenylnaphthyl group, a dibenzofuryl group, a monoalkyldibenzofuryl group, a dialkyldibenzofuryl group, trialkyldibenzofuryl group, a tetraalkyldibenzofuryl group, a pentaalkyldibenzofuryl group, a monophenyldibenzofuryl group, a dibenzothiophenyl group, a monoalkyldibenzothiophenyl group, a dialkyldibenzothiophenyl group, a trialkyldibenzothiophenyl group, a tetraalkyldibenzothiophenyl group, a pentaalkyldibenzothiophenyl group, a monophenylalkyldibenzothiophenyl group, a monoalkylfluorenyl group, a dialkylfluorenyl group, a trialkylfluorenyl group, a tetraalkylfluorenyl group, an octaalkylfluorenyl group, a monophenylfluorenyl group, a diphenylfluorenyl group, a triphenylfluorenyl group, and a tetraphenylfluorenyl group.

Specific examples of the group represented by Ar are mentioned below, but Ar that can be employed in the present invention should not be limitatively interpreted by these specific examples.

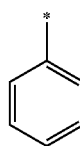

Ar 1

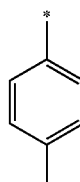

Ar 2

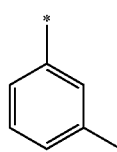

Ar 3

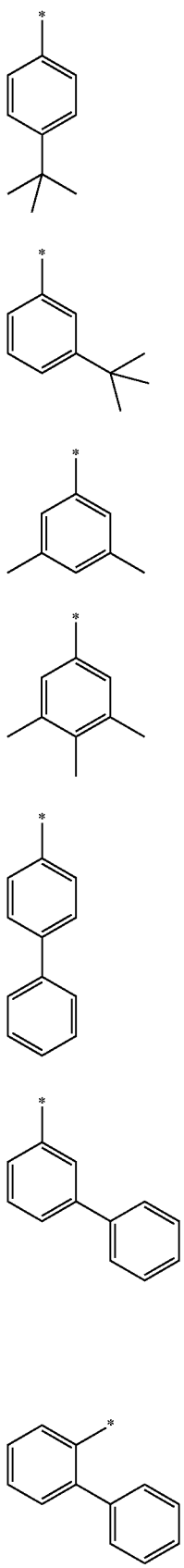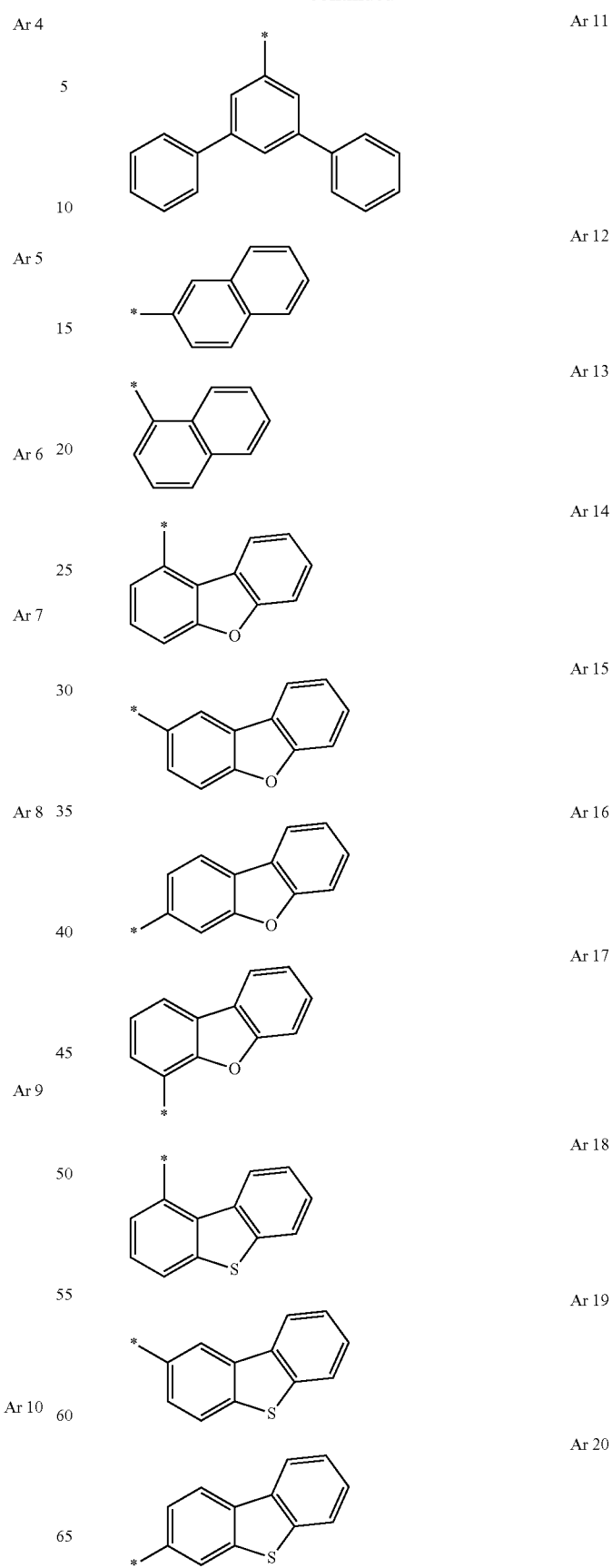

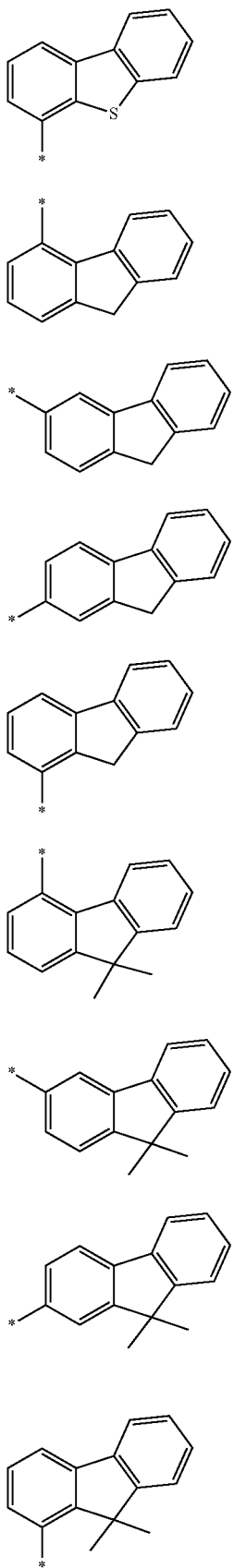
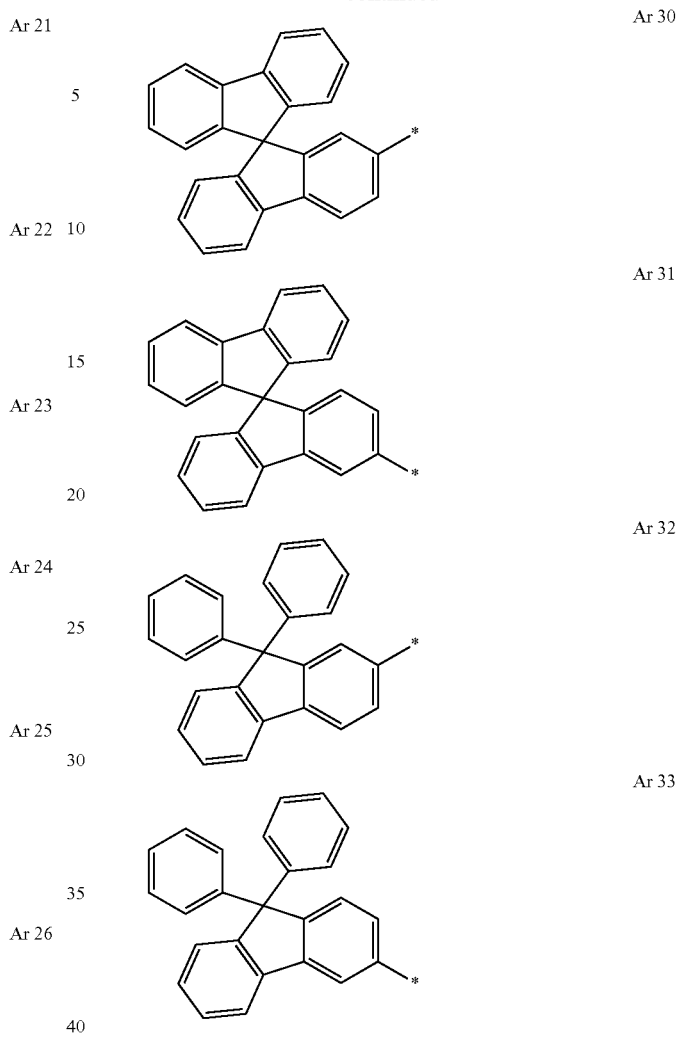

In the general formula (1), one to three of $R^1$ to $R^5$ each represent a donor group D. However, the donor group D does not include one that corresponds to Ar.

The "donor group" as referred to in this description is a group having a negative Hammett's $\sigma_P$ value. Here, "Hammett's $\sigma_P$ value" is one propounded by L. P. Hammett, and is one to quantify the influence of a substituent on the reaction rate or the equilibrium of a para-substituted benzene derivative. Specifically, the value is a constant (6p) peculiar to the substituent in the following equation that is established between a substituent and a reaction rate constant or an equilibrium constant in a para-substituted benzene derivative:

$$\log(k/k_0) = \rho \sigma_P$$

or $$\log(K/K_0) = \rho \sigma_P$$

In the above equations, k represents a rate constant of a benzene derivative not having a substituent; $k_0$ represents a rate constant of a benzene derivative substituted with a substituent; K represents an equilibrium constant of a benzene derivative not having a substituent; $K_0$ represents an equilibrium constant of a benzene derivative substituted with a substituent; $\rho$ represents a reaction constant to be determined by the kind and the condition of reaction. Regarding the description relating to the "Hammett's $\sigma_P$ value" and the numerical value of each substituent, reference may be made to the description relating to $\sigma_P$ value in Hansch, C. et. al., Chem. Rev., 91, 165-195 (1991). A group having a negative Hammett's $\sigma_P$ value tends to exhibit electron-donating performance (donor-like performance) and a group having a positive Hammett's $\sigma_P$ value tends to exhibit electron-accepting performance (acceptor-like performance).

In the general formula (1), D is preferably a group containing a substituted amino group. The substituent that bonds to the nitrogen atom of the amino group is preferably a substituted or unsubstituted alkyl group, a substituted or unsubstituted alkenyl group, a substituted or unsubstituted aryl group, or a substituted or unsubstituted heteroaryl group, and is more preferably a substituted or unsubstituted aryl group, or a substituted or unsubstituted heteroaryl group. In particular, the substituent is preferably a substituted or unsubstituted diarylamino group, or a substituted or unsubstituted diheteroarylamino group. In the general formula (1), D may be a group bonding at the nitrogen atom of a substituted amino group, or may also be a group bonding at a group to which a substituted amino group bonds. The group to which a substituted amino group bonds is preferably a π-conjugated group.

Here, for the "alkyl group" to be a substituent, reference may be made to the corresponding description of the alkyl group to be a substituent for Ar in the general formula (1).

Here, the "alkenyl group" to be a substituent may be any of a linear, branched or cyclic one. The group may have two or more kinds of a linear moiety, a cyclic moiety and a branched moiety as combined. The carbon number of the alkenyl group may be, for example, 2 or more, or 4 or more. The carbon number may be 30 or less, 20 or less, 10 or less, 6 or less, or 4 or less. Specific examples of the alkenyl group include an ethenyl group, an n-propenyl group, an isopropenyl group, an n-butenyl group, an isobutenyl group, an n-pentenyl group, an isopentenyl group, an n-hexenyl group, an isohexenyl group, and a 2-ethylhexenyl group. The alkenyl group to be a substituent may be further substituted with a substituent.

The "aryl group" and the "heteroaryl group" to substituents as referred to herein each may be a single ring or may be a condensed ring of two or more rings condensed with each other. In the case of a condensed ring, the number of condensed rings is preferably selected from 2 to 6, more preferably 2 to 4. Specific examples of the ring include a benzene ring, a pyridine ring, a pyrimidine ring, a triazine ring, a naphthalene ring, an anthracene ring, a phenanthrene ring, a triphenylene ring, a quinoline ring, a pyrazine ring, a quinoxaline ring, and a naphthyridine ring. Specific examples of the arylene group and the heteroarylene group include a phenyl group, a 1-naphthyl group, a 2-naphthyl group, a 1-anthracenyl group, a 2-anthracenyl group, a 9-anthracenyl group, a 2-pyridyl group, a 3-pyridyl group, and a 4-pyridyl group. The arylene group and the heteroarylene group each may have a substituent or may be unsubstituted. In the case where the group has 2 or more substituents, the multiple substituents may be the same as or different from each other. The substituent includes a hydroxy group, a halogen atom, an alkyl group having 1 to 20 carbon atoms, an alkoxy group having 1 to 20 carbon atoms, an alkylthio group having 1 to 20 carbon atoms, an alkyl-substituted amino group having 1 to 20 carbon atoms, an aryl-substituted amino group having 1 to 26 carbon atoms, an aryl group having 6 to 40 carbon atoms, a heteroaryl group having 3 to 40 carbon atoms, an alkenyl group having 2 to 10 carbon atoms, an alkynyl group having 2 to 10 carbon atoms, an alkylamide group having 2 to 20 carbon atoms, an arylamide group having 7 to 21 carbon atoms, and a trialkylsilyl group having 3 to 20 carbon atoms. Of these specific examples, those further substitutable with any substituent may be substituted. More preferred substituents include an alkyl group having 1 to 20 carbon atoms, an alkoxy group having 1 to 20 carbon atoms, an alkylthio group having 1 to 20 carbon atoms, an alkyl-substituted amino group having 1 to 26 carbon atoms, an aryl-substituted amino group having 1 to 20 carbon atoms, an aryl group having 6 to 40 carbon atoms, and a heteroaryl group having 3 to 40 carbon atoms.

The donor group D in the general formula (1) is, for example, preferably a group represented by the following general formula (2a).

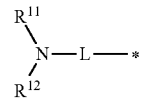

General Formula (2a)

In the general formula (2a), $R^{11}$ and $R^{12}$ each independently represent a substituted or unsubstituted alkyl group, a substituted or unsubstituted alkenyl group, a substituted or unsubstituted aryl group, or a substituted or unsubstituted heteroaryl group. $R^{11}$ and $R^{12}$ may bond to each other to form a cyclic structure. L represents a single bond, a substituted or unsubstituted arylene group, or a substituted or unsubstituted heteroarylene group. The substituent that may be introduced into the arylene group or the heteroarylene group of L may be a group represented by the general formula (1), or a group represented by any of the general formulae (2a), (2b), (2c), and (3) to (6) to be mentioned hereinunder. The groups represented by these (1) to (6) may be introduced into L up to the largest number of substituents that can be introduced thereinto. In the case where multiple groups of the general formulae (1) to (6) are introduced, these substituents may be the same as or different from each other. * indicates a bonding position to the carbon atom (C) constituting a ring skeleton of the benzene ring in the general formula (1).

In the general formula (2a), $R^{11}$ and $R^{12}$ may bond to each other to form a cyclic structure along with the nitrogen atom in the general formula (2a).

For the aryl group or the heteroaryl group represented by $R^{11}$ and $R^{12}$, reference may be made to the description of the aryl group or the heteroaryl group to be a substituent that bonds to the nitrogen atom of the amino group mentioned hereinabove.

The substituent represented by the general formula (2a) is preferably a substituent represented by the following general formula (2b).

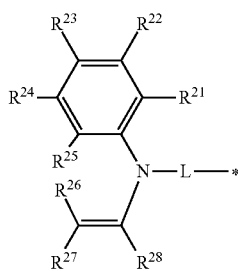

In the general formula (2b), $R^{21}$ to $R^{28}$ each independently represent a hydrogen atom or a substituent. L represents a single bond, a substituted or unsubstituted arylene group, or a substituted or unsubstituted heteroarylene group. $R^{21}$ and $R^{22}$, $R^{22}$ and $R^{23}$, $R^{23}$ and $R^{24}$, $R^{24}$ and $R^{25}$, $R^{26}$ and $R^{27}$, and $R^{27}$ and $R^{28}$ each may bond to each other to form a linking group necessary for forming a cyclic structure. $R^{25}$ and $R^{26}$ may bond to each other to form a single bond or a linking group. For example, when $R^{25}$ and $R^{26}$ bond to each other to form a single bond, the compound represented by the general formula (2b) includes a carbazole ring. * indicates a bonding position to the carbon atom (C) that constitutes the ring skeleton of the benzene ring in the general formula (1). Regarding specific examples and preferred range of the substituents that $R^{21}$ to $R^{28}$ may have, reference may be made to the description of the arylene group or the heteroarylene group to be a substituent for Ar in the general formula (1).

The cyclic structure to be formed by $R^{21}$ and $R^{22}$, $R^{22}$ and $R^{23}$, $R^{23}$ and $R^{24}$, $R^{24}$ and $R^{25}$, $R^{25}$ and $R^{26}$, $R^{26}$ and $R^{27}$, and $R^{27}$ and $R^{28}$ each bonding to each other may be an aromatic ring or an aliphatic ring, and may contain a hetero atom, and further, the cyclic structure may be a condensed ring of 2 or more rings. Here, the hetero atom is preferably one selected from the group consisting of a nitrogen atom, an oxygen atom and a sulfur atom. Examples of the cyclic structure to be formed include a benzene ring, a naphthalene ring, a pyridine ring, a pyridazine ring, a pyrimidine ring, a pyrazine ring, a pyrrole ring, an imidazole ring, a pyrazole ring, an imidazoline ring, an oxazole ring, an isoxazole ring, a thiazole ring, an isothiazole ring, a cyclohexadiene ring, a cyclohexene ring, a cyclopentaene ring, a cycloheptatriene ring, a cycloheptadiene ring, a cycloheptaene ring, a furan ring, a thiophene ring, a naphthyridine ring, a quinoxaline ring, and a quinoline ring.

The substituent represented by the general formula (2a) is preferably a substituent represented by the following general formula (2c).

General Formula (2c)

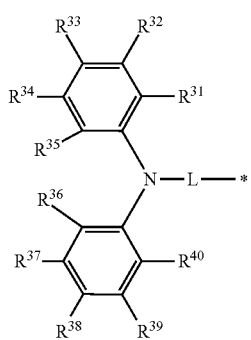

In the general formula (2c), $R^{31}$ to $R^{40}$ each independently represent a hydrogen atom or a substituent. L represents a single bond, a substituted or unsubstituted arylene group, or a substituted or unsubstituted heteroarylene group. $R^{31}$ and $R^{32}$, $R^{32}$ and $R^{33}$, $R^{33}$ and $R^{34}$, $R^{34}$ and $R^{35}$, $R^{36}$ and $R^{37}$, $R^{37}$ and $R^{38}$, $R^{38}$ and $R^{39}$, and $R^{39}$ and $R^{40}$ each may bond to each other to form a linking group necessary for forming a cyclic structure. $R^{35}$ and $R^{36}$ may bond to each other to form a single bond or a linking group. * indicates a bonding position to the carbon atom (C) constituting the ring skeleton of the benzene ring in the general formula (1). For specific examples and preferred ranges of the substituents that $R^{31}$ to $R^{40}$ may have, reference may be made to the description of the arylene group or the heteroarylene group to be a substituent for Ar in the general formula (1).

Regarding the cyclic structure to be formed by $R^{31}$ and $R^{32}$, $R^{32}$ and $R^{33}$, $R^{33}$ and $R^{34}$, $R^{34}$ and $R^{35}$, $R^{35}$ and $R^{36}$, $R^{36}$ and $R^{37}$, $R^{37}$ and $R^{38}$, $R^{38}$ and $R^{39}$, and $R^{39}$ and $R^{40}$ each bonding to each other, reference may be made to the corresponding description of the cyclic structure that $R^{21}$ and $R^{22}$ in the general formula (2a) form.

In the general formulae (2a) to (2c), L represents a single bond, a substituted or unsubstituted arylene group, or a substituted or unsubstituted heteroarylene group. Preferably, L is a single bond, or a substituted or unsubstituted arylene group.

The aromatic ring to constitute the arylene group represented by L may be a single ring or a condensed ring of two or more condensed aromatic rings. In the case of where two or more aromatic rings are condensed, they may link linearly or in a branched form. The carbon number of the aromatic ring to constitute the arylene group represented by L is preferably 6 to 22, more preferably 6 to 18, even more preferably 6 to 14, and further more preferably 6 to 10. Specific examples of the arylene group include a phenylene group, a naphthalenediyl group, and a biphenylene group.

The hetero ring to constitute the heteroarylene group represented by L may be a single ring, or a condensed ring of one or more hetero rings condensed with an aromatic ring or a hetero ring, or a linking ring of one or more hetero rings linking to an aromatic ring or a hetero ring. The carbon number of the hetero ring is preferably 5 to 22, more preferably 5 to 18, even more preferably 5 to 14, and further more preferably 5 to 10. Preferably, the hetero atom to constitute the hetero ring is a nitrogen atom. Specific examples of the hetero ring include a pyridine ring, a pyridazine ring, a pyrimidine ring, a triazole ring, and a benzotriazole ring.

A more preferred group represented by L is a phenylene group. When L is a phenylene group, the phenylene group may be any of a 1,2-phenylene group, a 1,3-phenylene group, or a 1,4-phenylene group, but is preferably a 1,4-phenylene group. L may be substituted with a substituent. The number of the substituents for L and the substitution position thereof are not specifically limited. Regarding the description and preferred ranges of the substituents that may be introduced into L, reference may be made to the description and the preferred ranges of the substituents that $R^{11}$ and $R^{12}$ mentioned above may have. The substituent that may be introduced into the arylene group or the heteroarylene group of L may be a group represented by any of the general formulae (1), (2a), (2b) and (2c), and may also be a group represented by any of the general formulae (3) to (6) to be mentioned hereinunder. The groups represented by these (1) to (6) may be introduced into L up to the largest number of substituents that can be introduced thereinto. In the case where multiple groups of the general formulae (1) to (6) are introduced, these substituents may be the same as or different from each other.

In the case where L has a substituent, the substituent may form a cyclic structure along with $R^{11}$ and $R^{12}$ in (2a), or $R^{21}$ and $R^{28}$ in (2b), or $R^{31}$ and $R^{40}$ in (2c).

The substituent represented by the general formulae (2a) to (2c) is preferably a substituent represented by any of the following general formulae (3) to (6). Above all, groups represented by the general formulae (3) to (5) are preferred, and groups represented by the general formula (5) are more preferred.

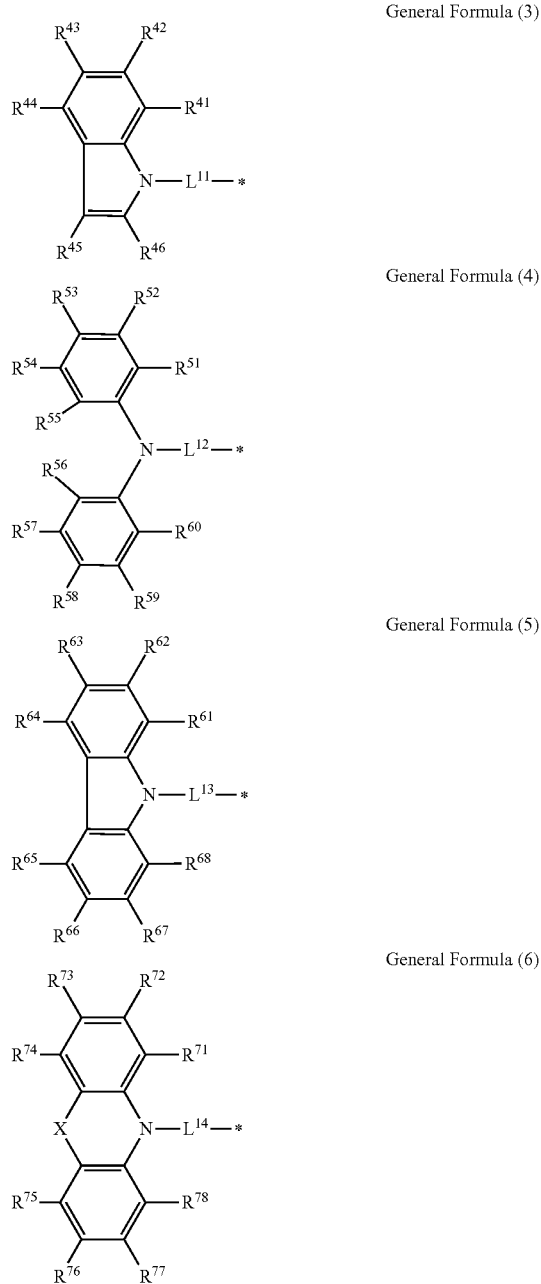

General Formula (3)

General Formula (4)

General Formula (5)

General Formula (6)

In the general formulae (3) to (6), $R^{41}$ to $R^{46}$, $R^{51}$ to $R^{60}$, $R^{61}$ to $R^{68}$, and $R^7$ to $R^{78}$ each independently represent a hydrogen atom or a substituent. Regarding the description and preferred ranges of the substituent as referred to herein, reference may be made to the description of the arylene group or the heteroarylene group of a substituent for Ar in the general formula (1). Preferably, $R^{41}$ to $R^{46}$, $R^{51}$ to $R^{60}$, $R^{61}$ to $R^{68}$, and $R^{71}$ to $R^{78}$ each independently represent a group represented by any of the above-mentioned general formulae (3) to (6). The number of the substituents in the general formulae (3) to (6) is not specifically limited. Also preferred is a case where all are unsubstituted (that is, all are hydrogen atoms). In the case where the general formulae (3) to (6) each have two or more substituents, those substituents may be the same as or different from each other. In the case where the general formulae (3) to (6) each have a substituent, the substituent is preferably any of $R^{42}$ to $R^{46}$, and more preferably at least one of $R^{45}$ and $R^{46}$. In the general formula (4), preferably, any of $R^{52}$ to $R^{59}$ is a substituent; in the general formula (5), preferably, any of $R^{62}$ to $R^{67}$ is a substituent; and in the general formula (6), preferably, any of $R^{72}$ to $R^{77}$ is a substituent.

In the general formulae (3) to (6), $R^{41}$ and $R^{42}$, $R^{42}$ and $R^{43}$, $R^{43}$ and $R^{44}$, $R^{45}$ and $R^{46}$, $R^{51}$ and $R^{52}$, $R^{52}$ and $R^{53}$, $R^{53}$ and $R^{54}$, $R^{54}$ and $R^{55}$, $R^{55}$ and $R^{56}$, $R^{56}$ and $R^{57}$, $R^{57}$ and $R^{58}$, $R^{58}$ and $R^{59}$, $R^{59}$ and $R^{60}$, $R^{61}$ and $R^{62}$, $R^{62}$ and $R^{63}$, $R^{63}$ and $R^{64}$, $R^{65}$ and $R^{66}$, $R^{66}$ and $R^{67}$, $R^{67}$ and $R^{68}$, $R^{71}$ and $R^{72}$, $R^{72}$ and $R^{73}$, $R^{73}$ and $R^{74}$, $R^{75}$ and $R^{76}$, $R^{76}$ and $R^{77}$, and $R^{77}$ and $R^{78}$ each may bond to each other to form a cyclic structure. Regarding the description and preferred examples of the cyclic structure, reference may be made to the description and the preferred examples of the cyclic structure that is formed by $R^{21}$ and $R^{22}$ and the like in the general formula (2b) each bonding to each other.

In the general formula (6), X represents an oxygen atom, a sulfur atom, a substituted or unsubstituted nitrogen atom, a substituted or unsubstituted carbon atom, a substituted or unsubstituted silicon atom or a carbonyl group, which is divalent and which has a linking chain length of one atom, or represents a substituted or unsubstituted ethylene group, a substituted or unsubstituted vinylene group, a substituted or unsubstituted o-arylene group or a substituted or unsubstituted o-heteroarylene group, which is divalent and which has a bonding chain length of two atoms. Regarding specific examples and preferred ranges of the substituent, reference may be made to the corresponding description of the substituent for the arylene group or the heteroarylene group represented by $R^{11}$ in the general formula (2a).

In the general formulae (3) to (6), $L^{11}$ to $L^{14}$ each independently represent a single bond, a substituted or unsubstituted arylene group, or a substituted or unsubstituted heteroarylene group. Here, the substituent for the arylene group or the heteroarylene group may be a group represented by any of the general formulae (1) to (6). The groups represented by the general formulae (1) to (6) may be introduced into $L^{11}$ to $L^{14}$ up to the largest number of substituents that can be introduced thereinto. In the case where multiple groups of the general formulae (1) to (6) are introduced, these substituents may be the same as or different from each other.

* indicates a bonding position to the carbon atom (C) constituting a ring skeleton of the benzene ring in the general formula (1). Regarding the description and preferred ranges of the arylene group or the heteroarylene group represented by $L^{11}$ to $L^{14}$ and those of the substituents that may be introduced into these groups, reference may be made to the description and the preferred ranges of the arylene group or the heteroarylene group represented by L and those of the substituents that may be introduced into the group. Preferably, $L^{11}$ to $L^{14}$ each are a single bond, or a substituted or unsubstituted arylene group.

Specific examples of the substituted amino group are shown below; however, the substituted amino group employable in the present invention should not be limitatively interpreted by these specific examples. * indicates a bonding position to the linking group (L) in the general formulae (2a) to (2c).

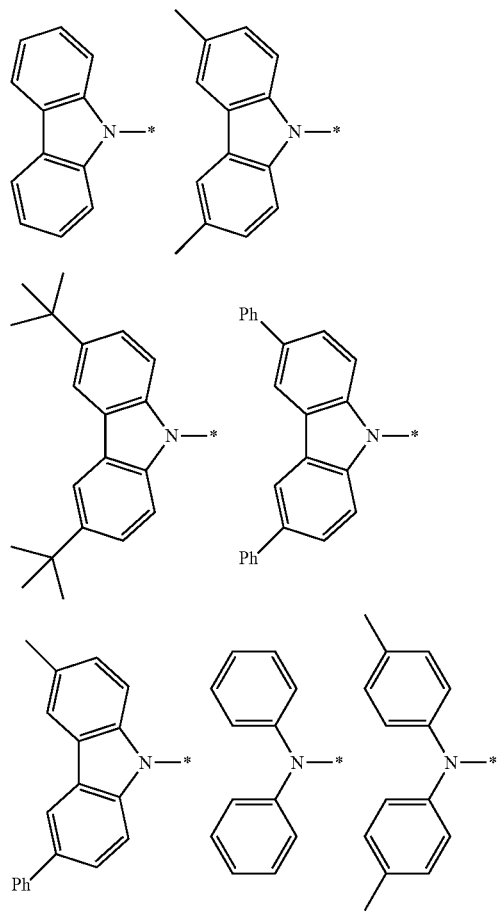

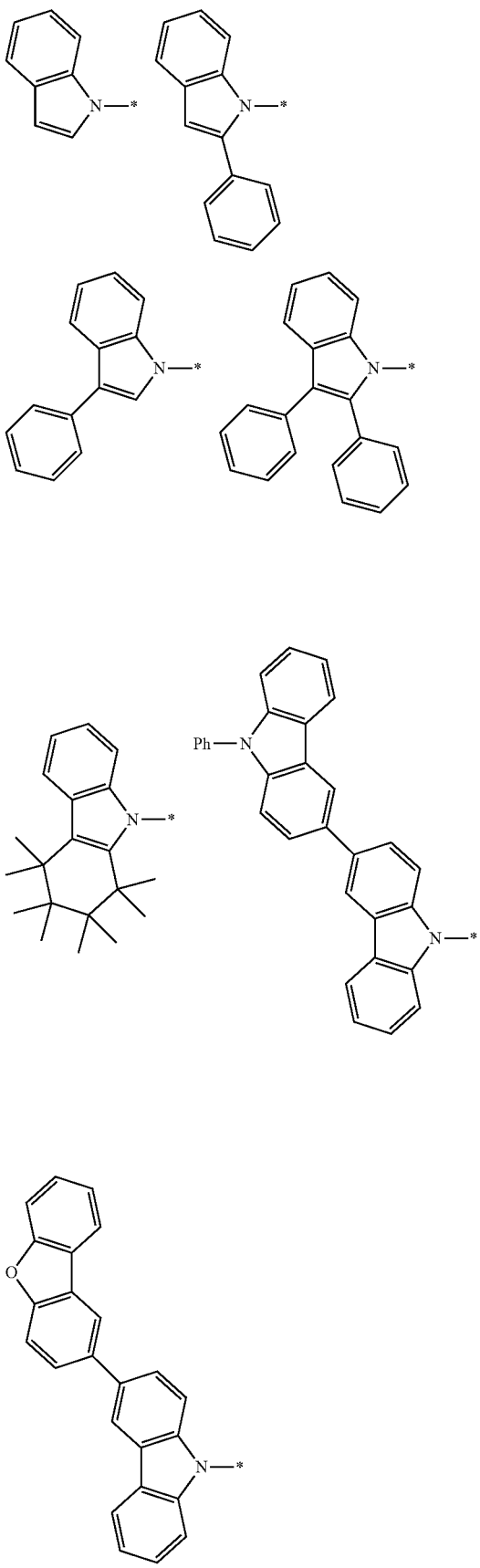

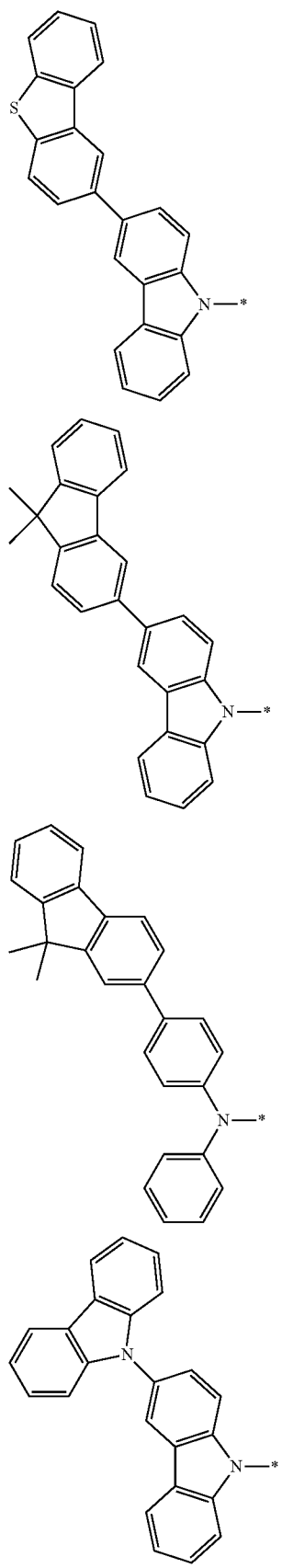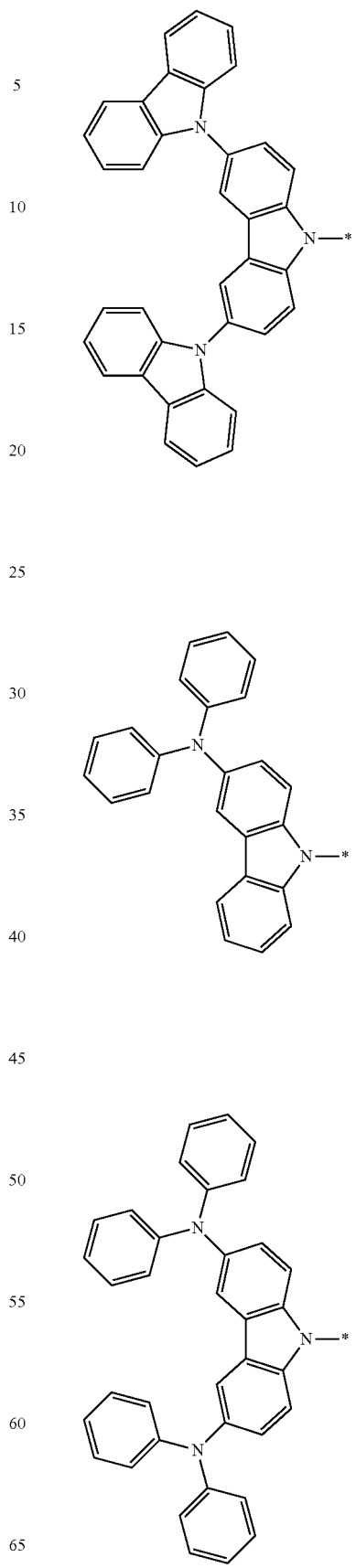

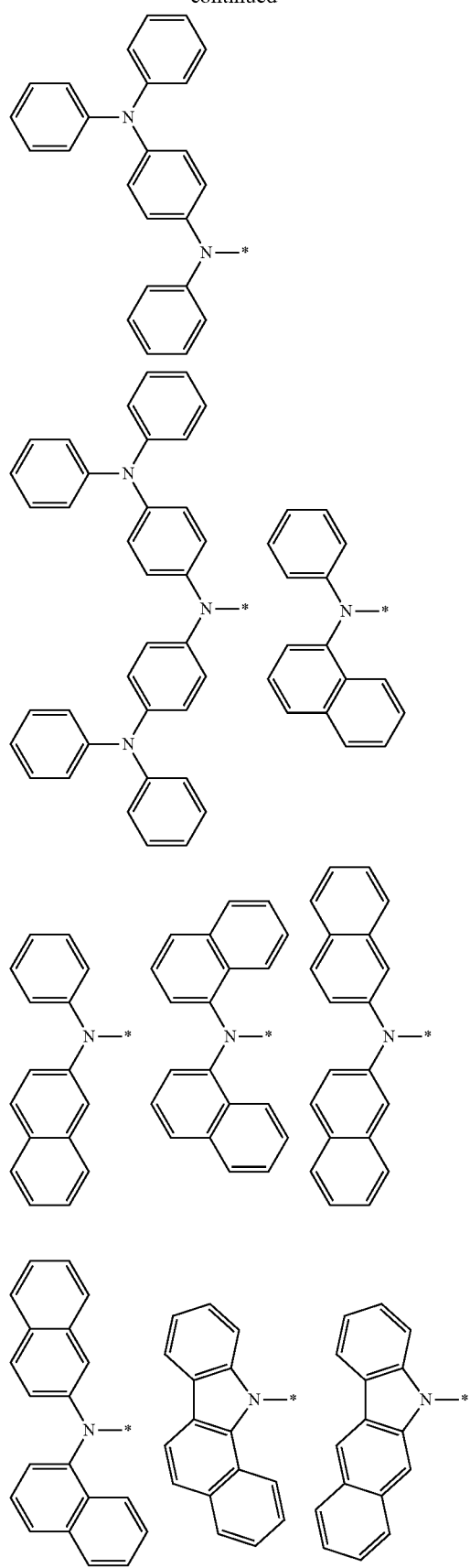
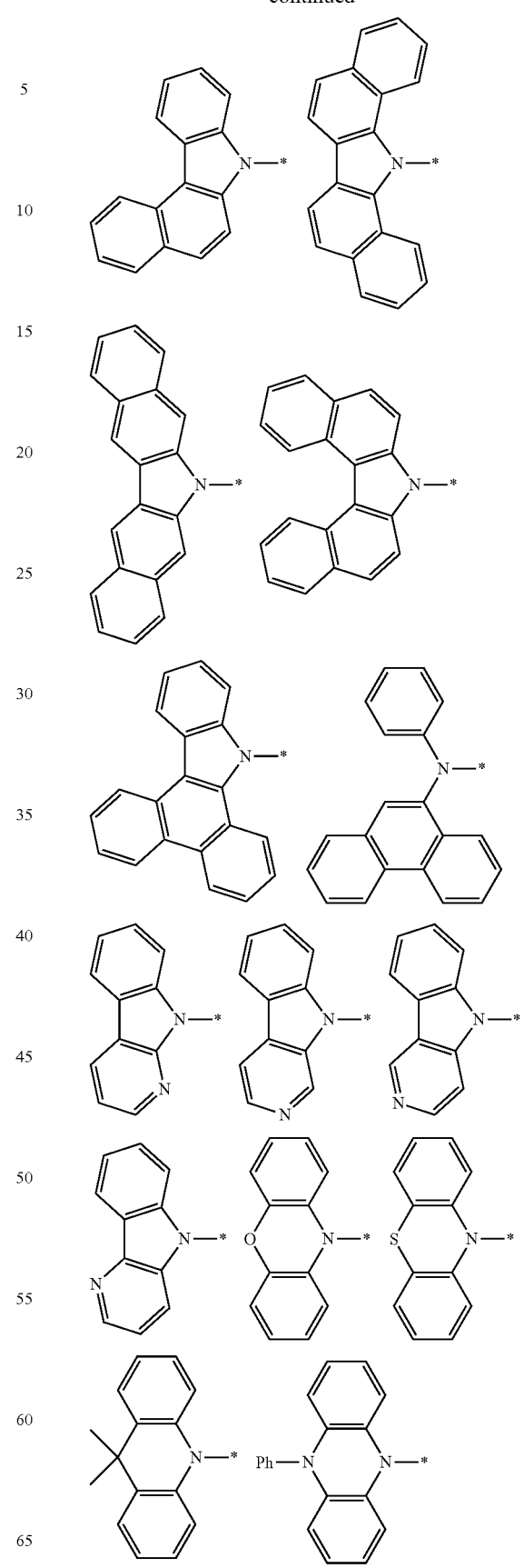

-continued
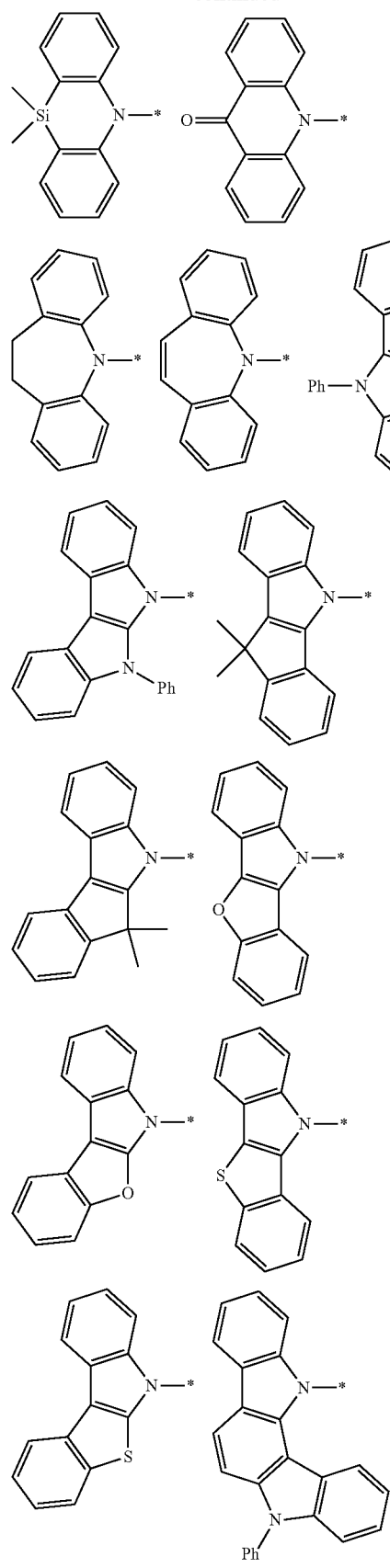
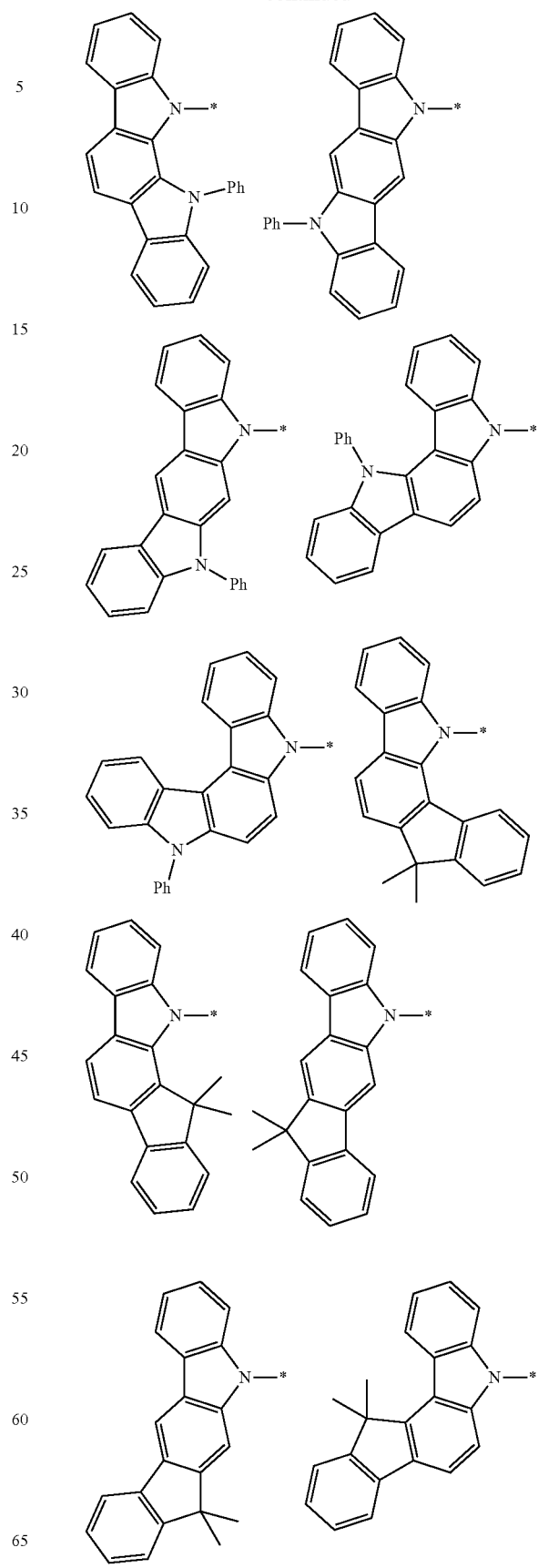

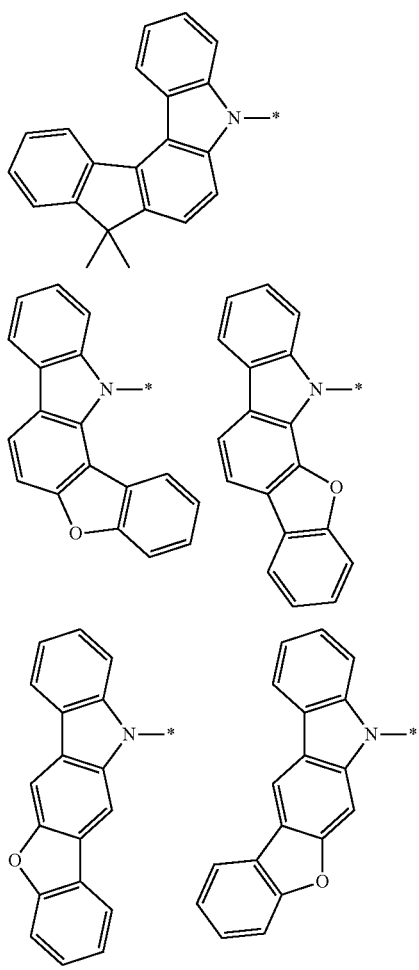
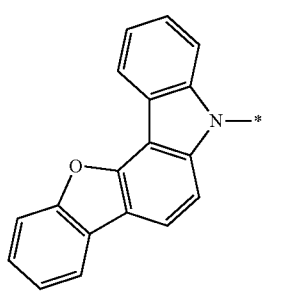
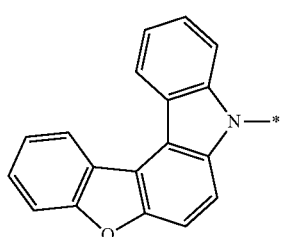
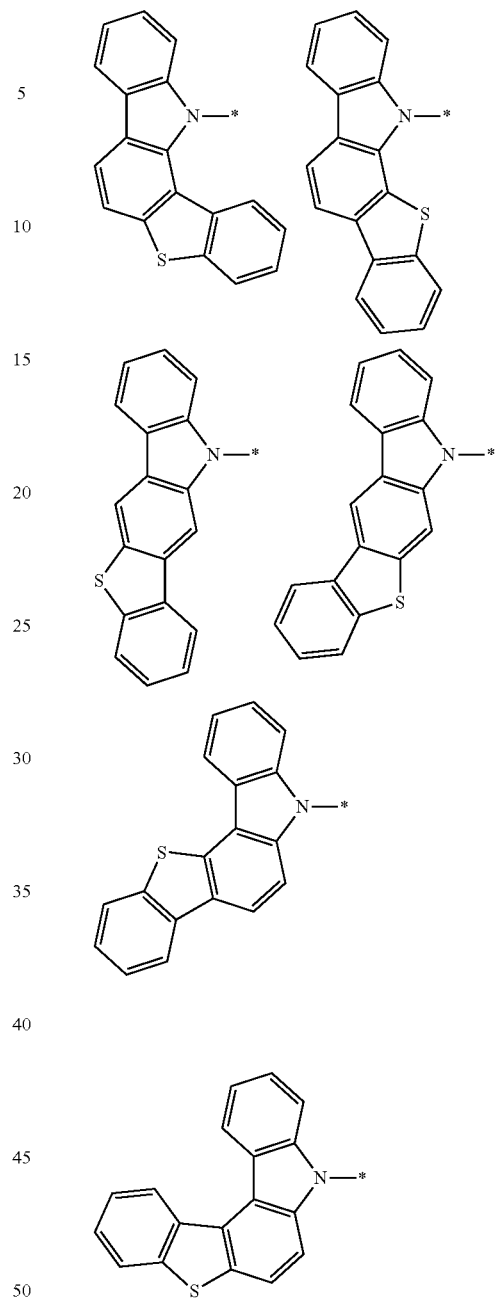

When two or more of $R^1$ to $R^5$ in the general formula (1) are D's, these multiple D's may be the same as or different from each other.

In the case where D's are different, preferably, two D's each have an aromatic ring, and the aromatic ring is common between the two D's, but the two differ from each other in point of at least one condition of the number of the substituents on the aromatic ring, the substitution site of the aromatic ring substituted with the substituent, and the structure of the substituent on the aromatic ring.

Specific examples of the group represented by D are shown below; however, D that is employable in the present invention should not be limitatively interpreted by these specific examples.

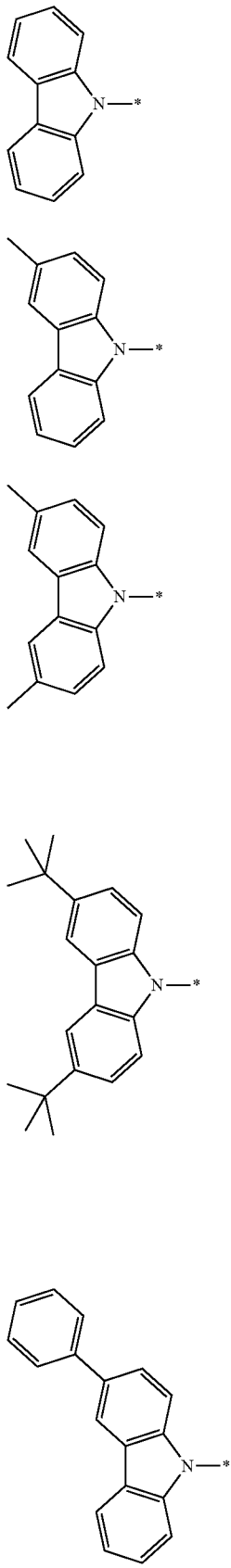
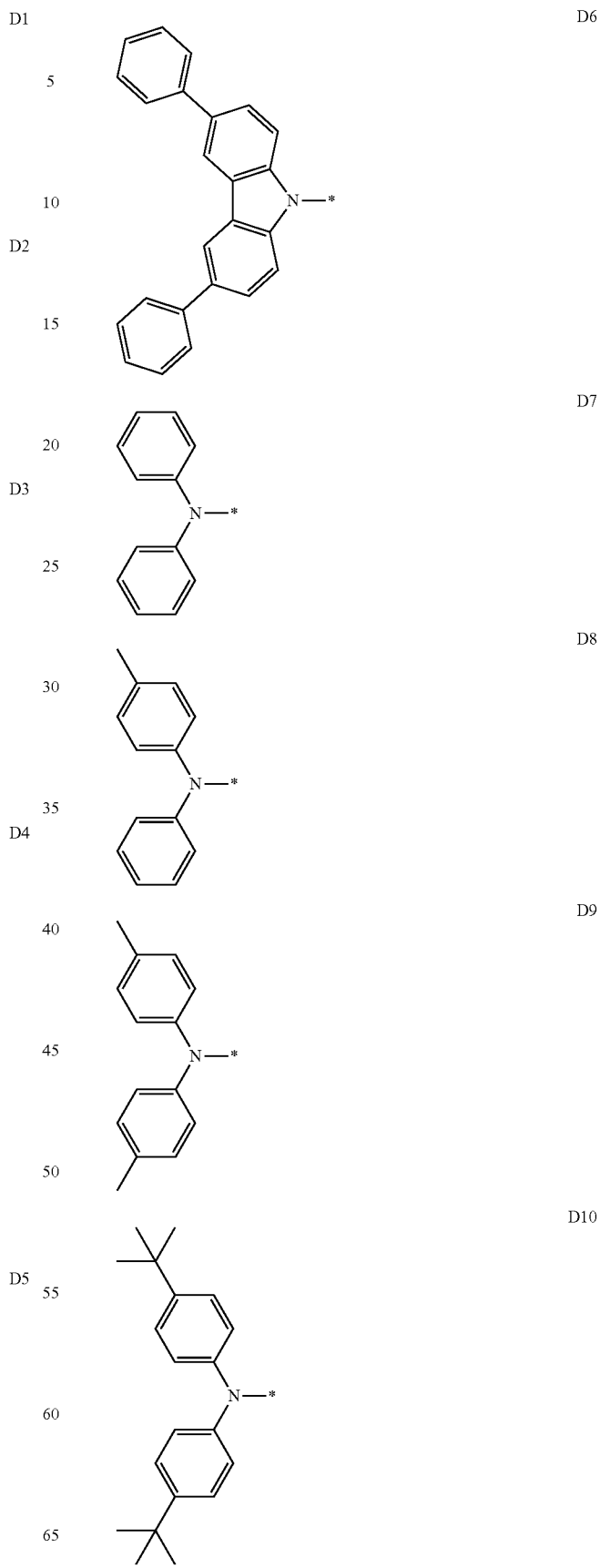

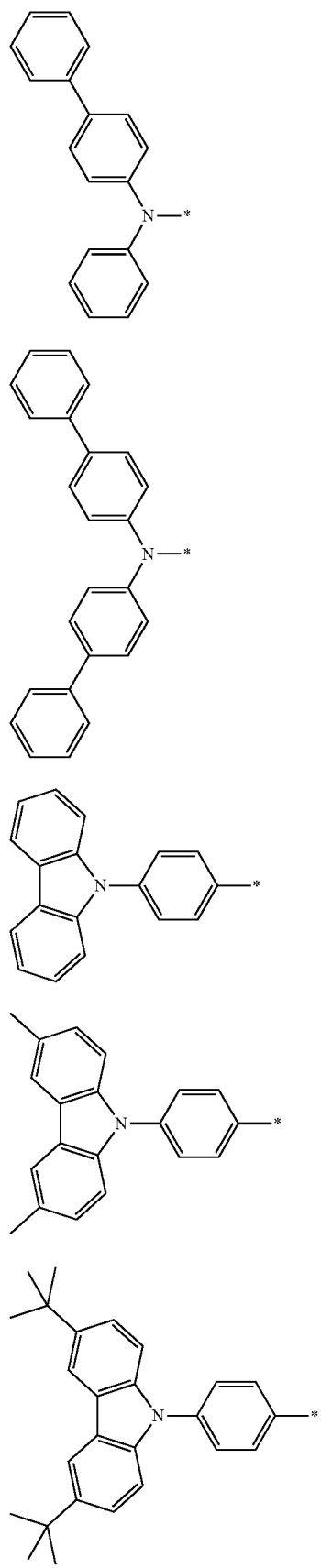
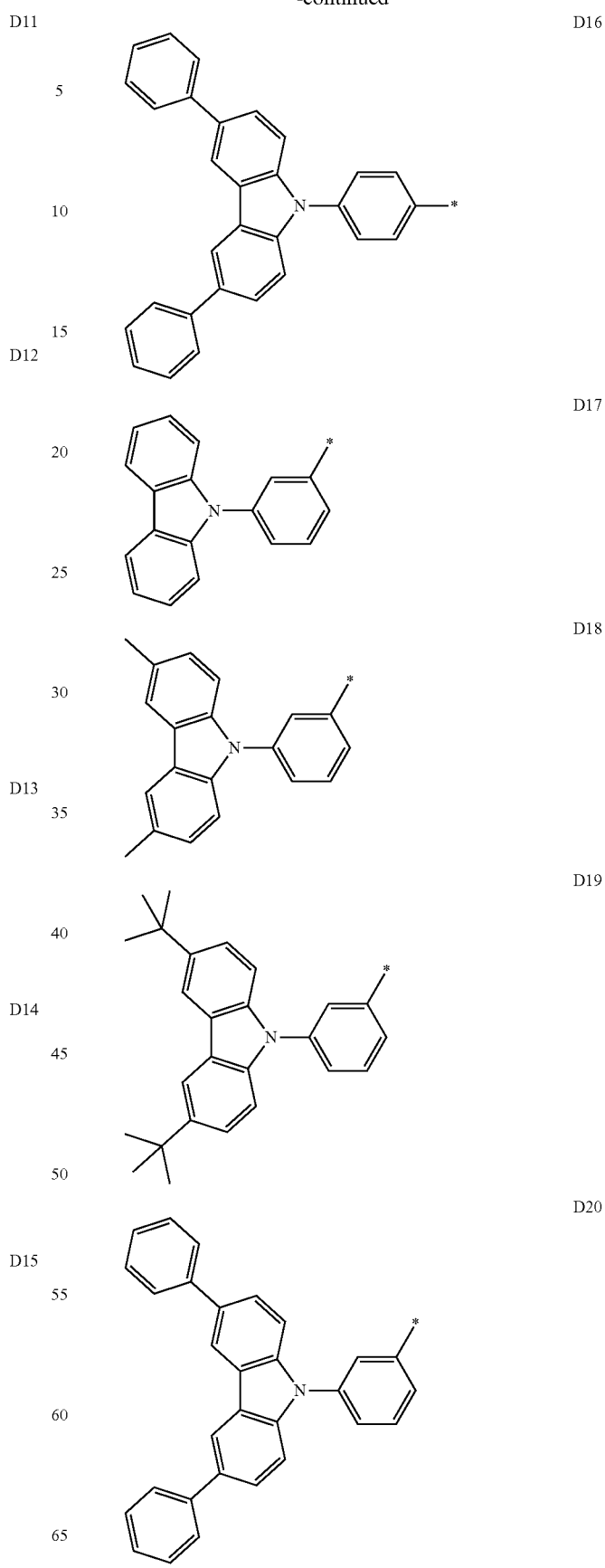

-continued

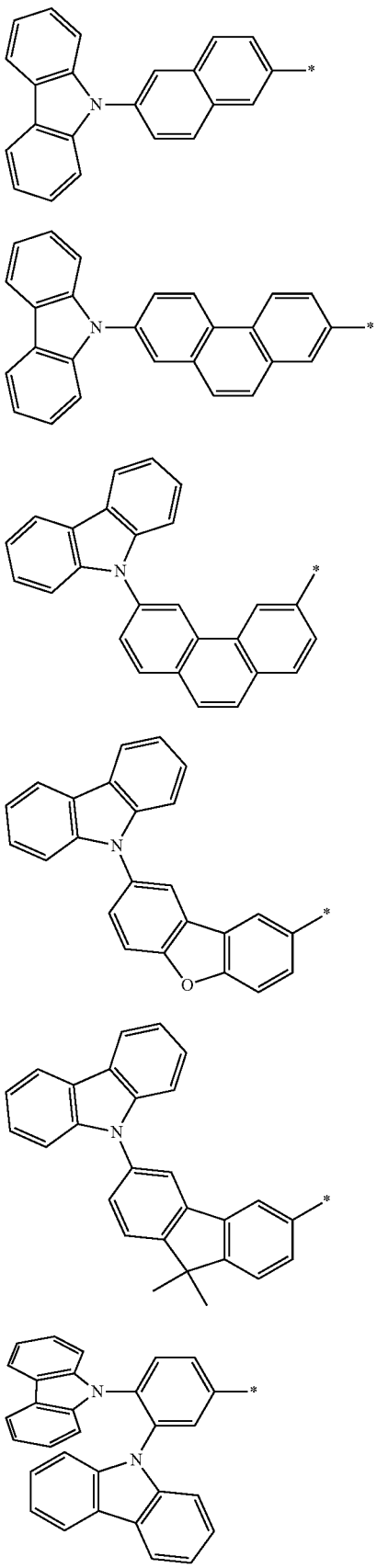

D21

D22

D23

D24

D25

D26

-continued

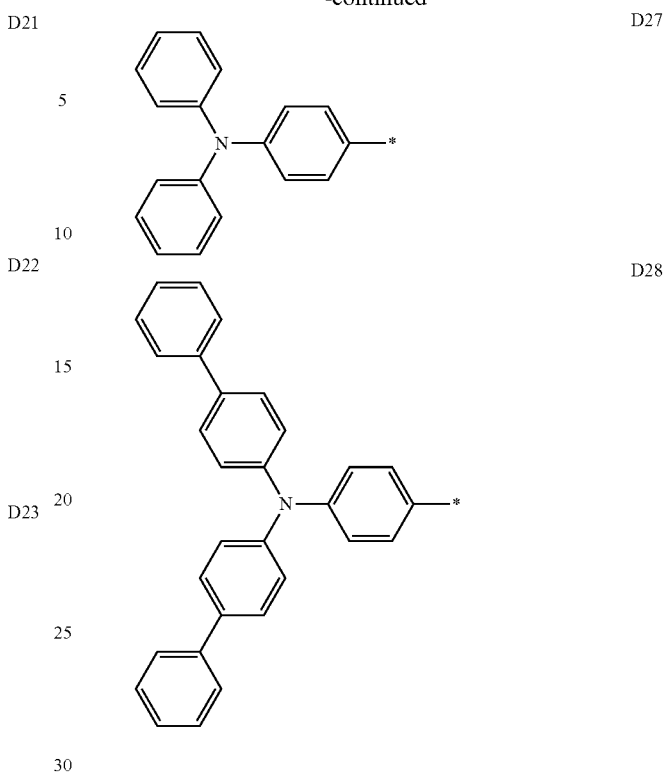

D27

D28

In the general formula (1), at least any one of $R^1$ to $R^5$ is a cyano group and at least one is Ar, and at least one is D. The remaining two may be hydrogen atoms, or may be Ar's or D's, or may also be any other substituent than Ar and D (but excepting a cyano group). Preferably, the remaining two are selected from a hydrogen atom, Ar and D, and is more preferably selected from Ar and D. For example, one of the remaining two may be Ar and the other may be D.

The general formula (1) may be a symmetric compound or may also be an asymmetric compound.

The compound represented by the general formula (1) is preferably such that the energy difference $\Delta E_{ST}$ between the lowest excited singlet energy level ($E_{S1}$) and the lowest excited triplet energy level ($E_{T1}$) thereof is 0.9 or less as a relative value based on $\Delta E_{ST}$, 1, of a reference compound prepared by removing Ar from the compound, more preferably 0.8 or less, even more preferably 0.7 or less, still more preferably 0.6 or less, further more preferably 0.5 or less, and especially preferably 0.4 or less. The compound having such a smaller $\Delta E_{ST}$ than that of a reference compound can more readily undergo reverse intersystem crossing from the excited triplet state to the excited singlet state among delayed fluorescent materials and tends to have a shorter lifetime of delayed fluorescence. When a light-emitting material having a short delayed fluorescence lifetime is used in an electroluminescent device, the device can be free from a problem of emission efficiency reduction owing to exciton accumulation in a high-current density region and a problem of device degradation in long-term driving, and the device performance can be improved.

$\Delta E_{ST}$ of the compound can be determined from the fluorescence spectrum and the phosphorescence spectrum thereof, and can also be calculated according to computational chemistry. The relative value (based on $\Delta E_{ST}$ of a reference compound, 1) determined according to these methods well dovetails with each other. Regarding the computational method for $\Delta E_{ST}$ of from a fluorescence spectrum and a phosphorescence spectrum and the computational method for $\Delta E_{ST}$ according to computational chemistry, reference may be made to the description in the section of Examples given hereinunder.

The compound represented by the general formula (1) has a wide variation of emission colors among cyanobenzene derivatives. Consequently, the present invention can provide useful compounds even in a blue region.

Specific examples of the compound represented by the general formula (1) are shown below. However, the compound represented by the general formula (1) employable in the present invention should not be limitatively interpreted by the following specific examples.

TABLE 1

| No | R$^1$ | R$^2$ | R$^3$ | R$^4$ | R$^5$ |
|---|---|---|---|---|---|
| 1 | D1 | D1 | CN | D1 | Ar1 |
| 2 | D1 | D1 | CN | Ar1 | Ar1 |
| 3 | D1 | Ar1 | CN | D1 | Ar1 |
| 4 | Ar1 | D1 | CN | D1 | Ar1 |
| 5 | D1 | Ar1 | CN | Ar1 | Ar1 |
| 6 | D1 | D1 | CN | H | Ar1 |
| 7 | D1 | H | CN | D1 | Ar1 |
| 8 | D1 | H | CN | Ar1 | D1 |
| 9 | D1 | H | CN | Ar1 | Ar1 |
| 10 | D1 | Ar1 | CN | H | Ar1 |
| 11 | D1 | Ar1 | CN | Ar1 | H |
| 12 | D1 | H | CN | H | Ar1 |
| 13 | D1 | H | CN | Ar1 | H |
| 14 | D1 | Ar1 | CN | H | H |
| 15 | CN | D1 | D1 | D1 | Ar1 |
| 16 | CN | D1 | D1 | Ar1 | D1 |
| 17 | CN | D1 | D1 | Ar1 | Ar1 |
| 18 | CN | D1 | Ar1 | D1 | Ar1 |
| 19 | CN | Ar1 | D1 | D1 | Ar1 |
| 20 | CN | D1 | Ar1 | Ar1 | Ar1 |
| 21 | CN | Ar1 | D1 | Ar1 | Ar1 |
| 22 | CN | D1 | H | Ar1 | D1 |
| 23 | CN | D1 | H | D1 | Ar1 |
| 24 | CN | D1 | Ar1 | D1 | H |
| 25 | CN | D1 | D1 | Ar1 | H |
| 26 | CN | H | D1 | D1 | Ar1 |
| 27 | CN | D1 | H | Ar1 | Ar1 |
| 28 | CN | D1 | Ar1 | H | Ar1 |
| 29 | CN | H | Ar1 | D1 | Ar1 |
| 30 | CN | Ar1 | D1 | H | Ar1 |
| 31 | CN | D1 | Ar1 | Ar1 | H |
| 32 | CN | Ar1 | D1 | H | H |
| 33 | CN | Ar1 | H | D1 | H |
| 34 | CN | D1 | H | Ar1 | H |
| 35 | CN | H | D1 | Ar1 | H |
| 36 | CN | D1 | H | H | Ar1 |
| 37 | CN | D1 | Ar1 | Ar1 | D1 |
| 38 | D1 | CN | D1 | D1 | D1 |
| 39 | D1 | CN | D1 | Ar1 | D1 |
| 40 | Ar1 | CN | D1 | D1 | D1 |
| 41 | D1 | CN | D1 | Ar1 | Ar1 |
| 42 | D1 | CN | Ar1 | D1 | Ar1 |
| 43 | Ar1 | CN | D1 | D1 | Ar1 |
| 44 | Ar1 | CN | D1 | Ar1 | D1 |
| 45 | D1 | CN | Ar1 | Ar1 | Ar1 |
| 46 | Ar1 | CN | D1 | Ar1 | Ar1 |
| 47 | Ar1 | CN | Ar1 | D1 | Ar1 |
| 48 | D1 | CN | D1 | H | Ar1 |
| 49 | D1 | CN | H | D1 | Ar1 |
| 50 | H | CN | D1 | D1 | Ar1 |
| 51 | Ar1 | CN | D1 | D1 | H |
| 52 | H | CN | D1 | Ar1 | D1 |
| 53 | Ar1 | CN | D1 | H | D1 |
| 54 | Ar1 | CN | Ar1 | H | D1 |
| 55 | Ar1 | CN | H | Ar1 | D1 |
| 56 | H | CN | Ar1 | D1 | Ar1 |
| 57 | D1 | CN | Ar1 | Ar1 | H |
| 58 | H | CN | Ar1 | D1 | Ar1 |
| 59 | D1 | CN | Ar1 | H | Ar1 |
| 60 | H | CN | H | D1 | Ar1 |

TABLE 1-continued

| No | R$^1$ | R$^2$ | R$^3$ | R$^4$ | R$^5$ |
|---|---|---|---|---|---|
| 61 | H | CN | D1 | H | Ar1 |
| 62 | D1 | CN | H | H | Ar1 |
| 63 | Ar1 | CN | H | H | D1 |
| 64 | D1 | CN | H | Ar1 | H |
| 65 | Ar1 | CN | H | D1 | H |
| 66 | D1 | Ar2 | CN | D1 | Ar2 |
| 67 | D1 | Ar3 | CN | D1 | Ar3 |
| 68 | D1 | Ar4 | CN | D1 | Ar4 |
| 69 | D1 | Ar5 | CN | D1 | Ar5 |
| 70 | D1 | Ar6 | CN | D1 | Ar6 |
| 71 | D1 | Ar7 | CN | D1 | Ar7 |
| 72 | D1 | Ar8 | CN | D1 | Ar8 |
| 73 | D1 | Ar9 | CN | D1 | Ar9 |
| 74 | D1 | Ar10 | CN | D1 | Ar10 |
| 75 | D1 | Ar11 | CN | D1 | Ar11 |
| 76 | D1 | Ar12 | CN | D1 | Ar12 |
| 77 | D1 | Ar13 | CN | D1 | Ar13 |
| 78 | D1 | Ar14 | CN | D1 | Ar14 |
| 79 | D1 | Ar15 | CN | D1 | Ar15 |
| 80 | D1 | Ar16 | CN | D1 | Ar16 |
| 81 | D1 | Ar17 | CN | D1 | Ar17 |
| 82 | D1 | Ar18 | CN | D1 | Ar18 |
| 83 | D1 | Ar19 | CN | D1 | Ar19 |
| 84 | D1 | Ar20 | CN | D1 | Ar20 |
| 85 | D1 | Ar21 | CN | D1 | Ar21 |
| 86 | D1 | Ar22 | CN | D1 | Ar22 |
| 87 | D1 | Ar23 | CN | D1 | Ar23 |
| 88 | D1 | Ar24 | CN | D1 | Ar24 |

TABLE 2

| No | R$^1$ | R$^2$ | R$^3$ | R$^4$ | R$^5$ |
|---|---|---|---|---|---|
| 89 | D1 | Ar25 | CN | D1 | Ar25 |
| 90 | D1 | Ar26 | CN | D1 | Ar26 |
| 91 | D1 | Ar27 | CN | D1 | Ar27 |
| 92 | D1 | Ar28 | CN | D1 | Ar28 |
| 93 | D1 | Ar29 | CN | D1 | Ar29 |
| 94 | D1 | Ar30 | CN | D1 | Ar30 |
| 95 | D1 | Ar31 | CN | D1 | Ar31 |
| 96 | D1 | Ar32 | CN | D1 | Ar32 |
| 97 | D1 | Ar33 | CN | D1 | Ar33 |
| 98 | D2 | Ar1 | CN | D2 | Ar1 |
| 99 | D3 | Ar1 | CN | D3 | Ar1 |
| 100 | D4 | Ar1 | CN | D4 | Ar1 |
| 101 | D5 | Ar1 | CN | D5 | Ar1 |
| 102 | D6 | Ar1 | CN | D6 | Ar1 |
| 103 | D7 | Ar1 | CN | D7 | Ar1 |
| 104 | D8 | Ar1 | CN | D8 | Ar1 |
| 105 | D9 | Ar1 | CN | D9 | Ar1 |
| 106 | D10 | Ar1 | CN | D10 | Ar1 |
| 107 | D11 | Ar1 | CN | D11 | Ar1 |
| 108 | D12 | Ar1 | CN | D12 | Ar1 |
| 109 | D13 | Ar1 | CN | D13 | Ar1 |
| 110 | D14 | Ar1 | CN | D14 | Ar1 |
| 111 | D15 | Ar1 | CN | D15 | Ar1 |
| 112 | D16 | Ar1 | CN | D16 | Ar1 |
| 113 | D17 | Ar1 | CN | D17 | Ar1 |
| 114 | D18 | Ar1 | CN | D18 | Ar1 |
| 115 | D19 | Ar1 | CN | D19 | Ar1 |
| 116 | D20 | Ar1 | CN | D20 | Ar1 |
| 117 | D21 | Ar1 | CN | D21 | Ar1 |
| 118 | D22 | Ar1 | CN | D22 | Ar1 |
| 119 | D23 | Ar1 | CN | D23 | Ar1 |
| 120 | D24 | Ar1 | CN | D24 | Ar1 |
| 121 | D25 | Ar1 | CN | D25 | Ar1 |
| 122 | D26 | Ar1 | CN | D26 | Ar1 |
| 123 | D27 | Ar1 | CN | D27 | Ar1 |
| 124 | D28 | Ar1 | CN | D28 | Ar1 |
| 125 | D1 | CN | Ar2 | D1 | Ar2 |
| 126 | D1 | CN | Ar3 | D1 | Ar3 |
| 127 | D1 | CN | Ar4 | D1 | Ar4 |
| 128 | D1 | CN | Ar5 | D1 | Ar5 |
| 129 | D1 | CN | Ar6 | D1 | Ar6 |
| 130 | D1 | CN | Ar7 | D1 | Ar7 |

TABLE 2-continued

| No | R¹ | R² | R³ | R⁴ | R⁵ |
|---|---|---|---|---|---|
| 131 | D1 | CN | Ar8 | D1 | Ar8 |
| 132 | D1 | CN | Ar9 | D1 | Ar9 |
| 133 | D1 | CN | Ar10 | D1 | Ar10 |
| 134 | D1 | CN | Ar11 | D1 | Ar11 |
| 135 | D1 | CN | Ar12 | D1 | Ar12 |
| 136 | D1 | CN | Ar13 | D1 | Ar13 |
| 137 | D1 | CN | Ar14 | D1 | Ar14 |
| 138 | D1 | CN | Ar15 | D1 | Ar15 |
| 139 | D1 | CN | Ar16 | D1 | Ar16 |
| 140 | D1 | CN | Ar17 | D1 | Ar17 |
| 141 | D1 | CN | Ar18 | D1 | Ar18 |
| 142 | D1 | CN | Ar19 | D1 | Ar19 |
| 143 | D1 | CN | Ar20 | D1 | Ar20 |
| 144 | D1 | CN | Ar21 | D1 | Ar21 |
| 145 | D1 | CN | Ar22 | D1 | Ar22 |
| 146 | D1 | CN | Ar23 | D1 | Ar23 |
| 147 | D1 | CN | Ar24 | D1 | Ar24 |
| 148 | D1 | CN | Ar25 | D1 | Ar25 |
| 149 | D1 | CN | Ar26 | D1 | Ar26 |
| 150 | D1 | CN | Ar27 | D1 | Ar27 |
| 151 | D1 | CN | Ar28 | D1 | Ar28 |
| 152 | D1 | CN | Ar29 | D1 | Ar29 |
| 153 | D1 | CN | Ar30 | D1 | Ar30 |
| 154 | D1 | CN | Ar31 | D1 | Ar31 |
| 155 | D1 | CN | Ar32 | D1 | Ar32 |
| 156 | D1 | CN | Ar33 | D1 | Ar33 |
| 157 | D2 | CN | Ar1 | D2 | Ar1 |
| 158 | D3 | CN | Ar1 | D3 | Ar1 |
| 159 | D4 | CN | Ar1 | D4 | Ar1 |
| 160 | D5 | CN | Ar1 | D5 | Ar1 |
| 161 | D6 | CN | Ar1 | D6 | Ar1 |
| 162 | D7 | CN | Ar1 | D7 | Ar1 |
| 163 | D8 | CN | Ar1 | D8 | Ar1 |
| 164 | D9 | CN | Ar1 | D9 | Ar1 |
| 165 | D10 | CN | Ar1 | D10 | Ar1 |
| 166 | D11 | CN | Ar1 | D11 | Ar1 |
| 167 | D12 | CN | Ar1 | D12 | Ar1 |
| 168 | D13 | CN | Ar1 | D13 | Ar1 |
| 169 | D14 | CN | Ar1 | D14 | Ar1 |
| 170 | D15 | CN | Ar1 | D15 | Ar1 |
| 171 | D16 | CN | Ar1 | D16 | Ar1 |
| 172 | D17 | CN | Ar1 | D17 | Ar1 |
| 173 | D18 | CN | Ar1 | D18 | Ar1 |
| 174 | D19 | CN | Ar1 | D19 | Ar1 |
| 175 | D20 | CN | Ar1 | D20 | Ar1 |
| 176 | D21 | CN | Ar1 | D21 | Ar1 |

TABLE 3

| No | R¹ | R² | R³ | R⁴ | R⁵ |
|---|---|---|---|---|---|
| 177 | D22 | CN | Ar1 | D22 | Ar1 |
| 178 | D23 | CN | Ar1 | D23 | Ar1 |
| 179 | D24 | CN | Ar1 | D24 | Ar1 |
| 180 | D25 | CN | Ar1 | D25 | Ar1 |
| 181 | D26 | CN | Ar1 | D26 | Ar1 |
| 182 | D27 | CN | Ar1 | D27 | Ar1 |
| 183 | D28 | CN | Ar1 | D28 | Ar1 |
| 184 | Ar2 | CN | D1 | Ar2 | D1 |
| 185 | Ar3 | CN | D1 | Ar3 | D1 |
| 186 | Ar4 | CN | D1 | Ar4 | D1 |
| 187 | Ar5 | CN | D1 | Ar5 | D1 |
| 188 | Ar6 | CN | D1 | Ar6 | D1 |
| 189 | Ar7 | CN | D1 | Ar7 | D1 |
| 190 | Ar8 | CN | D1 | Ar8 | D1 |
| 191 | Ar9 | CN | D1 | Ar9 | D1 |
| 192 | Ar10 | CN | D1 | Ar10 | D1 |
| 193 | Ar11 | CN | D1 | Ar11 | D1 |
| 194 | Ar12 | CN | D1 | Ar12 | D1 |
| 195 | Ar13 | CN | D1 | Ar13 | D1 |
| 196 | Ar14 | CN | D1 | Ar14 | D1 |
| 197 | Ar15 | CN | D1 | Ar15 | D1 |
| 198 | Ar16 | CN | D1 | Ar16 | D1 |
| 199 | Ar17 | CN | D1 | Ar17 | D1 |
| 200 | Ar18 | CN | D1 | Ar18 | D1 |

TABLE 3-continued

| No | R¹ | R² | R³ | R⁴ | R⁵ |
|---|---|---|---|---|---|
| 201 | Ar19 | CN | D1 | Ar19 | D1 |
| 202 | Ar20 | CN | D1 | Ar20 | D1 |
| 203 | Ar21 | CN | D1 | Ar21 | D1 |
| 204 | Ar22 | CN | D1 | Ar22 | D1 |
| 205 | Ar23 | CN | D1 | Ar23 | D1 |
| 206 | Ar24 | CN | D1 | Ar24 | D1 |
| 207 | Ar25 | CN | D1 | Ar25 | D1 |
| 208 | Ar26 | CN | D1 | Ar26 | D1 |
| 209 | Ar27 | CN | D1 | Ar27 | D1 |
| 210 | Ar28 | CN | D1 | Ar28 | D1 |
| 211 | Ar29 | CN | D1 | Ar29 | D1 |
| 212 | Ar30 | CN | D1 | Ar30 | D1 |
| 213 | Ar31 | CN | D1 | Ar31 | D1 |
| 214 | Ar32 | CN | D1 | Ar32 | D1 |
| 215 | Ar33 | CN | D1 | Ar33 | D1 |
| 216 | Ar1 | CN | D2 | Ar1 | D2 |
| 217 | Ar1 | CN | D3 | Ar1 | D3 |
| 218 | Ar1 | CN | D4 | Ar1 | D4 |
| 219 | Ar1 | CN | D5 | Ar1 | D5 |
| 220 | Ar1 | CN | D6 | Ar1 | D6 |
| 221 | Ar1 | CN | D7 | Ar1 | D7 |
| 222 | Ar1 | CN | D8 | Ar1 | D8 |
| 223 | Ar1 | CN | D9 | Ar1 | D9 |
| 224 | Ar1 | CN | D10 | Ar1 | D10 |
| 225 | Ar1 | CN | D11 | Ar1 | D11 |
| 226 | Ar1 | CN | D12 | Ar1 | D12 |
| 227 | Ar1 | CN | D13 | Ar1 | D13 |
| 228 | Ar1 | CN | D14 | Ar1 | D14 |
| 229 | Ar1 | CN | D15 | Ar1 | D15 |
| 230 | Ar1 | CN | D16 | Ar1 | D16 |
| 231 | Ar1 | CN | D17 | Ar1 | D17 |
| 232 | Ar1 | CN | D18 | Ar1 | D18 |
| 233 | Ar1 | CN | D19 | Ar1 | D19 |
| 234 | Ar1 | CN | D20 | Ar1 | D20 |
| 235 | Ar1 | CN | D21 | Ar1 | D21 |
| 236 | Ar1 | CN | D22 | Ar1 | D22 |
| 237 | Ar1 | CN | D23 | Ar1 | D23 |
| 238 | Ar1 | CN | D24 | Ar1 | D24 |
| 239 | Ar1 | CN | D25 | Ar1 | D25 |
| 240 | Ar1 | CN | D26 | Ar1 | D26 |
| 241 | Ar1 | CN | D27 | Ar1 | D27 |
| 242 | Ar1 | CN | D28 | Ar1 | D28 |
| 243 | D1 | CN | D1 | Ar2 | D1 |
| 244 | D1 | CN | D1 | Ar3 | D1 |
| 245 | D1 | CN | D1 | Ar4 | D1 |
| 246 | D1 | CN | D1 | Ar5 | D1 |
| 247 | D1 | CN | D1 | Ar6 | D1 |
| 248 | D1 | CN | D1 | Ar7 | D1 |
| 249 | D1 | CN | D1 | Ar8 | D1 |
| 250 | D1 | CN | D1 | Ar9 | D1 |
| 251 | D1 | CN | D1 | Ar10 | D1 |
| 252 | D1 | CN | D1 | Ar11 | D1 |
| 253 | D1 | CN | D1 | Ar12 | D1 |
| 254 | D1 | CN | D1 | Ar13 | D1 |
| 255 | D1 | CN | D1 | Ar14 | D1 |
| 256 | D1 | CN | D1 | Ar15 | D1 |
| 257 | D1 | CN | D1 | Ar16 | D1 |
| 258 | D1 | CN | D1 | Ar17 | D1 |
| 259 | D1 | CN | D1 | Ar18 | D1 |
| 260 | D1 | CN | D1 | Ar19 | D1 |
| 261 | D1 | CN | D1 | Ar20 | D1 |
| 262 | D1 | CN | D1 | Ar21 | D1 |
| 263 | D1 | CN | D1 | Ar22 | D1 |
| 264 | D1 | CN | D1 | Ar23 | D1 |

TABLE 4

| No | R¹ | R² | R³ | R⁴ | R⁵ |
|---|---|---|---|---|---|
| 265 | D1 | CN | D1 | Ar24 | D1 |
| 266 | D1 | CN | D1 | Ar25 | D1 |
| 267 | D1 | CN | D1 | Ar26 | D1 |
| 268 | D1 | CN | D1 | Ar27 | D1 |
| 269 | D1 | CN | D1 | Ar28 | D1 |
| 270 | D1 | CN | D1 | Ar29 | D1 |

TABLE 4-continued

| No | R¹ | R² | R³ | R⁴ | R⁵ |
|---|---|---|---|---|---|
| 271 | D1 | CN | D1 | Ar30 | D1 |
| 272 | D1 | CN | D1 | Ar31 | D1 |
| 273 | D1 | CN | D1 | Ar32 | D1 |
| 274 | D1 | CN | D1 | Ar33 | D1 |
| 275 | D2 | CN | D2 | Ar1 | D2 |
| 276 | D3 | CN | D3 | Ar1 | D3 |
| 277 | D4 | CN | D4 | Ar1 | D4 |
| 278 | D5 | CN | D5 | Ar1 | D5 |
| 279 | D6 | CN | D6 | Ar1 | D6 |
| 280 | D7 | CN | D7 | Ar1 | D7 |
| 281 | D8 | CN | D8 | Ar1 | D8 |
| 282 | D9 | CN | D9 | Ar1 | D9 |
| 283 | D10 | CN | D10 | Ar1 | D10 |
| 284 | D11 | CN | D11 | Ar1 | D11 |
| 285 | D12 | CN | D12 | Ar1 | D12 |
| 286 | D13 | CN | D13 | Ar1 | D13 |
| 287 | D14 | CN | D14 | Ar1 | D14 |
| 288 | D15 | CN | D15 | Ar1 | D15 |
| 289 | D16 | CN | D16 | Ar1 | D16 |
| 290 | D17 | CN | D17 | Ar1 | D17 |
| 291 | D18 | CN | D18 | Ar1 | D18 |
| 292 | D19 | CN | D19 | Ar1 | D19 |
| 293 | D20 | CN | D20 | Ar1 | D20 |
| 294 | D21 | CN | D21 | Ar1 | D21 |
| 295 | D22 | CN | D22 | Ar1 | D22 |
| 296 | D23 | CN | D23 | Ar1 | D23 |
| 297 | D24 | CN | D24 | Ar1 | D24 |
| 298 | D25 | CN | D25 | Ar1 | D25 |
| 299 | D26 | CN | D26 | Ar1 | D26 |
| 300 | D27 | CN | D27 | Ar1 | D27 |
| 301 | D28 | CN | D28 | Ar1 | D28 |
| 302 | Ar2 | CN | D1 | D1 | D1 |
| 303 | Ar3 | CN | D1 | D1 | D1 |
| 304 | Ar4 | CN | D1 | D1 | D1 |
| 305 | Ar5 | CN | D1 | D1 | D1 |
| 306 | Ar6 | CN | D1 | D1 | D1 |
| 307 | Ar7 | CN | D1 | D1 | D1 |
| 308 | Ar8 | CN | D1 | D1 | D1 |
| 309 | Ar9 | CN | D1 | D1 | D1 |
| 310 | Ar10 | CN | D1 | D1 | D1 |
| 311 | Ar11 | CN | D1 | D1 | D1 |
| 312 | Ar12 | CN | D1 | D1 | D1 |
| 313 | Ar13 | CN | D1 | D1 | D1 |
| 314 | Ar14 | CN | D1 | D1 | D1 |
| 315 | Ar15 | CN | D1 | D1 | D1 |
| 316 | Ar16 | CN | D1 | D1 | D1 |
| 317 | Ar17 | CN | D1 | D1 | D1 |
| 318 | Ar18 | CN | D1 | D1 | D1 |
| 319 | Ar19 | CN | D1 | D1 | D1 |
| 320 | Ar20 | CN | D1 | D1 | D1 |
| 321 | Ar21 | CN | D1 | D1 | D1 |
| 322 | Ar22 | CN | D1 | D1 | D1 |
| 323 | Ar23 | CN | D1 | D1 | D1 |
| 324 | Ar24 | CN | D1 | D1 | D1 |
| 325 | Ar25 | CN | D1 | D1 | D1 |
| 326 | Ar26 | CN | D1 | D1 | D1 |
| 327 | Ar27 | CN | D1 | D1 | D1 |
| 328 | Ar28 | CN | D1 | D1 | D1 |
| 329 | Ar29 | CN | D1 | D1 | D1 |
| 330 | Ar30 | CN | D1 | D1 | D1 |
| 331 | Ar31 | CN | D1 | D1 | D1 |
| 332 | Ar32 | CN | D1 | D1 | D1 |
| 333 | Ar33 | CN | D1 | D1 | D1 |
| 334 | Ar1 | CN | D2 | D2 | D2 |
| 335 | Ar1 | CN | D3 | D3 | D3 |
| 336 | Ar1 | CN | D4 | D4 | D4 |
| 337 | Ar1 | CN | D5 | D5 | D5 |
| 338 | Ar1 | CN | D6 | D6 | D6 |
| 339 | Ar1 | CN | D7 | D7 | D7 |
| 340 | Ar1 | CN | D8 | D8 | D8 |
| 341 | Ar1 | CN | D9 | D9 | D9 |
| 342 | Ar1 | CN | D10 | D10 | D10 |
| 343 | Ar1 | CN | D11 | D11 | D11 |
| 344 | Ar1 | CN | D12 | D12 | D12 |
| 345 | Ar1 | CN | D13 | D13 | D13 |
| 346 | Ar1 | CN | D14 | D14 | D14 |
| 347 | Ar1 | CN | D15 | D15 | D15 |
| 348 | Ar1 | CN | D16 | D16 | D16 |
| 349 | Ar1 | CN | D17 | D17 | D17 |
| 350 | Ar1 | CN | D18 | D18 | D18 |
| 351 | Ar1 | CN | D19 | D19 | D19 |
| 352 | Ar1 | CN | D20 | D20 | D20 |

TABLE 5

| No | R¹ | R² | R³ | R⁴ | R⁵ |
|---|---|---|---|---|---|
| 353 | Ar1 | CN | D21 | D21 | D21 |
| 354 | Ar1 | CN | D22 | D22 | D22 |
| 355 | Ar1 | CN | D23 | D23 | D23 |
| 356 | Ar1 | CN | D24 | D24 | D24 |
| 357 | Ar1 | CN | D25 | D25 | D25 |
| 358 | Ar1 | CN | D26 | D26 | D26 |
| 359 | Ar1 | CN | D27 | D27 | D27 |
| 360 | Ar1 | CN | D28 | D28 | D28 |
| 361 | D1 | Ar1 | CN | D1 | Ar2 |
| 362 | D1 | Ar1 | CN | D1 | Ar3 |
| 363 | D1 | Ar1 | CN | D1 | Ar4 |
| 364 | D1 | Ar1 | CN | D1 | Ar5 |
| 365 | D1 | Ar1 | CN | D1 | Ar6 |
| 366 | D1 | Ar1 | CN | D1 | Ar7 |
| 367 | D1 | Ar1 | CN | D1 | Ar8 |
| 368 | D1 | Ar1 | CN | D1 | Ar9 |
| 369 | D1 | Ar1 | CN | D1 | Ar10 |
| 370 | D1 | Ar1 | CN | D1 | Ar11 |
| 371 | D1 | Ar1 | CN | D1 | Ar12 |
| 372 | D1 | Ar1 | CN | D1 | Ar13 |
| 373 | D1 | Ar1 | CN | D1 | Ar14 |
| 374 | D1 | Ar1 | CN | D1 | Ar15 |
| 375 | D1 | Ar1 | CN | D1 | Ar16 |
| 376 | D1 | Ar1 | CN | D1 | Ar17 |
| 377 | D1 | Ar1 | CN | D1 | Ar18 |
| 378 | D1 | Ar1 | CN | D1 | Ar19 |
| 379 | D1 | Ar1 | CN | D1 | Ar20 |
| 380 | D1 | Ar1 | CN | D1 | Ar21 |
| 381 | D1 | Ar1 | CN | D1 | Ar22 |
| 382 | D1 | Ar1 | CN | D1 | Ar23 |
| 383 | D1 | Ar1 | CN | D1 | Ar24 |
| 384 | D1 | Ar1 | CN | D1 | Ar25 |
| 385 | D1 | Ar1 | CN | D1 | Ar26 |
| 386 | D1 | Ar1 | CN | D1 | Ar27 |
| 387 | D1 | Ar1 | CN | D1 | Ar28 |
| 388 | D1 | Ar1 | CN | D1 | Ar29 |
| 389 | D1 | Ar1 | CN | D1 | Ar30 |
| 390 | D1 | Ar1 | CN | D1 | Ar31 |
| 391 | D1 | Ar1 | CN | D1 | Ar32 |
| 392 | D1 | Ar1 | CN | D1 | Ar33 |
| 393 | D1 | Ar1 | CN | D2 | Ar1 |
| 394 | D1 | Ar1 | CN | D3 | Ar1 |
| 395 | D1 | Ar1 | CN | D4 | Ar1 |
| 396 | D1 | Ar1 | CN | D5 | Ar1 |
| 397 | D1 | Ar1 | CN | D6 | Ar1 |
| 398 | D1 | Ar1 | CN | D7 | Ar1 |
| 399 | D1 | Ar1 | CN | D8 | Ar1 |
| 400 | D1 | Ar1 | CN | D9 | Ar1 |
| 401 | D1 | Ar1 | CN | D10 | Ar1 |
| 402 | D1 | Ar1 | CN | D11 | Ar1 |
| 403 | D1 | Ar1 | CN | D12 | Ar1 |
| 404 | D1 | Ar1 | CN | D13 | Ar1 |
| 405 | D1 | Ar1 | CN | D14 | Ar1 |
| 406 | D1 | Ar1 | CN | D15 | Ar1 |
| 407 | D1 | Ar1 | CN | D16 | Ar1 |
| 408 | D1 | Ar1 | CN | D17 | Ar1 |
| 409 | D1 | Ar1 | CN | D18 | Ar1 |
| 410 | D1 | Ar1 | CN | D19 | Ar1 |
| 411 | D1 | Ar1 | CN | D20 | Ar1 |
| 412 | D1 | Ar1 | CN | D21 | Ar1 |
| 413 | D1 | Ar1 | CN | D22 | Ar1 |
| 414 | D1 | Ar1 | CN | D23 | Ar1 |
| 415 | D1 | Ar1 | CN | D24 | Ar1 |
| 416 | D1 | Ar1 | CN | D25 | Ar1 |
| 417 | D1 | Ar1 | CN | D26 | Ar1 |
| 418 | D1 | Ar1 | CN | D27 | Ar1 |

TABLE 5-continued

| No | $R^1$ | $R^2$ | $R^3$ | $R^4$ | $R^5$ |
|---|---|---|---|---|---|
| 419 | D1 | Ar1 | CN | D28 | Ar1 |
| 420 | D7 | Ar1 | CN | D8 | Ar1 |
| 421 | D7 | Ar1 | CN | D9 | Ar1 |
| 422 | D7 | Ar1 | CN | D10 | Ar1 |
| 423 | D7 | Ar1 | CN | D11 | Ar1 |
| 424 | D7 | Ar1 | CN | D12 | Ar1 |
| 425 | D13 | Ar1 | CN | D14 | Ar1 |
| 426 | D13 | Ar1 | CN | D15 | Ar1 |
| 427 | D13 | Ar1 | CN | D16 | Ar1 |
| 428 | D13 | Ar1 | CN | D17 | Ar1 |
| 429 | D13 | Ar1 | CN | D18 | Ar1 |
| 430 | D13 | Ar1 | CN | D19 | Ar1 |
| 431 | D13 | Ar1 | CN | D20 | Ar1 |
| 432 | D17 | Ar1 | CN | D18 | Ar1 |
| 433 | D17 | Ar1 | CN | D19 | Ar1 |
| 434 | D17 | Ar1 | CN | D20 | Ar1 |

The molecular weight of the compound represented by the general formula (1) is, for example, in the case where an organic layer containing the compound represented by the general formula (1) is intended to be formed according to a vapor deposition method and used in devices, preferably 1500 or less, more preferably 1200 or less, even more preferably 1000 or less, and further more preferably 900 or less. The lower limit of the molecular weight is the smallest molecular weight that the general formula (1) can take.

Irrespective of the molecular weight thereof, the compound represented by the general formula (1) may be formed into a film according to a coating method. When a coating method is employed, even a compound having a relatively large molecular weight can be formed into a film. The compound represented by the general formula (1) has an advantage that, among cyanobenzene compounds, it can readily dissolve in an organic solvent. Consequently, the compound represented by the general formula (1) is applicable to a coating method and, in addition, it can be readily purified to have an increased purity.

Applying the present invention, it is considered to use a compound containing plural structures represented by the general formula (1) in the molecule as a light-emitting material.

For example, it is considered that a polymerizable group is previously introduced into a structure represented by the general formula (1) and the polymerizable group is polymerized to give a polymer, and the polymer is used as a light-emitting material. Specifically, a monomer containing a polymerizable functional group in any of $R^1$ to $R^5$ in the general formula (1) is prepared, and this is homo-polymerized or copolymerized with any other monomer to give a polymer having a recurring unit, and the polymer can be used as a material for a light-emitting material. Alternatively, compounds each having a structure represented by the general formula (1) are coupled to give a dimer or a trimer, and it can be used as a light-emitting material.

Examples of the polymer having a recurring unit containing a structure represented by the general formula (1) include polymers containing a structure represented by the following general formula (3) or (4).

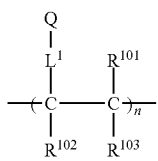

General Formula (3)

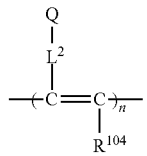

General Formula (4)

In the general formula (3) or (4), Q represents a group containing a structure represented by the general formula (1), and $L^1$ and $L^2$ each represent a linking group. The carbon number of the linking group is preferably 0 to 20, more preferably 1 to 15, even more preferably 2 to 10. Preferably, the linking group has a structure represented by —$X^{11}$-$L^{11}$-. Here, $X^{11}$ represents an oxygen atom or a sulfur atom and is preferably an oxygen atom. $L^{11}$ represents a linking group, and is preferably a substituted or unsubstituted alkylene group, or a substituted or unsubstituted arylene group, more preferably a substituted or unsubstituted alkylene group having 1 to 10 carbon atoms, or a substituted or unsubstituted phenylene group.

In the general formula (3) or (4), $R^{101}$, $R^{102}$, $R^{103}$ and $R^{104}$ each independently represent a substituent. Preferably, the substituent is a substituted or unsubstituted alkyl group having 1 to 6 carbon atoms, a substituted or unsubstituted alkoxy group having 1 to 6 carbon atoms, or a halogen atom, more preferably an unsubstituted alkyl group having 1 to 3 carbon atoms, an unsubstituted alkoxy group having 1 to 3 carbon atoms, a fluorine atom, or a chlorine atom, and even more preferably an unsubstituted alkyl group having 1 to 3 carbon atoms, or an unsubstituted alkoxy group having 1 to 3 carbon atoms.

The linking group represented by $L^1$ and $L^2$ may bond to any of $R^1$ to $R^5$ in the structure of the general formula (1) constituting Q. Two or more linking groups may bond to one Q to form a crosslinked structure or a network structure.

Specific examples of the structure of the recurring unit include structures represented by the following general formulae (5) to (8).

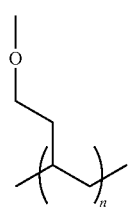

Formula (5)

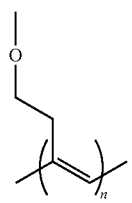

Formula (6)

-continued

Formula (7)

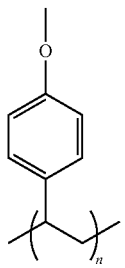

Formula (8)

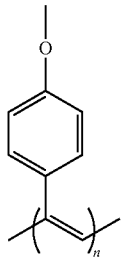

The polymer having the recurring unit containing the structure represented by any of the general formulae (5) to (8) may be synthesized in such a manner that a hydroxyl group is introduced to any of $R^1$ to $R^5$ in the structure represented by the general formula (1), and the hydroxyl group as a linker is reacted with the following compound to introduce a polymerizable group thereinto, followed by polymerizing the polymerizable group.

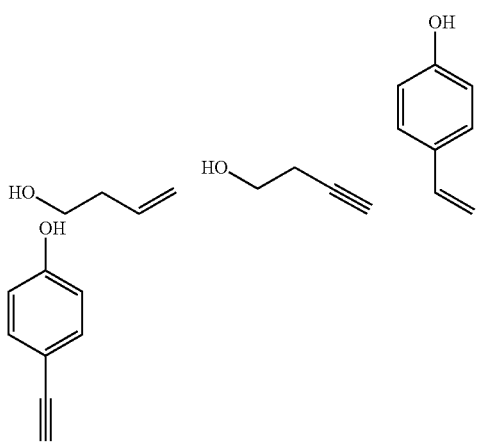

The polymer containing the structure represented by the general formula (1) in the molecule may be a polymer containing only a recurring unit having the structure represented by the general formula (1), or a polymer further containing a recurring unit having another structure. The recurring unit having the structure represented by the general formula (1) contained in the polymer may be only one kind or two or more kinds. Examples of the recurring unit that does not have the structure represented by the general formula (1) include a recurring unit derived from a monomer that is used for ordinary copolymerization. Examples of the recurring unit include a recurring unit derived from a monomer having an ethylenic unsaturated bond, such as ethylene and styrene.

[Synthesis Method for Compound Represented by General Formula (1)]

The compound represented by the general formula (1) is a novel compound.

The compound represented by the general formula (1) can be synthesized by combining known reactions. For example, a tetrahalogenodicyanobenzene is used as a starting substance, and is reacted with a carbazole in the presence of NaH to give a dicyanobenzene derivative having a donor group of a carbazolyl group introduced thereinto in place of a part of halogen atoms. The resultant dicyanobenzene derivative is reacted with a tributylphenyl stannane in the presence of a catalyst to thereby substitute the halogen atom with a phenyl group to give a dicyanobenzene derivative having a carbazolyl group and a phenyl group and represented by the general formula (1). Regarding the specific conditions for the reaction and the reaction scheme, Synthesis Examples to be given hereinunder may be referred to. The other compounds represented by the general formula (1) can be synthesized using the same process or a known synthesis method.

[Organic Light-Emitting Device]

The compound represented by the general formula (1) of the present invention is useful as a light-emitting material for organic light-emitting devices. Accordingly, the compound represented by the general formula (1) of the present invention can be effectively used as a light-emitting material in a light-emitting layer of an organic light-emitting device. In addition, the compound represented by the general formula (1) of the present invention can also be used as a host or assist dopant.

The compound represented by the general formula (1) include a delayed fluorescent material that emits delayed fluorescence. Specifically, the present invention includes an invention of a delayed fluorescent material having a structure represented by the general formula (1), an invention of using the compound represented by the general formula (1) as a delayed fluorescent material, and an invention of a method of using the compound represented by the general formula (1) for emitting delayed fluorescence. An organic light-emitting device using such a compound as a light-emitting material is characterized that it emits delayed fluorescence and has a high emission efficiency. The principle will be described below with reference to an organic electroluminescent device taken as an example.

In an organic electroluminescent device, carriers are injected from an anode and a cathode to a light-emitting material to form an excited state for the light-emitting material, with which light is emitted. In the case of a carrier injection type organic electroluminescent device, in general, excitons that are excited to the excited singlet state are 25% of the total excitons generated, and the remaining 75% thereof are excited to the excited triplet state. Accordingly, the use of phosphorescence, which is light emission from the excited triplet state, provides a high energy utilization. However, the excited triplet state has a long lifetime and thus causes saturation of the excited state and deactivation of energy through mutual action with the excitons in the excited triplet state, and therefore the quantum yield of phosphorescence may generally be often not high. A delayed fluorescent material emits fluorescent light through the mechanism that the energy of excitons transits to the excited triplet state through intersystem crossing or the like, and then transits to the excited singlet state through reverse intersystem crossing due to triplet-triplet annihilation or absorption of thermal energy, thereby emitting fluorescent light. It is considered that among the materials, a thermal activation type delayed fluorescent material emitting light through absorption of thermal energy is particularly useful for an organic electroluminescent device. In the case where a delayed fluorescent material is used in an organic electroluminescent device, the excitons in the excited singlet state normally emit fluorescent light. On the other hand, the excitons in the excited triplet state emit fluorescent light through intersystem crossing to the excited singlet state by absorbing the heat generated by the device. At this time, the light emitted through reverse intersystem crossing from the excited triplet state to the excited singlet state has the same wavelength as fluorescent light since it is light emission from the excited singlet state, but has a longer lifetime (light emission lifetime) than the normal fluorescent light, and thus the light is observed as fluorescent light that is delayed from the normal fluorescent light. The light may be defined as delayed fluorescent light. The use of the thermal activation type reverse intersystem crossing mechanism may raise the proportion of the compound in the excited singlet state, which is generally formed in a proportion only of 25%, to 25% or more through the absorption of the thermal energy after the carrier injection. A compound that emits strong fluorescent light and delayed fluorescent light at a low temperature of lower than 100° C. undergoes the intersystem crossing from the excited triplet state to the excited singlet state sufficiently with the heat of the device, thereby emitting delayed fluorescent light, and thus the use of the compound may drastically enhance the light emission efficiency.

Using the compound represented by the general formula (1) of the present invention as a light-emitting material in a light-emitting layer, excellent organic light-emitting devices such as an organic photoluminescent device (organic PL device) and an organic electroluminescent device (organic EL device) can be provided. An organic photoluminescent device has a structure where at least a light-emitting layer is formed on a substrate. An organic electroluminescent device has a structure including at least an anode, a cathode and an organic layer formed between the anode and the cathode. The organic layer contains at least a light-emitting layer, and may be formed of a light-emitting layer alone, or may has one or more other organic layers in addition to a light-emitting layer. The other organic layers include a hole transport layer, a hole injection layer, an electron blocking layer, a hole blocking layer, an electron injection layer, an electron transport layer, and an exciton blocking layer. The hole transport layer may be a hole injection transport layer having a hole injection function, and the electron transport layer may be an electron injection transport layer having an electron injection function. A configuration example of an organic electroluminescent device is shown in FIG. 1. In FIG. 1, 1 is a substrate, 2 is an anode, 3 is a hole injection layer, 4 is a hole transport layer, 5 is a light-emitting layer, 6 is an electron transport layer, and 7 is a cathode.

In the following, the constituent members and the layers of the organic electroluminescent device are described. The description of the substrate and the light-emitting layer given below may apply to the substrate and the light-emitting layer of an organic photoluminescent device.

(Substrate)

The organic electroluminescent device of the invention is preferably supported by a substrate. The substrate is not particularly limited and may be those that have been commonly used in an organic electroluminescent device, and examples thereof used include those formed of glass, transparent plastics, quartz and silicon.

(Anode)

The anode of the organic electroluminescent device used is preferably formed of, as an electrode material, a metal, an alloy, or an electroconductive compound each having a large work function (4 eV or more), or a mixture thereof. Specific examples of the electrode material include a metal, such as Au, and an electroconductive transparent material, such as CuI, indium tin oxide (ITO), $SnO_2$ and ZnO. A material that is amorphous and is capable of forming a transparent electroconductive film, such as IDIXO ($In_2O_3$—ZnO), may also be used. The anode may be formed in such a manner that the electrode material is formed into a thin film by such a method as vapor deposition or sputtering, and the film is patterned into a desired pattern by a photolithography method, or in the case where the pattern may not require high accuracy (for example, approximately 100 μm or more), the pattern may be formed with a mask having a desired shape on vapor deposition or sputtering of the electrode material. In alternative, in the case where a material capable of being coated, such as an organic electroconductive compound, is used, a wet film forming method, such as a printing method and a coating method, may be used. In the case where emitted light is to be taken out through the anode, the anode preferably has a transmittance of more than 10%, and the anode preferably has a sheet resistance of several hundred Ω/sq (ohm per square) or less. The thickness of the anode may be generally selected from a range of from 10 to 1,000 nm, and preferably from 10 to 200 nm, while depending on the material used.

(Cathode)

The cathode is preferably formed of as an electrode material a metal (which is referred to as an electron injection metal), an alloy, or an electroconductive compound, having a small work function (4 eV or less), or a mixture thereof. Specific examples of the electrode material include sodium, a sodium-potassium alloy, magnesium, lithium, a magnesium-cupper mixture, a magnesium-silver mixture, a magnesium-aluminum mixture, a magnesium-indium mixture, an aluminum-aluminum oxide ($Al_2O_3$) mixture, indium, a lithium-aluminum mixture, and a rare earth metal. Among these, a mixture of an electron injection metal and a second metal that is a stable metal having a larger work function than the electron injection metal, for example, a magnesium-silver mixture, a magnesium-aluminum mixture, a magnesium-indium mixture, an aluminum-aluminum oxide ($Al_2O_3$) mixture, a lithium-aluminum mixture, and aluminum, is preferred from the standpoint of the electron injection property and the durability against oxidation and the like. The cathode may be produced by forming the electrode material into a thin film by such a method as vapor deposition or sputtering. The cathode preferably has a sheet resistance of several hundred Ω/sq (ohm per square) or less, and the thickness thereof may be generally selected from a range of from 10 nm to 5 μm, and preferably from 50 to 200 nm. For transmitting the emitted light, any one of the anode and the cathode of the organic electroluminescent device is preferably transparent or translucent, thereby enhancing the light emission luminance.

The cathode may be formed with the electroconductive transparent materials described for the anode, thereby forming a transparent or translucent cathode, and by applying the cathode, a device having an anode and a cathode, both of which have transmittance, may be produced.

(Light-Emitting Layer)

The light-emitting layer is a layer in which holes and electrons injected from an anode and a cathode are recombined to give excitons for light emission. A light-emitting material may be used singly in the light-emitting layer, but preferably, the layer contains a light-emitting material and a host material. As the light-emitting material, one or more selected from a group of the compounds of the present invention represented by the general formula (1) can be used. In order that the organic electroluminescent device and the organic photoluminescent device of the present invention can express a high light emission efficiency, it is important to confine the singlet exciton and the triplet exciton formed in the light-emitting material to the light-emitting material. Accordingly, preferably, a host material is used in addition to the light-emitting material in the light-emitting layer. As the host material, an organic compound, of which at least any one of the excited singlet energy and the excited triplet energy is higher than that of the light-emitting material of the present invention, may be used. As a result, the singlet exciton and the triplet exciton formed in the light-emitting material of the present invention can be confined to the molecule of the light-emitting material of the present invention to sufficiently derive the light emission efficiency thereof. Needless-to-say, there may be a case where a high light emission efficiency could be attained even though the singlet exciton and the triplet exciton could not be sufficiently confined, and therefore, any host material capable of realizing a high light emission efficiency can be used in the present invention with no specific limitation. In the organic light-emitting device or the organic electroluminescent device of the present invention, light emission occurs from the light-emitting material of the present invention contained in the light-emitting layer. The light emission contains both of fluorescent emission and delayed fluorescent emission. In addition, a part of light emission may be partially from a host material.

The content of the compound represented by the general formula (1) in the light-emitting layer is preferably less than 50% by weight. Further, the upper limit of the content of the compound represented by the general formula (1) is preferably less than 30% by weight, and the upper limit of the content may be, for example, less than 20% by weight, less than 10% by weight, less than 5% by weight, less than 3% by weight, less than 1% by weight, or less than 0.5% by weight. Preferably, the lower limit is 0.001% by weight or more, and may be, for example, more than 0.01% by weight, more than 0.1% by weight, more than 0.5% by weight, or more than 1% by weight.

The host material in the light-emitting layer is preferably an organic compound having hole transport competence and electron transport competence, capable of preventing prolongation of emission wavelength and having a high glass transition temperature.

The compound represented by the general formula (1) can be used as a host material in the light-emitting layer.

(Injection Layer)

The injection layer is a layer that is provided between the electrode and the organic layer, for decreasing the driving voltage and enhancing the light emission luminance, and includes a hole injection layer and an electron injection layer, which may be provided between the anode and the light-emitting layer or the hole transport layer and between the cathode and the light emitting layer or the electron transport layer. The injection layer may be provided depending on necessity.

(Blocking Layer)

The blocking layer is a layer that is capable of inhibiting charges (electrons or holes) and/or excitons present in the light-emitting layer from being diffused outside the light-emitting layer. The electron blocking layer may be disposed between the light-emitting layer and the hole transport layer, and inhibits electrons from passing through the light-emitting layer toward the hole transport layer. Similarly, the hole blocking layer may be disposed between the light-emitting layer and the electron transport layer, and inhibits holes from passing through the light-emitting layer toward the electron transport layer. The blocking layer may also be used for inhibiting excitons from being diffused outside the light-emitting layer. Thus, the electron blocking layer and the hole blocking layer each may also have a function as an exciton blocking layer. The term "the electron blocking layer" or "the exciton blocking layer" referred to herein is intended to include a layer that has both the functions of an electron blocking layer and an exciton blocking layer by one layer.

(Hole Blocking Layer)

The hole blocking layer has the function of an electron transport layer in a broad sense. The hole blocking layer has a function of inhibiting holes from reaching the electron transport layer while transporting electrons, and thereby enhances the recombination probability of electrons and holes in the light-emitting layer. As the material for the hole blocking layer, the material for the electron transport layer to be mentioned below may be used optionally.

(Electron Blocking Layer)

The electron blocking layer has the function of transporting holes in a broad sense. The electron blocking layer has a function of inhibiting electrons from reaching the hole transport layer while transporting holes, and thereby enhances the recombination probability of electrons and holes in the light-emitting layer.

(Exciton Blocking Layer)

The exciton blocking layer is a layer for inhibiting excitons generated through recombination of holes and electrons in the light-emitting layer from being diffused to the charge transporting layer, and the use of the layer inserted enables effective confinement of excitons in the light-emitting layer, and thereby enhances the light emission efficiency of the device. The exciton blocking layer may be inserted adjacent to the light-emitting layer on any of the side of the anode and the side of the cathode, and on both the sides. Specifically, in the case where the exciton blocking layer is present on the side of the anode, the layer may be inserted between the hole transport layer and the light-emitting layer and adjacent to the light-emitting layer, and in the case where the layer is inserted on the side of the cathode, the layer may be inserted between the light-emitting layer and the cathode and adjacent to the light-emitting layer. Between the anode and the exciton blocking layer that is adjacent to the light-emitting layer on the side of the anode, a hole injection layer, an electron blocking layer and the like may be provided, and between the cathode and the exciton blocking layer that is adjacent to the light-emitting layer on the side of the cathode, an electron injection layer, an electron transport layer, a hole blocking layer and the like may be provided. In the case where the blocking layer is provided, preferably, at least one of the excited singlet energy and the excited triplet energy of the material used as the blocking layer is higher than the excited singlet energy and the excited triplet energy of the light-emitting layer, respectively, of the light-emitting material.

(Hole Transport Layer)

The hole transport layer is formed of a hole transport material having a function of transporting holes, and the hole transport layer may be provided as a single layer or plural layers.

The hole transport material has one of injection or transporting property of holes and blocking property of electrons, and may be any of an organic material and an inorganic material. Examples of known hole transport materials that may be used herein include a triazole derivative, an oxadiazole derivative, an imidazole derivative, a carbazole derivative, an indolocarbazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline copolymer and an electroconductive polymer oligomer, particularly a thiophene oligomer. Among these, a porphyrin compound, an aromatic tertiary amine compound and a styrylamine compound are preferably used, and an aromatic tertiary amine compound is more preferably used.

(Electron Transport Layer)

The electron transport layer is formed of a material having a function of transporting electrons, and the electron transport layer may be a single layer or may be formed of plural layers.

The electron transport material (often also acting as a hole blocking material) may have a function of transmitting the electrons injected from a cathode to a light-emitting layer. The electron transport layer usable here includes, for example, nitro-substituted fluorene derivatives, diphenylquinone derivatives, thiopyran dioxide derivatives, carbodiimides, fluorenylidenemethane derivatives, anthraquinodimethane and anthrone derivatives, oxadiazole derivatives, etc. Further, thiadiazole derivatives derived from the above-mentioned oxadiazole derivatives by substituting the oxygen atom in the oxadiazole ring with a sulfur atom, and quinoxaline derivatives having a quinoxaline ring known as an electron-attractive group are also usable as the electron transport material. Further, polymer materials prepared by introducing these materials into the polymer chain, or having these material in the polymer main chain are also usable.

In producing the organic electroluminescent device, the compound represented by the general formula (1) may be used not only in one organic layer (for example, an electron transport layer) but also in multiple organic layers. In so doing, the compounds represented by the general formula (1) used in different organic layers may be the same as or different from each other. For example, the compound represented by the general formula (1) may be used in the above-mentioned injection layer, the blocking layer, the hole blocking layer, the electron blocking layer, the exciton blocking layer and the hole transport layer, in addition to the electron transport layer and the light-emitting layer. The method for forming these layers is not specifically limited, and the layers may be formed according to any of a dry process or a wet process.

Preferred materials for use for the organic electroluminescent device are concretely exemplified below. However, the materials for use in the present invention are not limitatively interpreted by the following exemplary compounds. Compounds, even though exemplified as materials having a specific function, can also be used as other materials having any other function.

First, preferred compounds for use as a host material in a light-emitting layer are mentioned below.

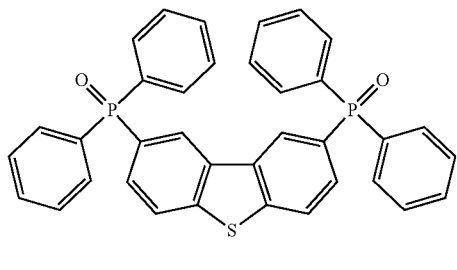 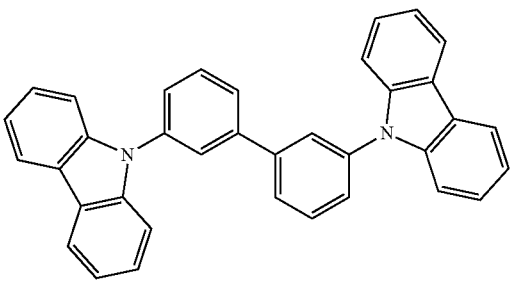

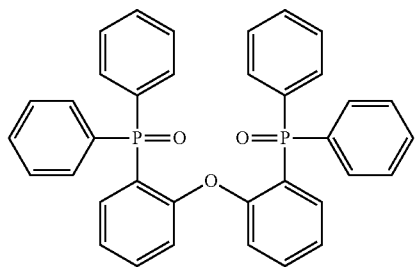

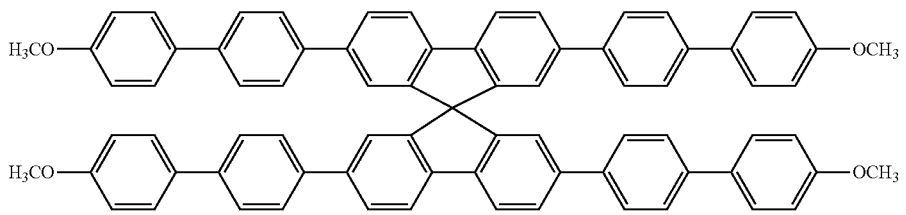

-continued
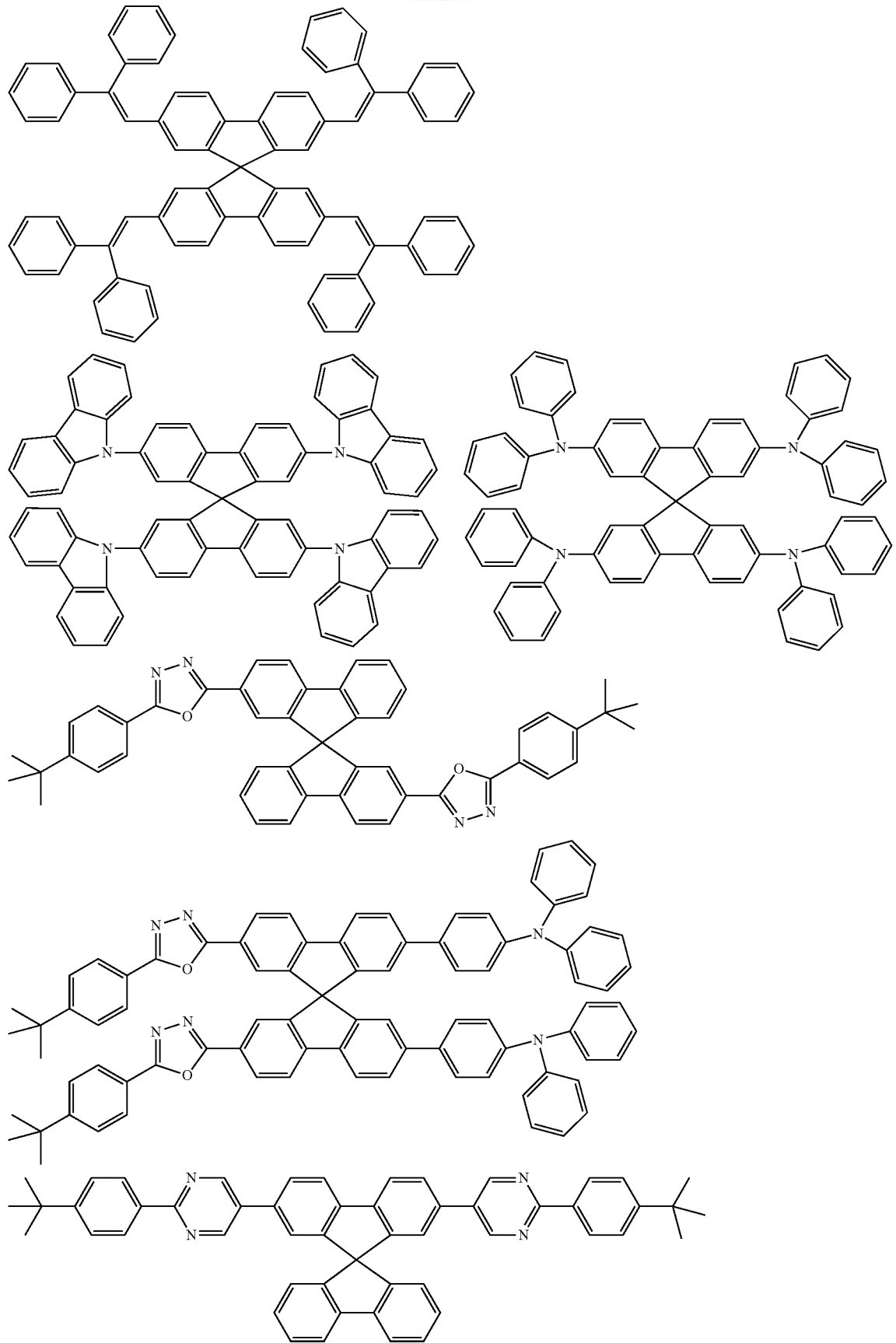

-continued
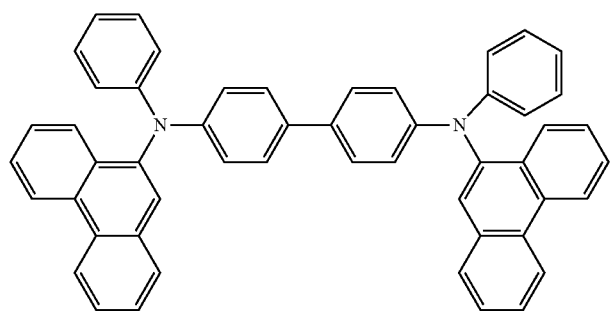
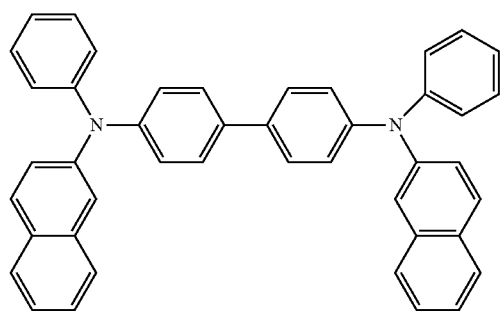
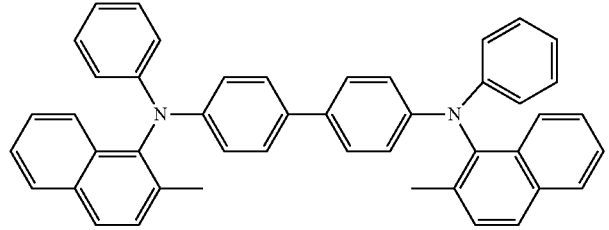
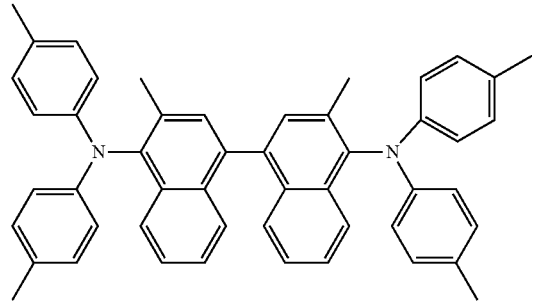
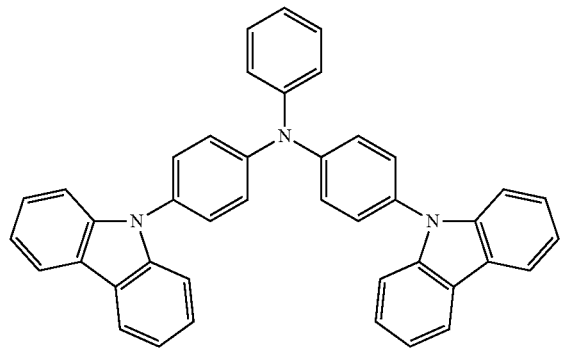
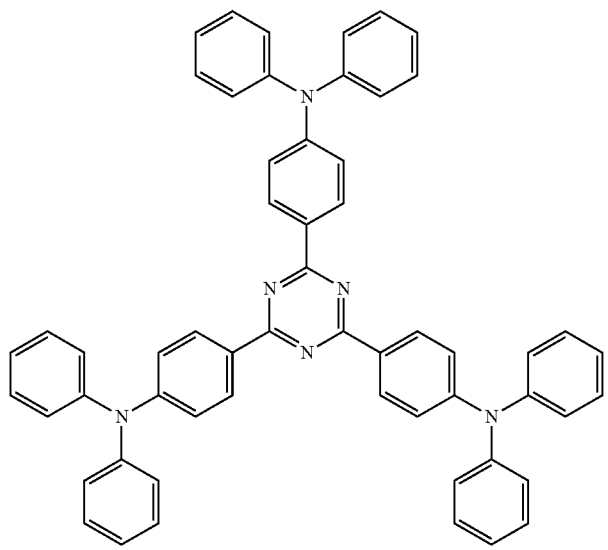
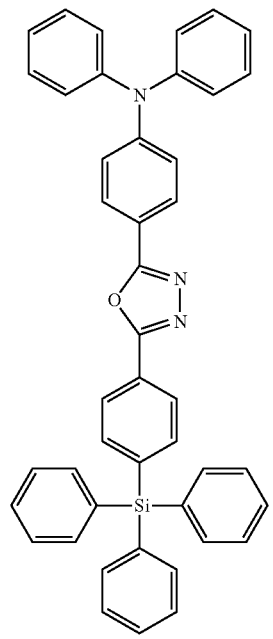

-continued
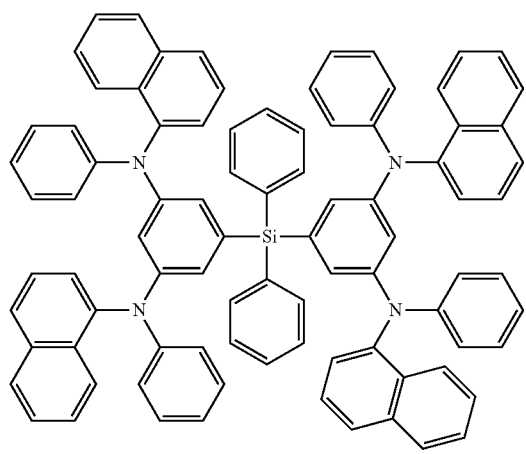
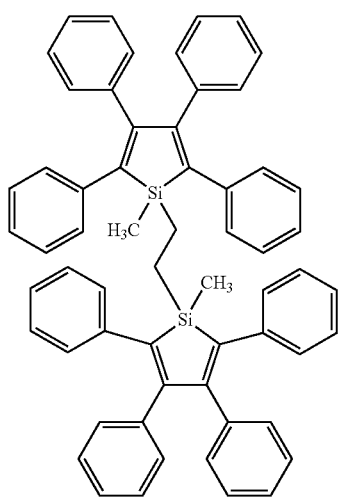
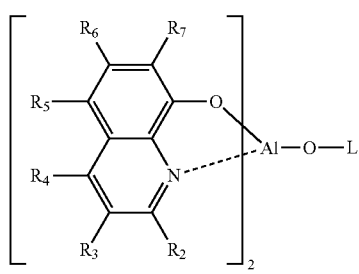
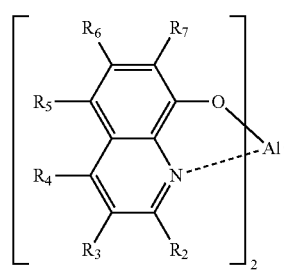
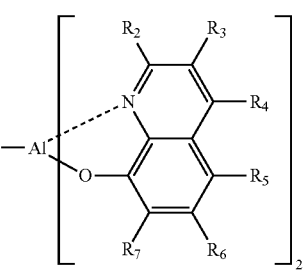
$R_2$-$R_7$ = H or substituent
L = ligand
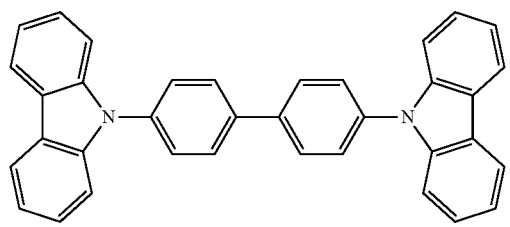
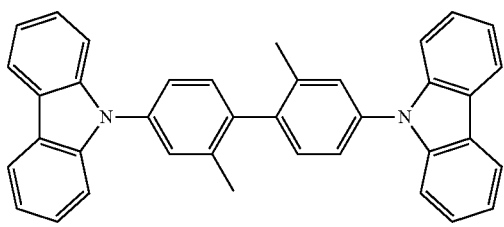
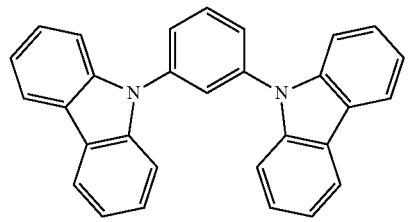
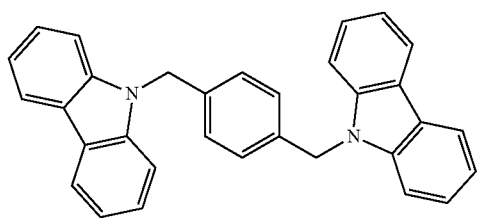
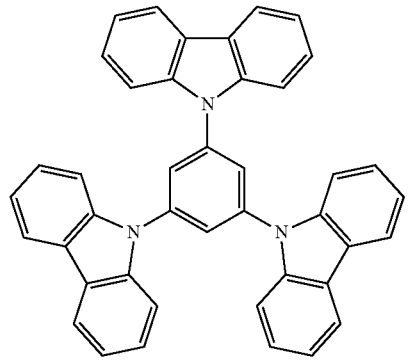
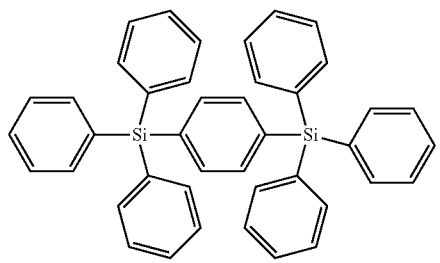

-continued
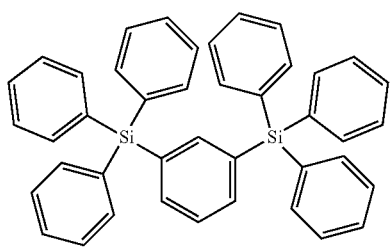
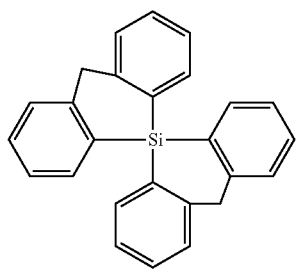
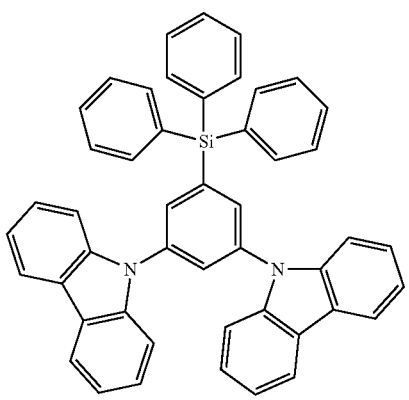
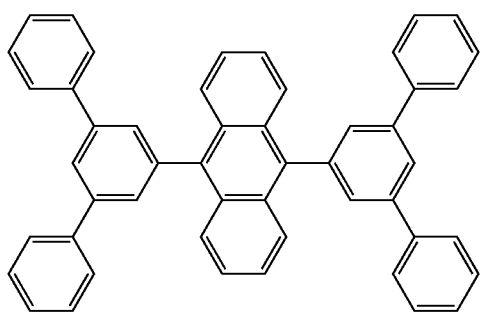
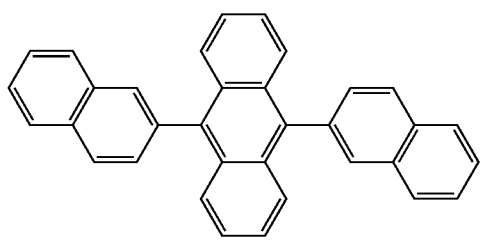
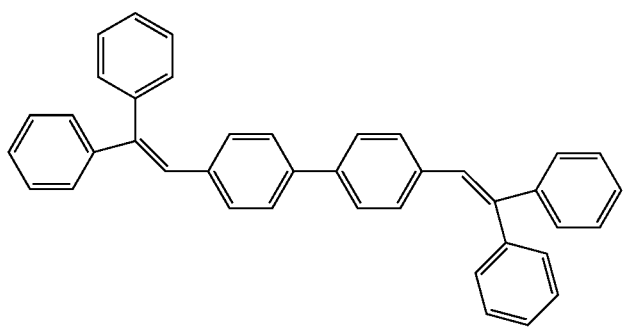
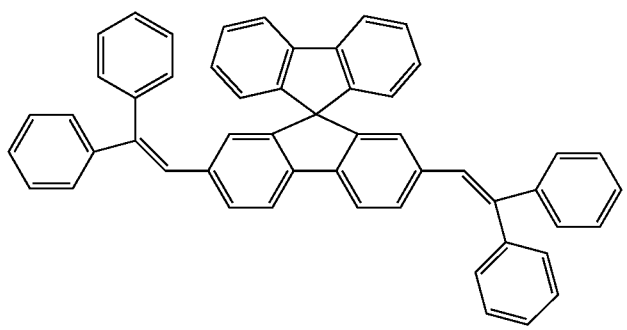

-continued
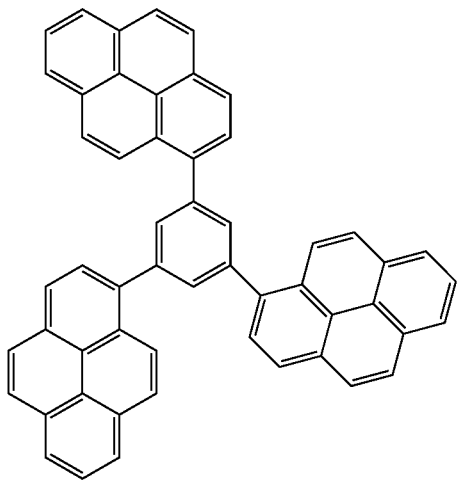
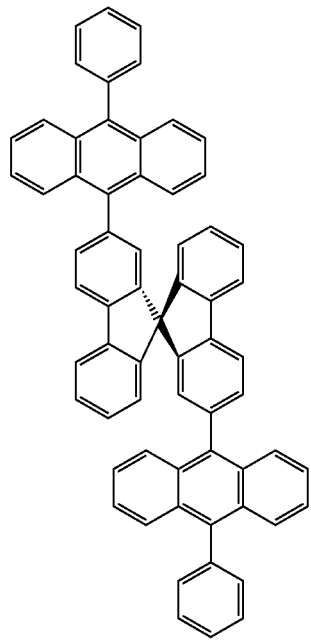
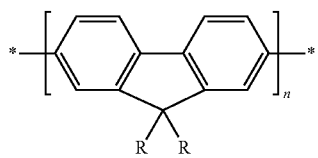
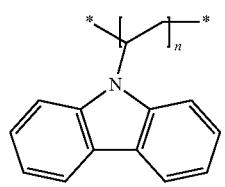
R = alkyl, aryl
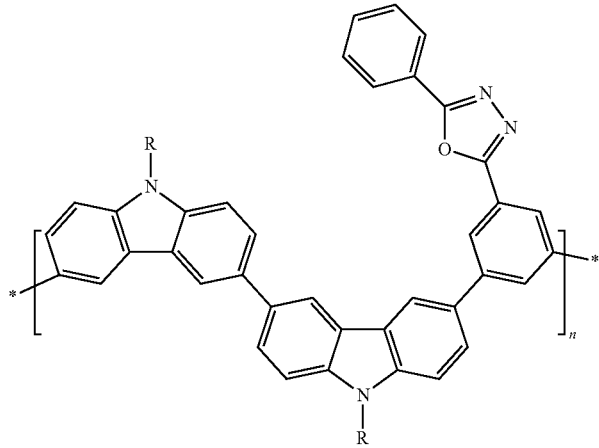
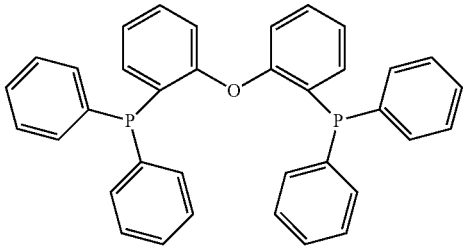
R = alkyl, aryl
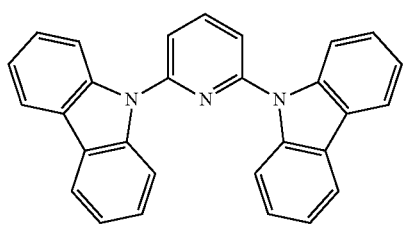

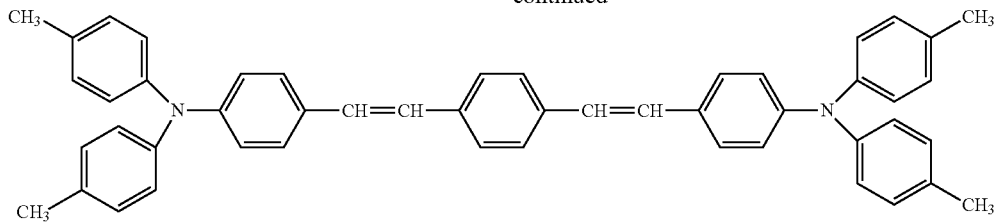
Next, preferred compounds for use as a hole injection material are mentioned below.
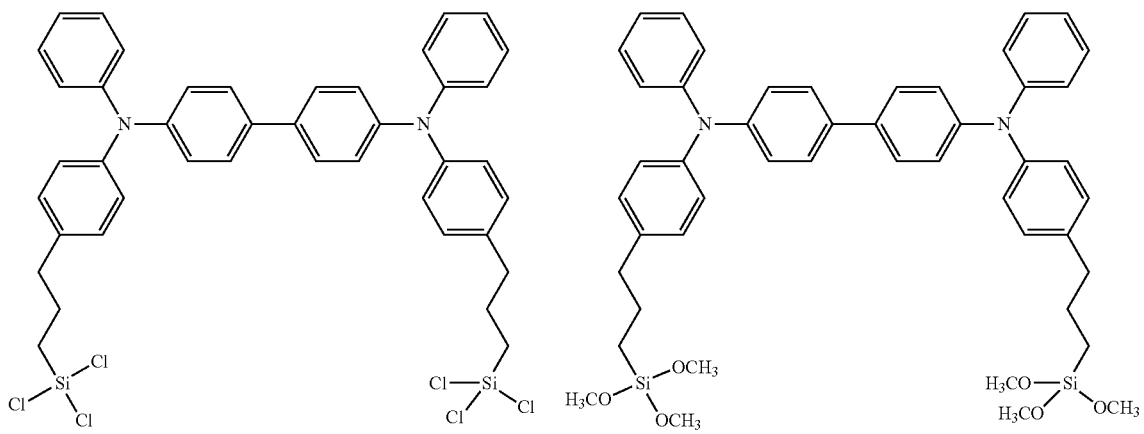
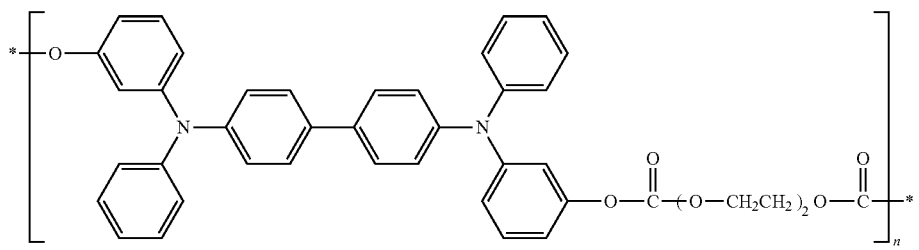
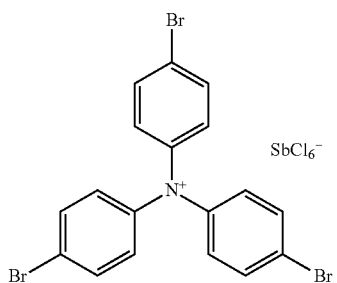

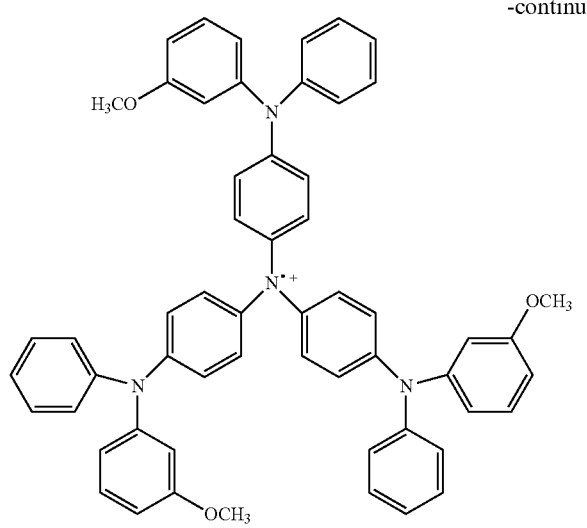
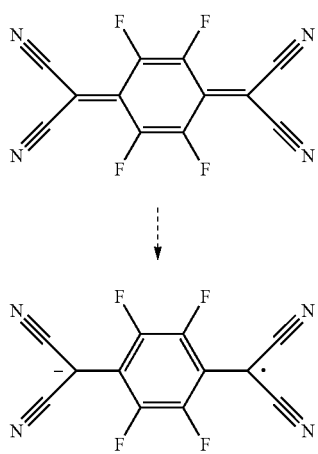
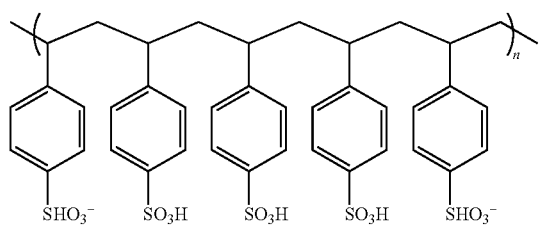
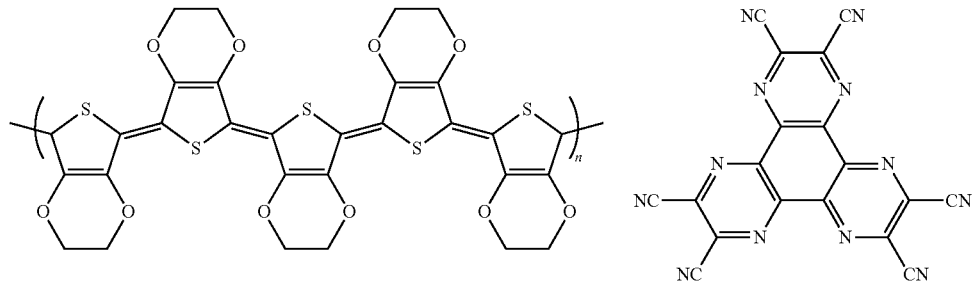
Next, preferred compounds for use as a hole transport material are mentioned below.
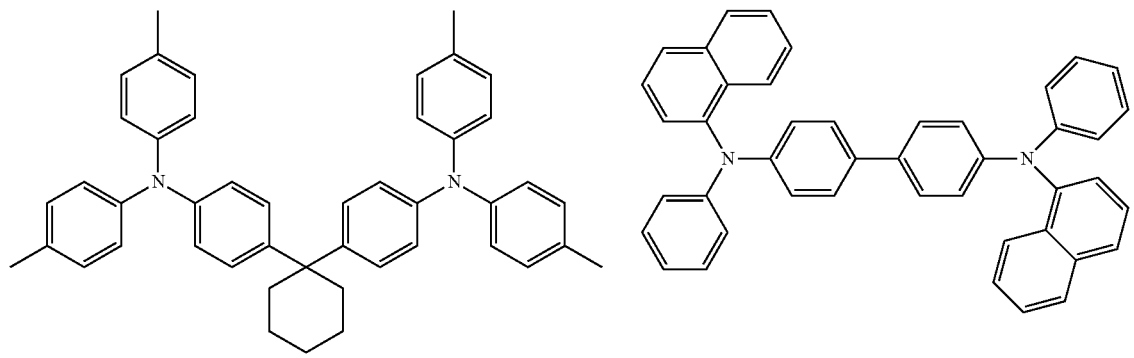

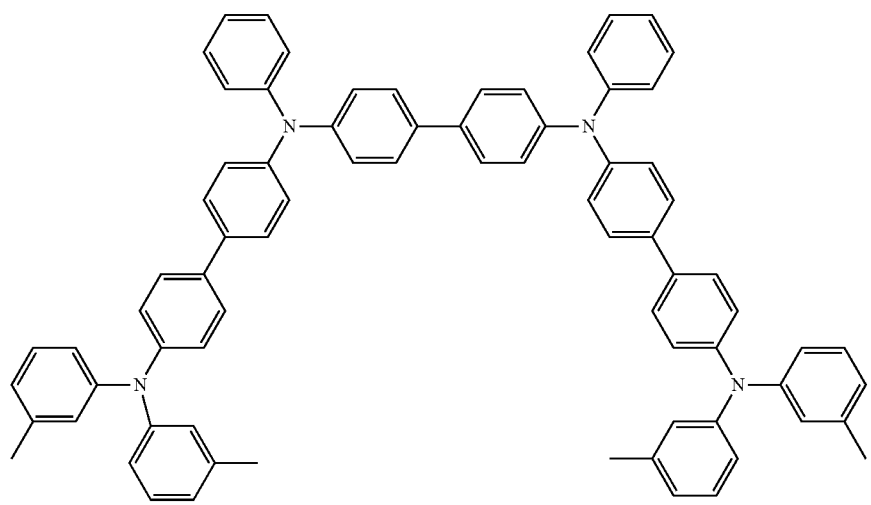
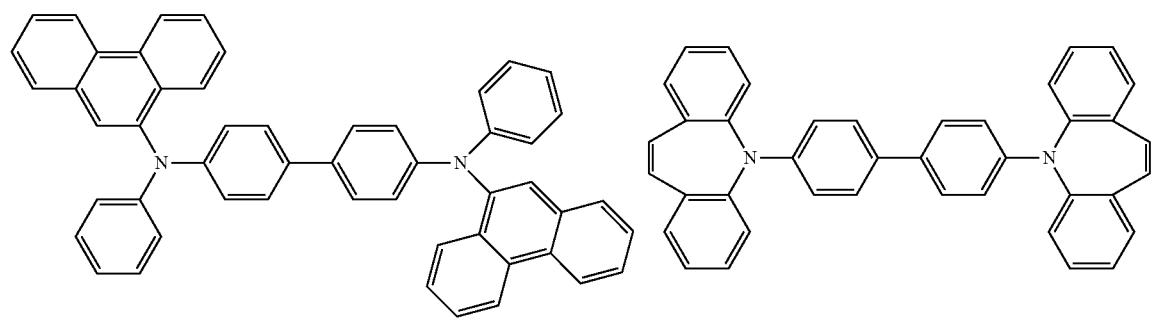
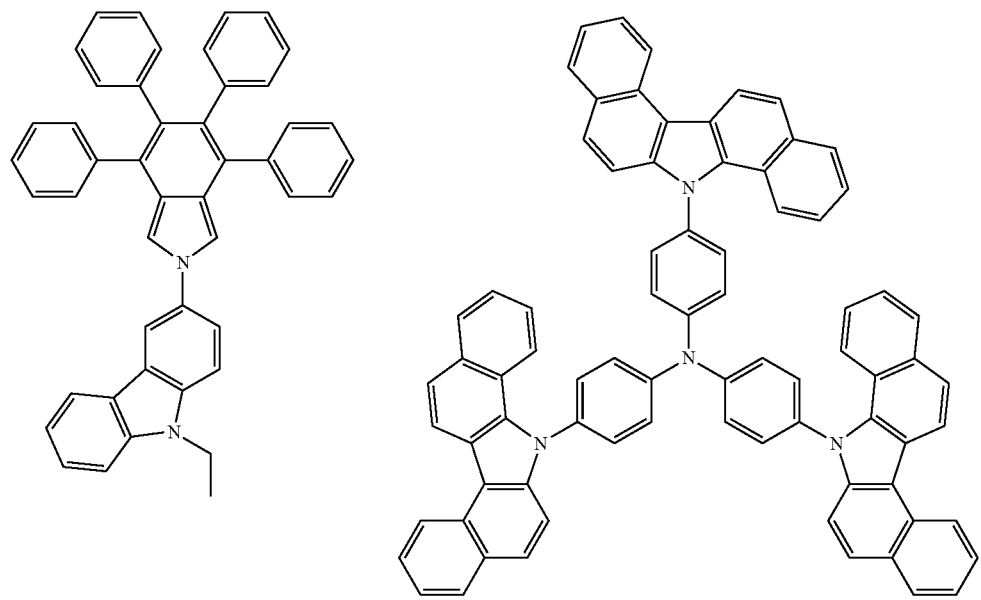

-continued
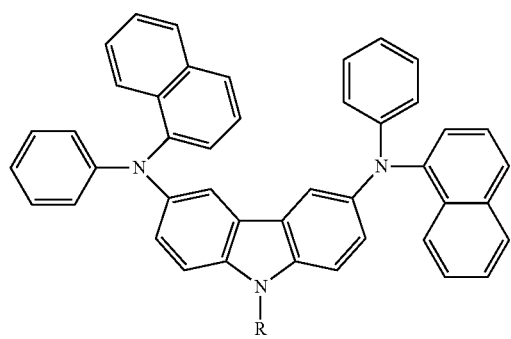
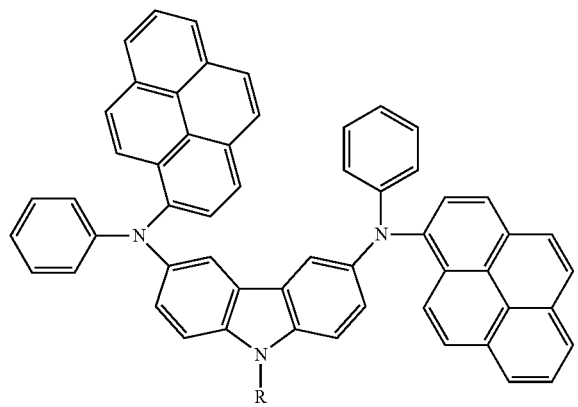
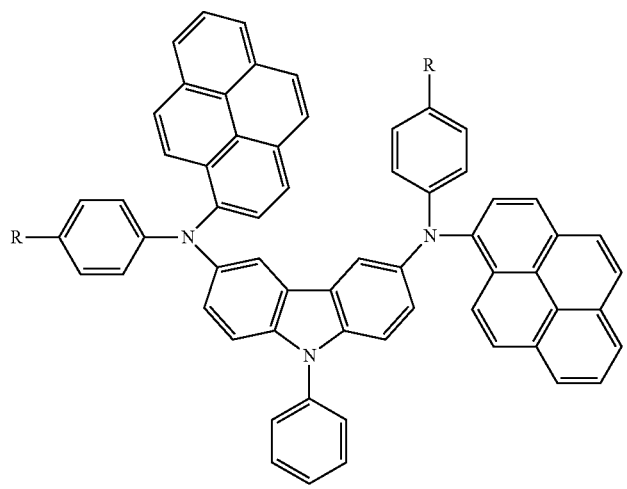
R = alkyl, aryl, alkoxy, aryloxy,
9,9'-dialkylfluorene
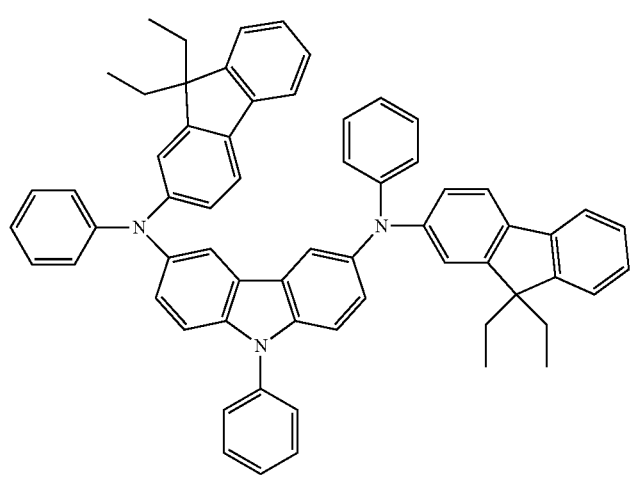

-continued
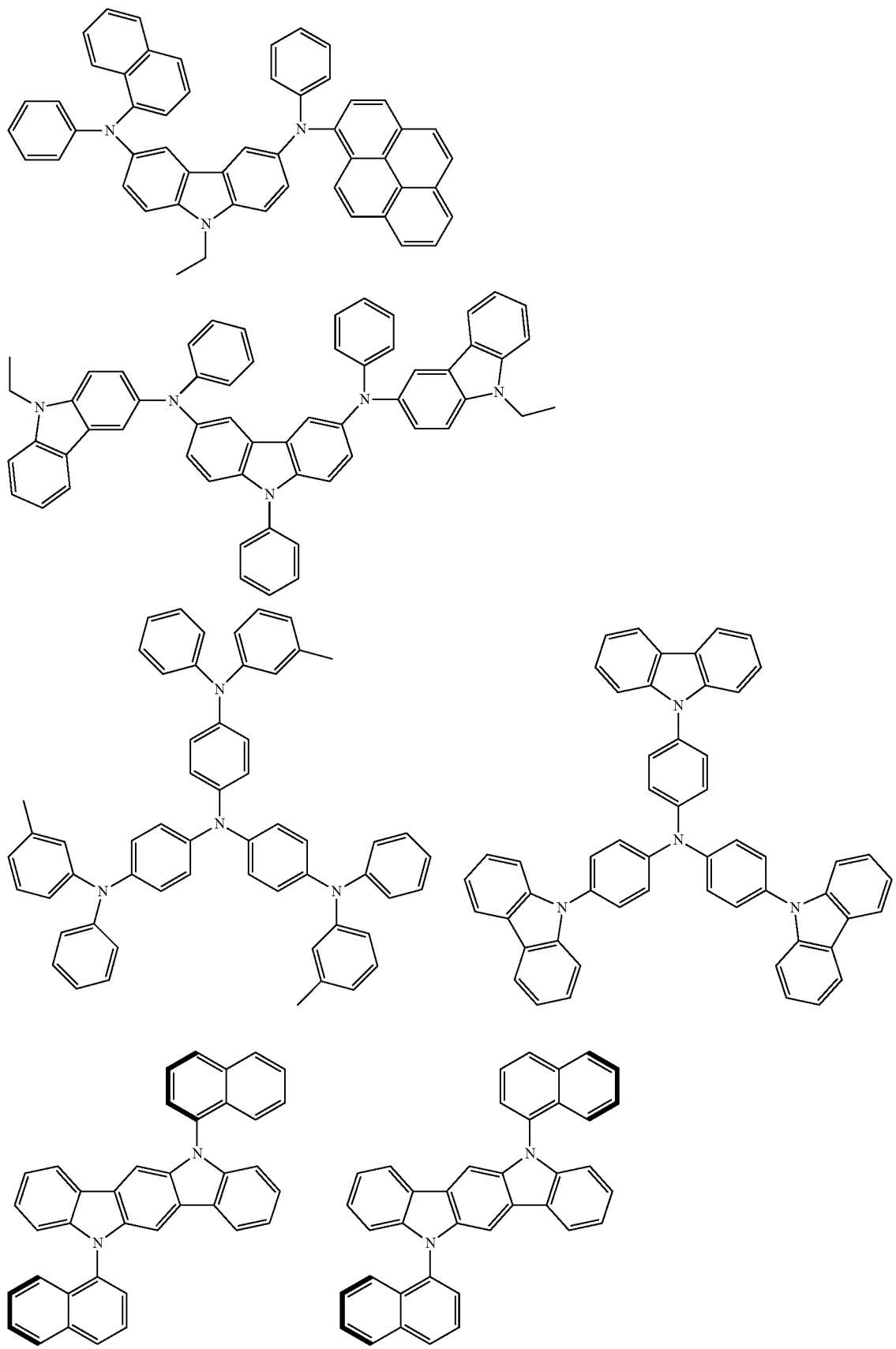

-continued
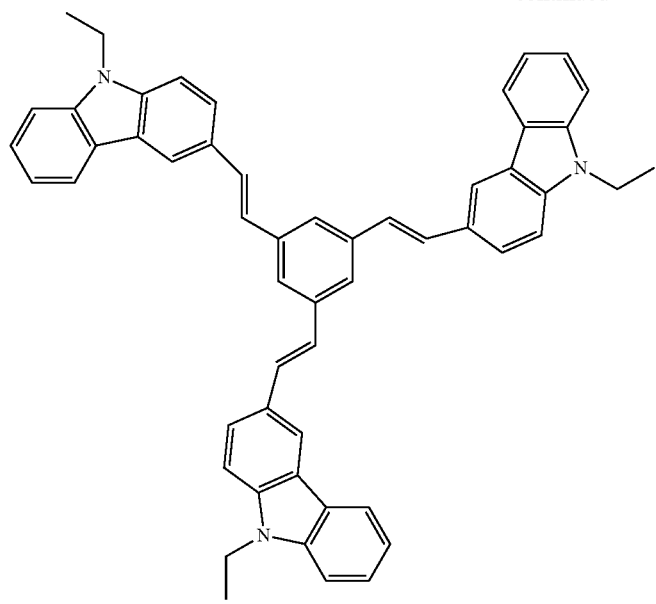
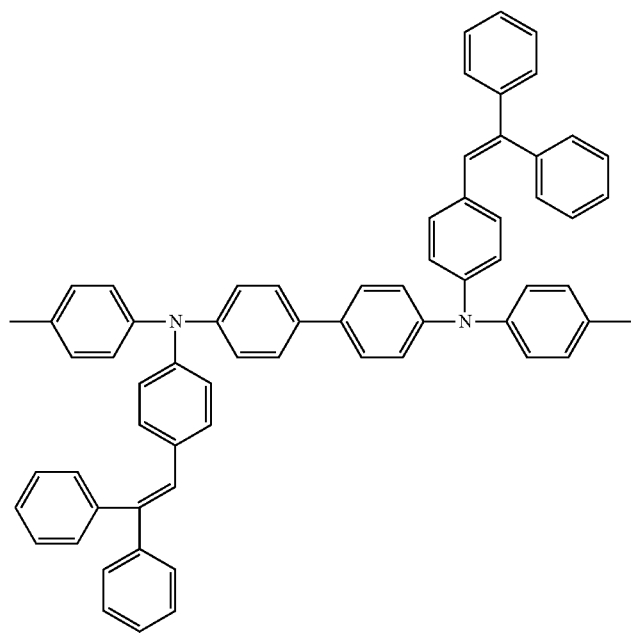
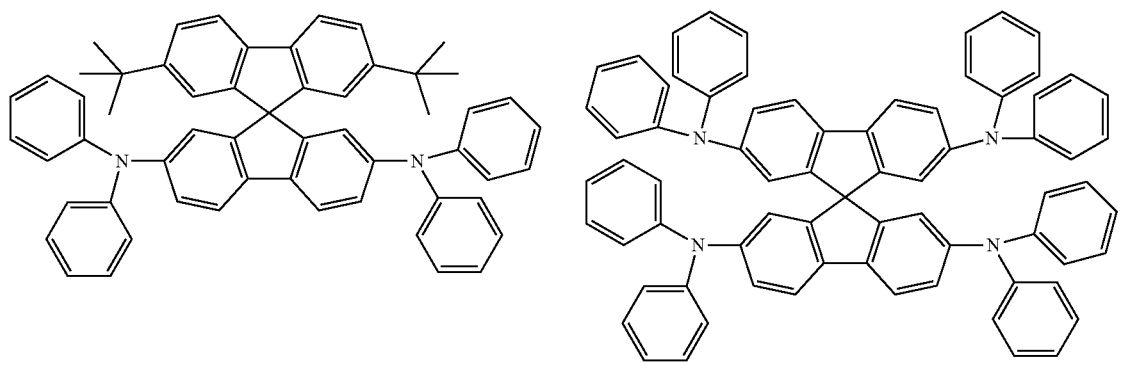

-continued
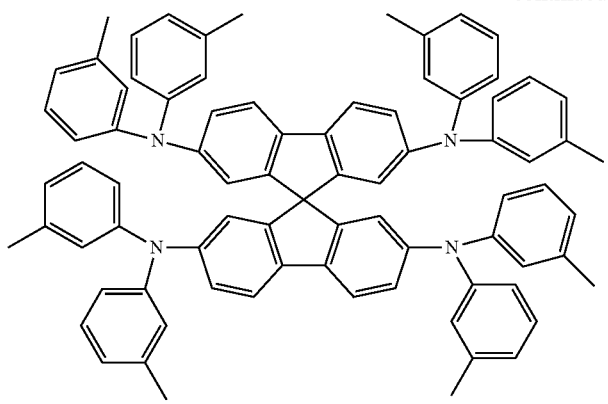
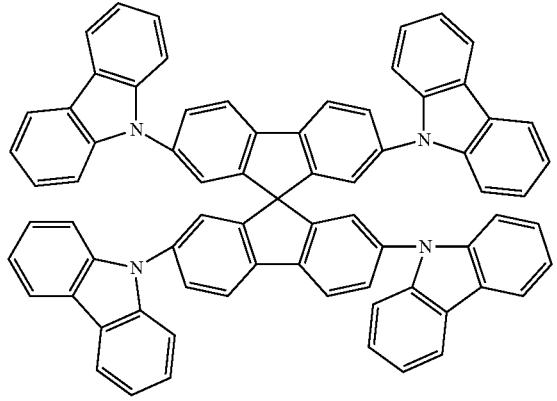
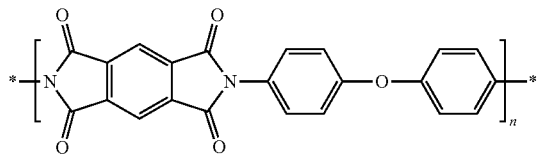
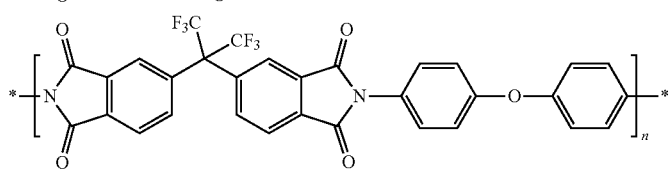
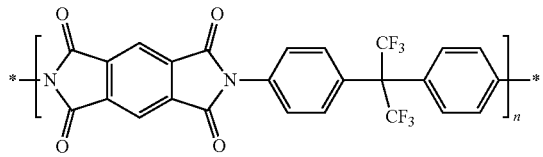
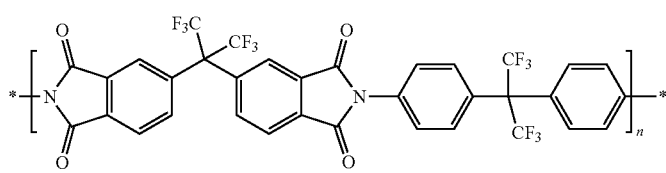
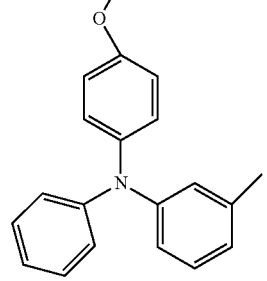

-continued
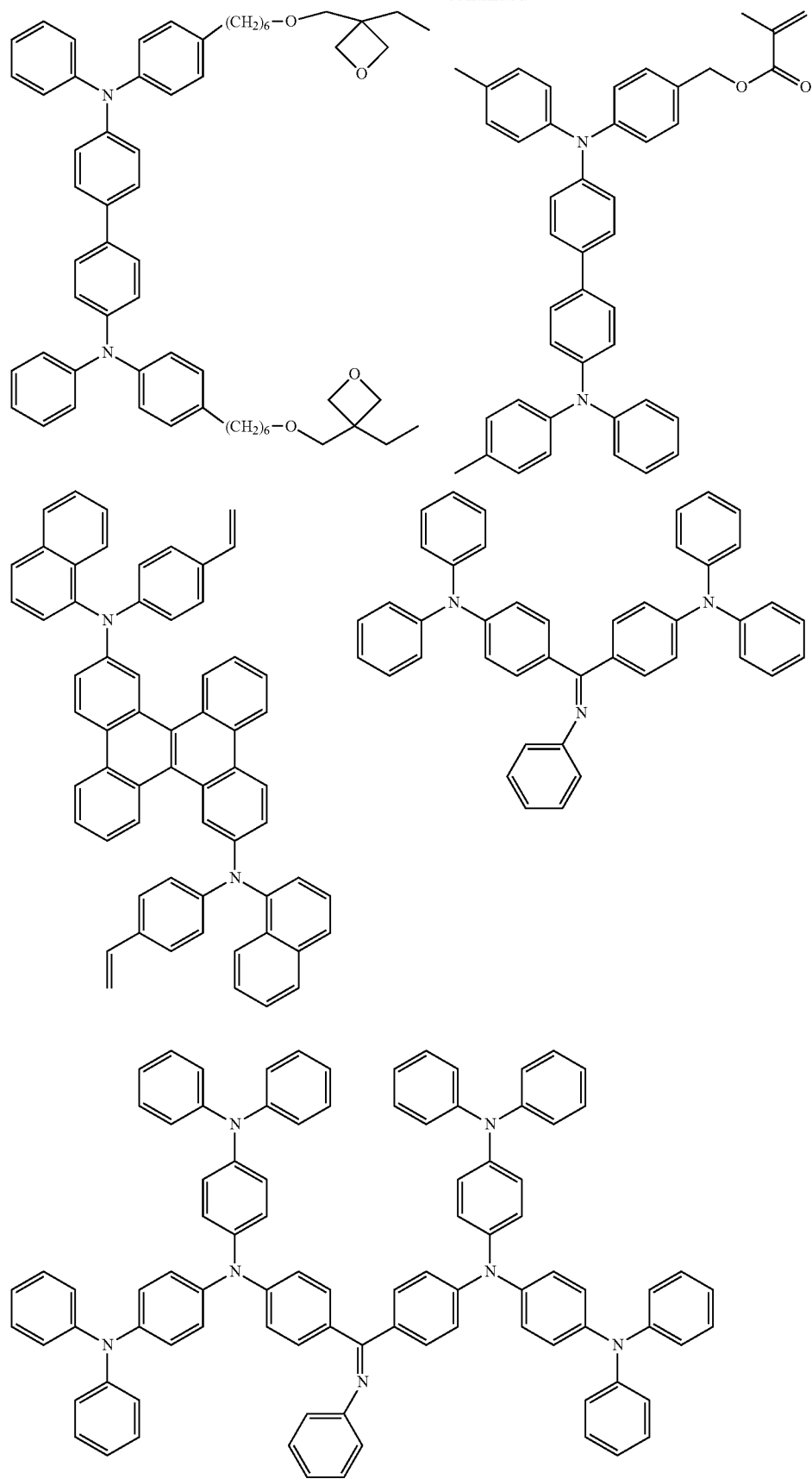

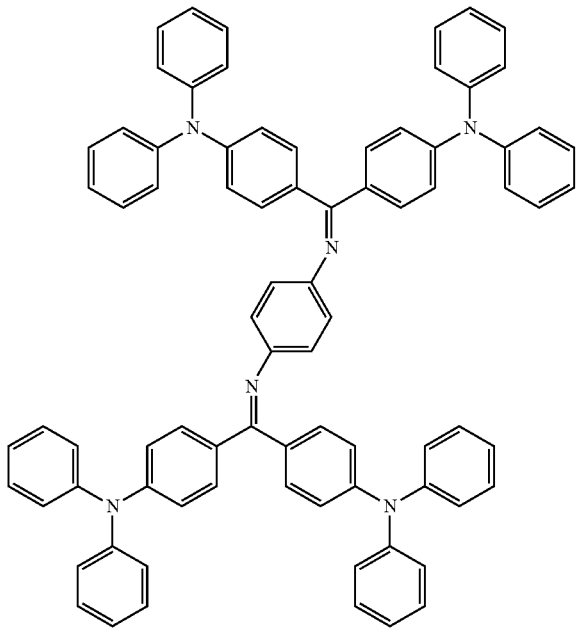
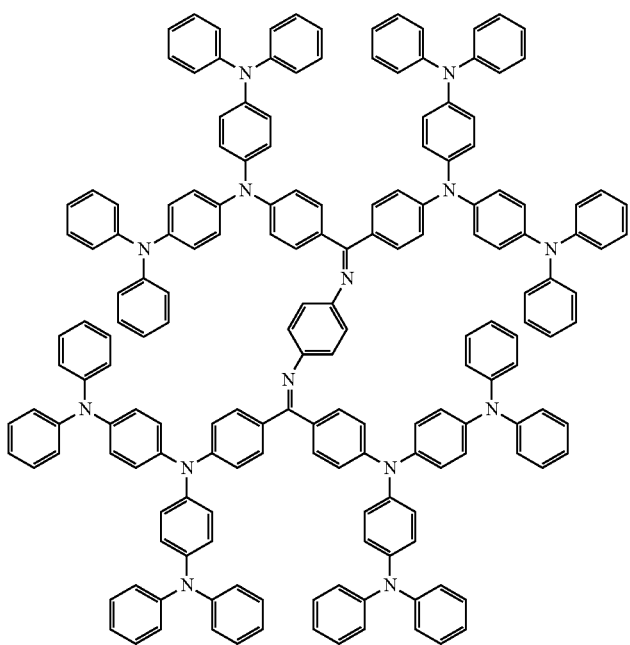

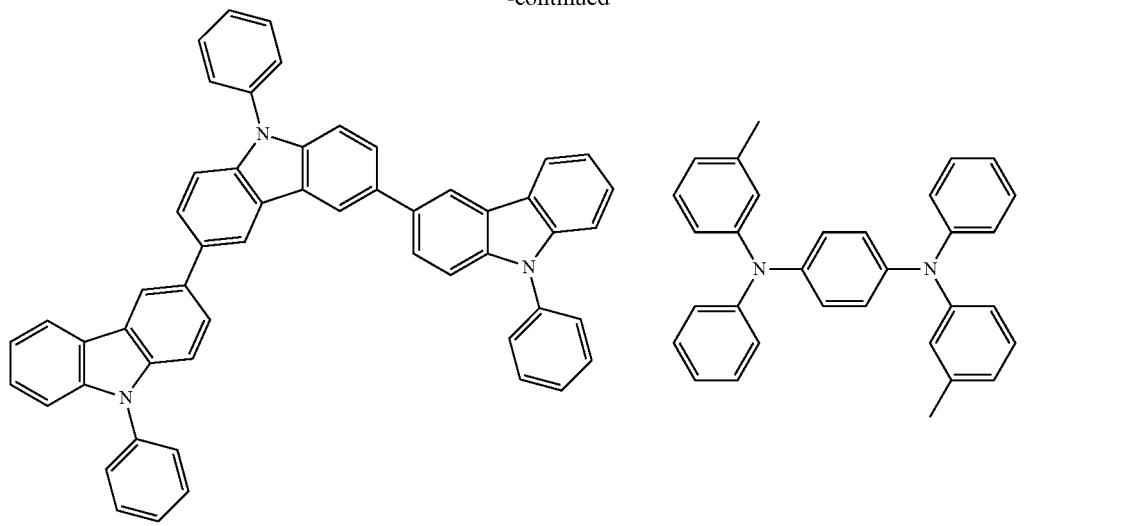
Next, preferred compounds for use as an electron blocking material are mentioned below.
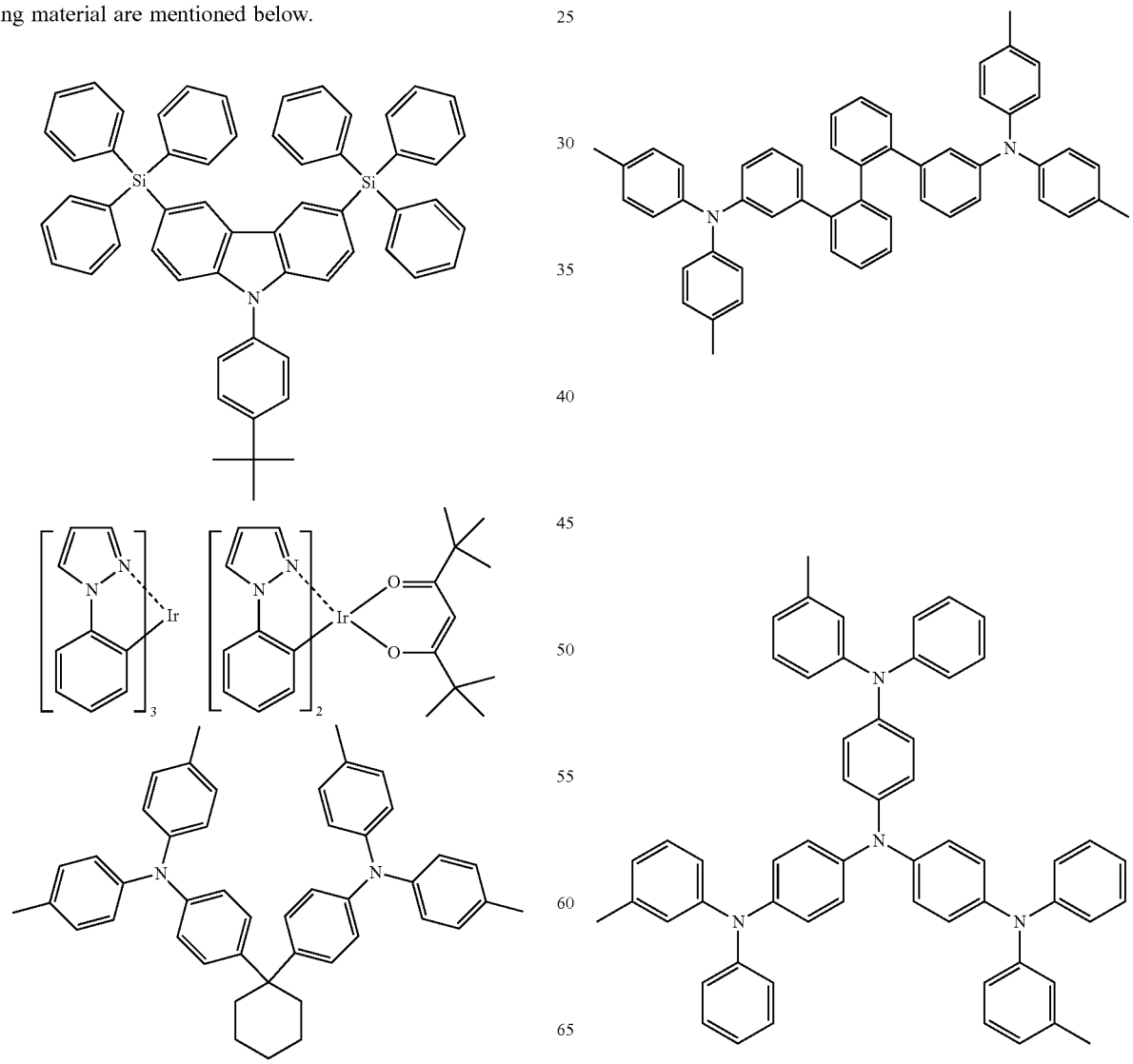

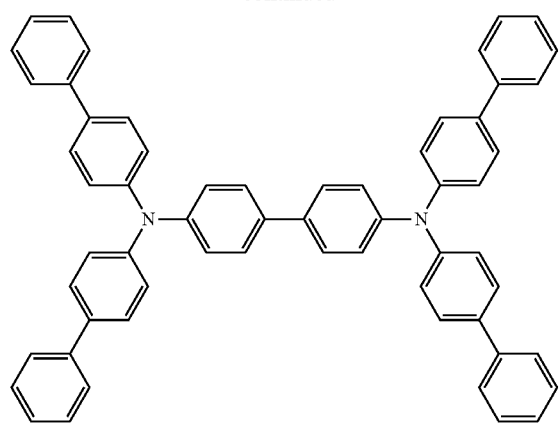
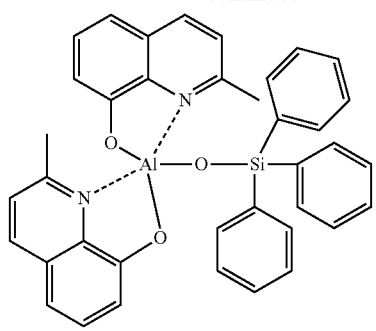
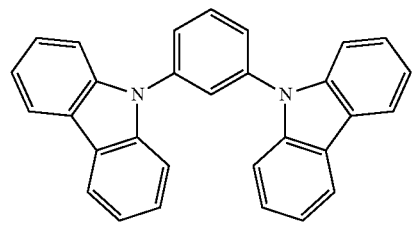
Next, preferred compounds for use as a hole blocking material are mentioned below.
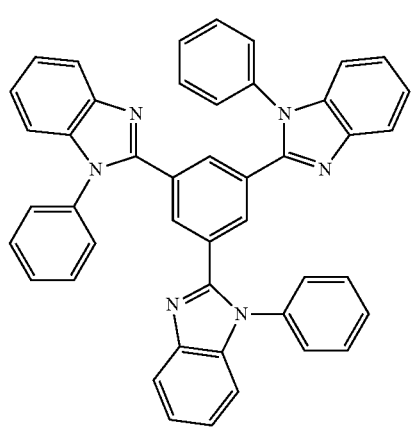
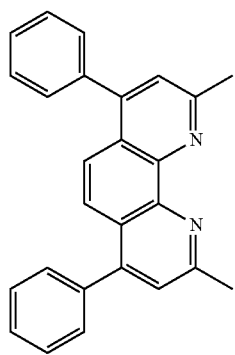
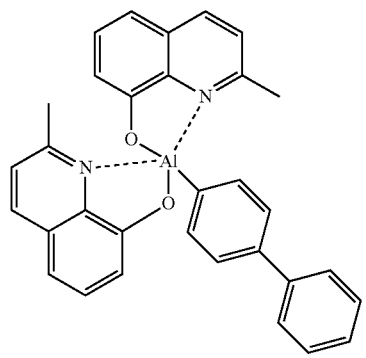
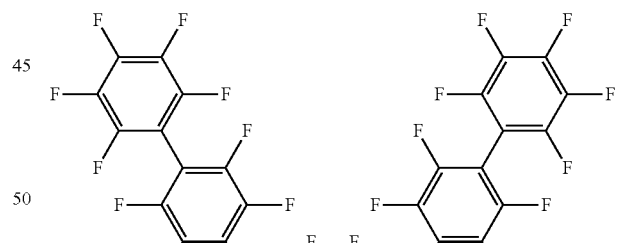

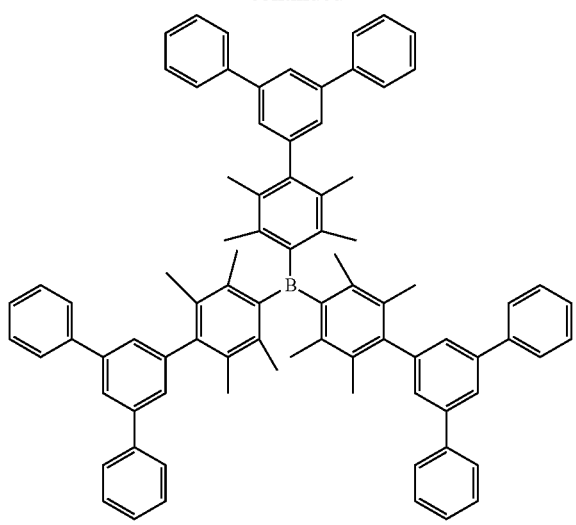
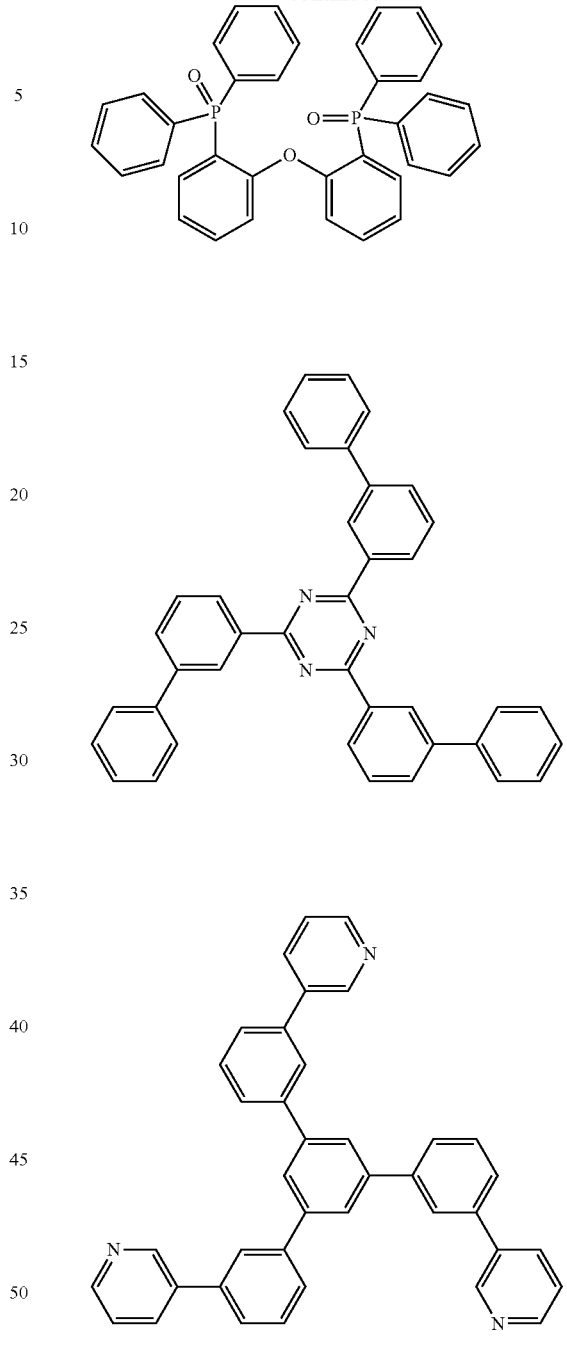
Next, preferred compounds for use as an electron transport material are mentioned below.
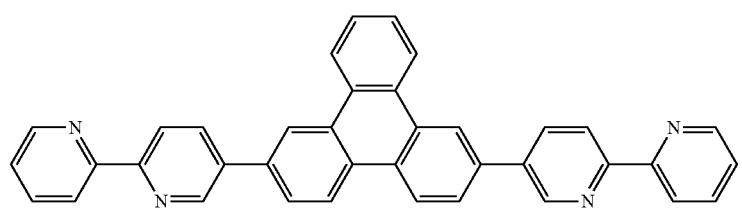

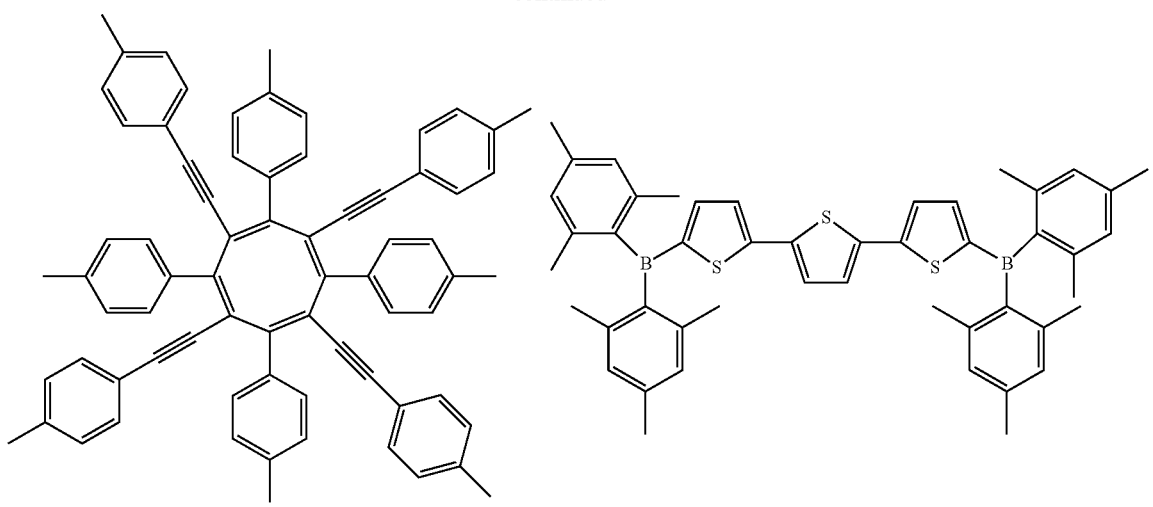
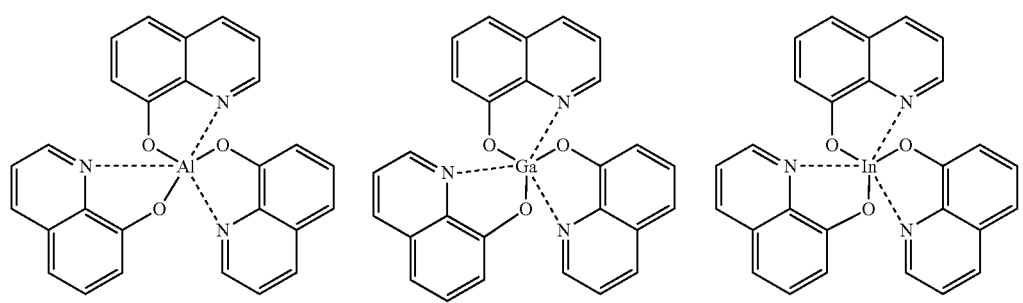
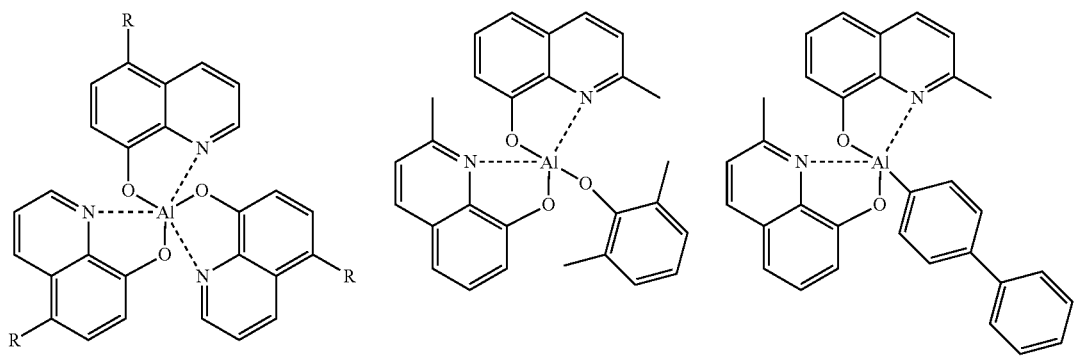
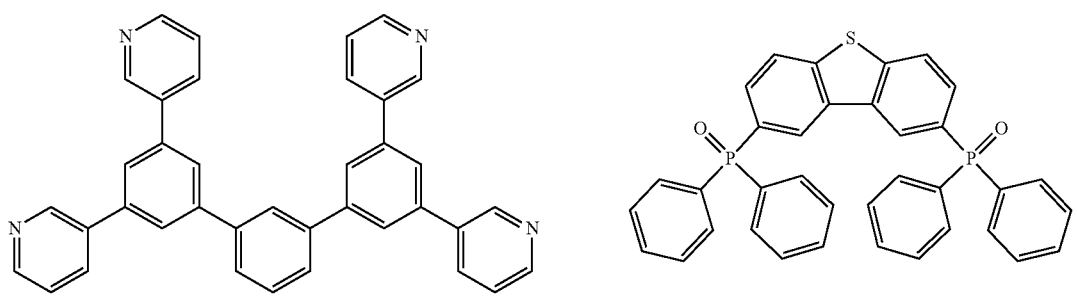

87 88
-continued
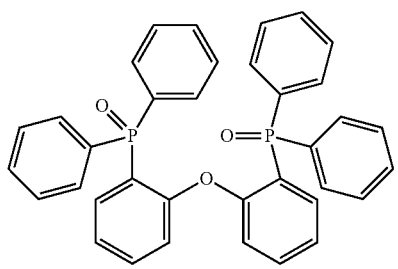 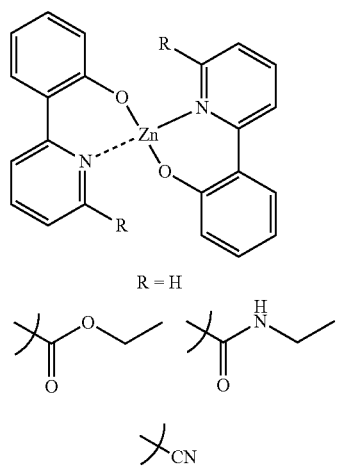
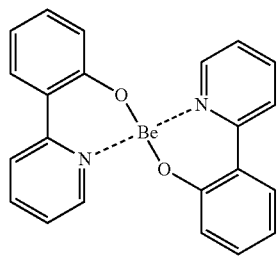 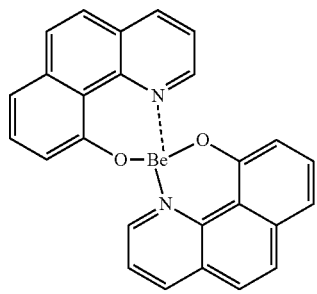 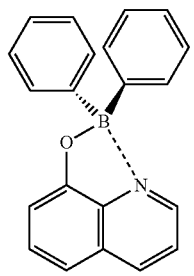
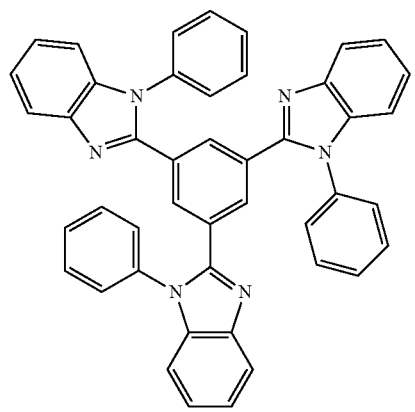 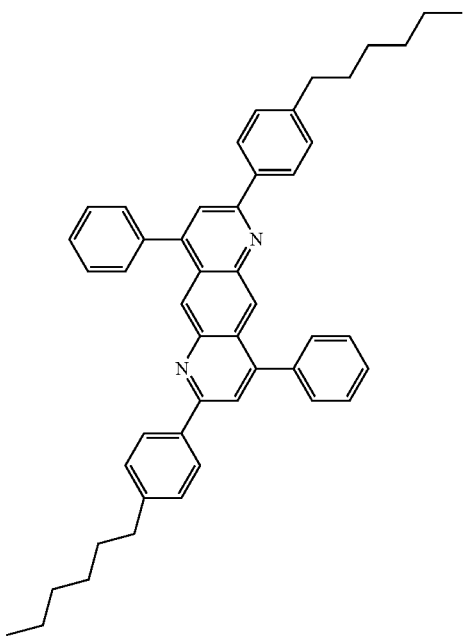

-continued
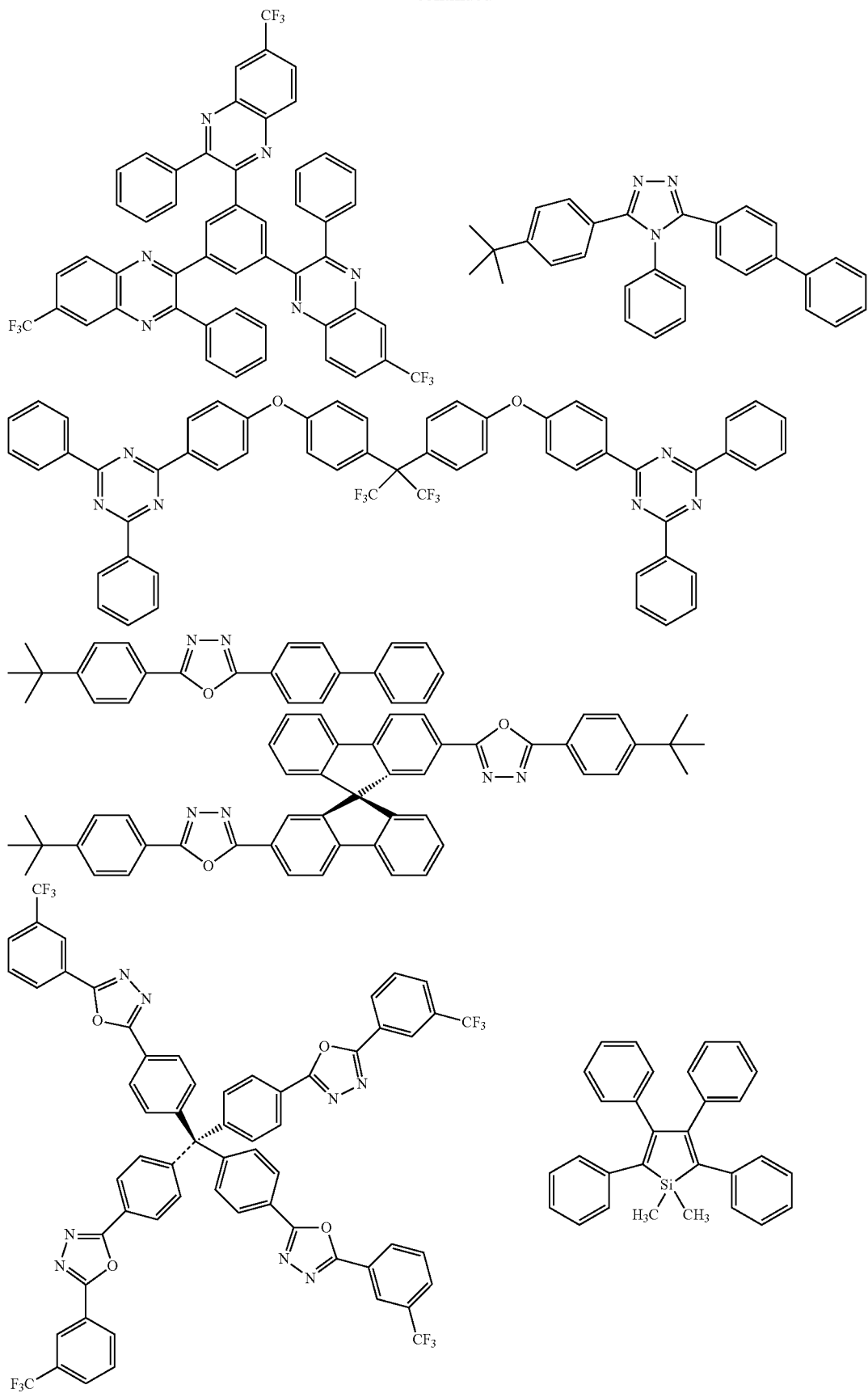

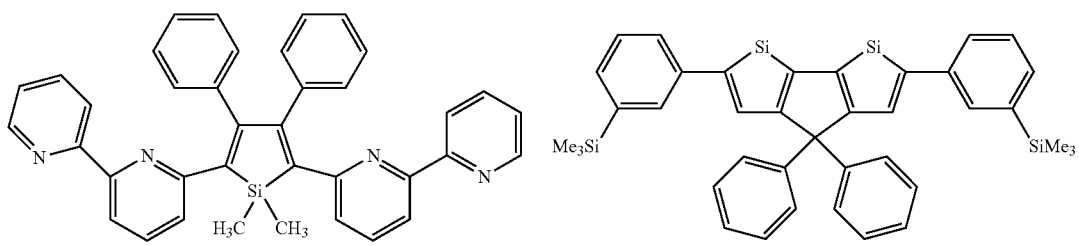
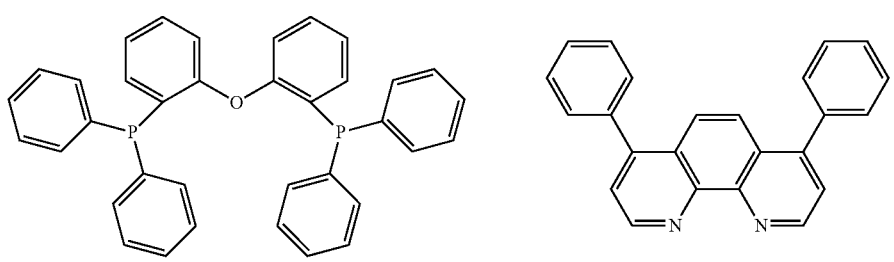
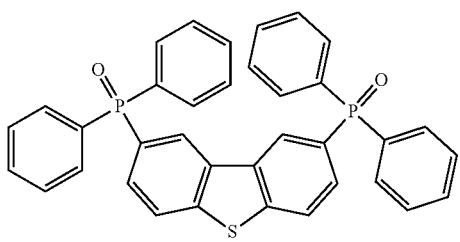
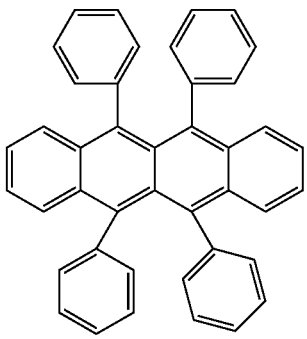
Next, preferred compounds for use as an electron injection material are mentioned below.
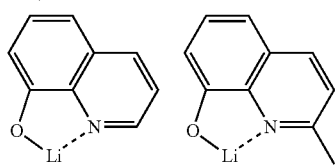
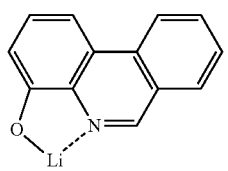
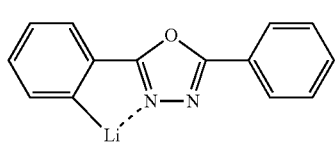
Further, preferred compounds for use as additional materials are mentioned below. For example, these are considered to be added as a stabilization material.
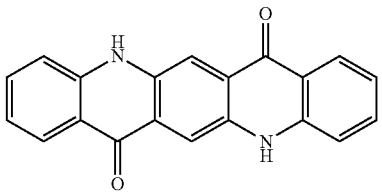

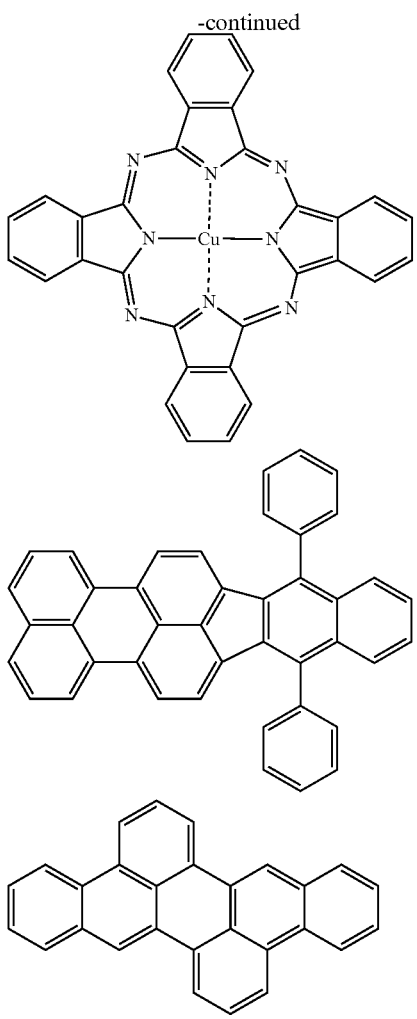

The organic electroluminescent device thus produced by the aforementioned method emits light on application of an electric field between the anode and the cathode of the device. In this case, when the light emission is caused by the excited singlet energy, light having a wavelength that corresponds to the energy level thereof may be confirmed as fluorescent light and delayed fluorescent light. When the light emission is caused by the excited triplet energy, light having a wavelength that corresponds to the energy level thereof may be confirmed as phosphorescent light. The normal fluorescent light has a shorter light emission lifetime than the delayed fluorescent light, and thus the light emission lifetime may be distinguished between the fluorescent light and the delayed fluorescent light.

On the other hand, the phosphorescent light may substantially not be observed with an ordinary organic compound such as the compound of the present invention at room temperature since the excited triplet energy thereof is unstable, and the rate constant of thermal deactivation of the compound is large while the rate constant of light emission is small, and therefore the compound immediately deactivates. The excited triplet energy of an ordinary organic compound may be measured by observing light emission under an extremely low temperature condition.

The organic electroluminescent device of the invention may be applied to any of a single device, a structure with plural devices disposed in an array, and a structure having anodes and cathodes disposed in an X-Y matrix. According to the present invention using the compound represented by the general formula (1) in a light-emitting layer, an organic light-emitting device having a markedly improved light emission efficiency can be obtained. The organic light-emitting device such as the organic electroluminescent device of the present invention may be applied to a further wide range of purposes. For example, an organic electroluminescent display apparatus may be produced with the organic electroluminescent device of the invention, and for the details thereof, reference may be made to S. Tokito, C. Adachi and H. Murata, "Yuki EL Display" (Organic EL Display) (Ohmsha, Ltd.). In particular, the organic electroluminescent device of the invention may be applied to organic electroluminescent illumination and backlight which are highly demanded.

EXAMPLES

The features of the present invention will be described more specifically with reference to Synthesis Examples and Examples given below. The materials, processes, procedures and the like shown below may be appropriately modified unless they deviate from the substance of the invention. Accordingly, the scope of the invention is not construed as being limited to the specific examples shown below.

Hereinunder the light emission characteristics were evaluated using Source Meter (available from Keithley Instruments Corporation: 2400 series), a semiconductor parameter analyzer (available from Agilent Corporation, E5273A), an optical power meter device (available from Newport Corporation, 1930C), an optical spectroscope (available from Ocean Optics Corporation, USB2000), a spectroradiometer (available from Topcon Corporation, SR-3), a nitrogen gas laser (available from USHO Inc., excitation wavelength 337 nm) and a streak camera (available from Hamamatsu Photonics K.K., Model C4334).

[Measurement of Difference $\Delta E_{ST}$ Between Lowest Excited Singlet Energy Level ($E_{S1}$) and Lowest Excited Triplet Energy Level ($E_{T1}$)]

A difference $\Delta E_{ST}$ between a lowest excited singlet energy level ($E_{S1}$) and a lowest excited triplet energy level ($E_{T1}$) of a compound was determined by calculating the lowest excited singlet energy level ($E_{S1}$) and the lowest excited triplet energy level ($E_{T1}$) from the fluorescence spectrum and the phosphorescence spectrum of the compound, according to an equation, $\Delta E_{ST}=E_{S1}-E_{T1}$.

(1) Lowest Excited Singlet Energy Level ($E_{S1}$)

A thin film or a toluene solution (concentration: $10^{-5}$ mol/L) of the compound to be analyzed was prepared as a measurement sample, and the fluorescent spectrum of the sample was measured at room temperature (300 K). For the fluorescent spectrum, the emission intensity was on the vertical axis and the wavelength was on the horizontal axis. A tangent line was drawn to the rising of the emission spectrum on the short wavelength side, and the wavelength value λedge [nm] at the intersection between the tangent line and the horizontal axis was read. The wavelength value was converted into an energy value according to the following conversion expression to calculate $E_{S1}$.

$E_{S1}$ [eV]=1239.85/λedge     Conversion Expression:

For the measurement of the emission spectrum, an LED light source (available from Thorlabs Corporation, M340L4) was used as an excitation light source along with a detector (available from Hamamatsu Photonics K.K., PMA-50).

(2) Lowest Excited Triplet Energy Level ($E_{T1}$)

The same sample as that for measurement of the lowest excited singlet energy level ($E_{S1}$) was cooled to 77 [K] with liquid nitrogen, and the sample for phosphorescence measurement was irradiated with excitation light (340 nm), and using a detector, the phosphorescence thereof was measured. The emission after 100 milliseconds from irradiation with the excitation light was drawn as a phosphorescent spectrum. A tangent line was drawn to the rising of the phosphorescent spectrum on the short wavelength side, and the wavelength value λedge [nm] at the intersection between the tangent line and the horizontal axis was read. The wavelength value was converted into an energy value according to the following conversion expression to calculate $E_{T1}$.

$E_{T1}$ [eV]=1239.85/λedge      Conversion Expression:

The tangent line to the rising of the phosphorescent spectrum on the short wavelength side was drawn as follows. While moving on the spectral curve from the short wavelength side of the phosphorescent spectrum toward the maximum value on the shortest wavelength side among the maximum values of the spectrum, a tangent line at each point on the curve toward the long wavelength side was taken into consideration. With rising thereof (that is, with increase in the vertical axis), the inclination of the tangent line increases. The tangent line drawn at the point at which the inclination value has a maximum value was referred to as the tangent line to the rising on the short wavelength side of the phosphorescent spectrum.

The maximum point having a peak intensity of 10% or less of the maximum peak intensity of the spectrum was not included in the maximum value on the above-mentioned shortest wavelength side, and the tangent line drawn at the point which is closest to the maximum value on the shortest wavelength side and at which the inclination value has a maximum value was referred to as the tangent line to the rising on the short wavelength side of the phosphorescent spectrum.

[Calculation of Difference $\Delta E_{ST}$ Between Lowest Excited Singlet Energy Level ($E_{S1}$) and Lowest Excited Triplet Energy Level ($E_{T1}$) According to Computational Chemistry]

In this Example, the difference $\Delta E_{ST}$ between a lowest excited singlet energy level ($E_{S1}$) and a lowest excited triplet energy level ($E_{T1}$) of a compound was calculated according to computational chemistry. For computational chemistry, Gaussian 09 and Gaussian 16 programs by Gaussian Corporation were used. Here, for optimization of the molecular structure in a ground singlet state $S_0$ and for calculation of an electron state, a B3LYP/6-31G (d) method was used; and for calculation of a lowest excited singlet energy level ($E_{S1}$) and a lowest excited triplet energy level ($E_{T1}$), a time-dependent density-functional calculation method (TD-DFT) was used. From the resultant data of a lowest excited singlet energy level ($E_{S1}$) and a lowest excited triplet energy level ($E_{T1}$), $\Delta E_{ST}$ was calculated according to $\Delta E_{ST}=E_{S1}-E_{T1}$.

[Compounds Used in Examples]

Structures of the compounds of the invention and the comparative compounds used in Examples, and mCBP used as a host in a doped film are shown below.

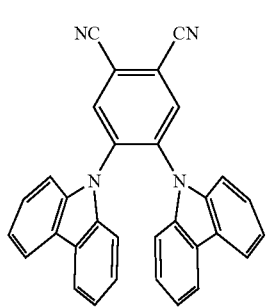

Comparative Compound 1-1

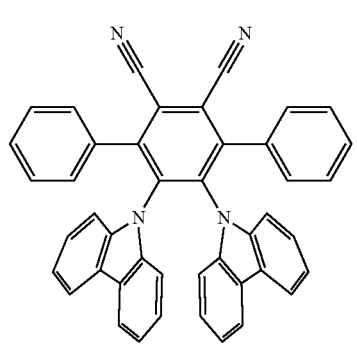

Invention Compound 1-1

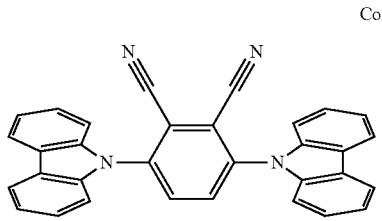

Comparative Compound 2-1

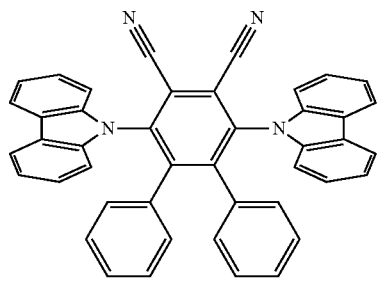

Invention Compound 2-1

-continued
Comparative Compound 3-1
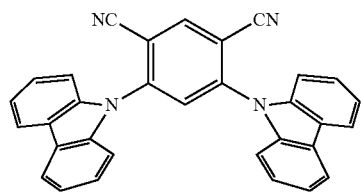
Invention Compound 3-1
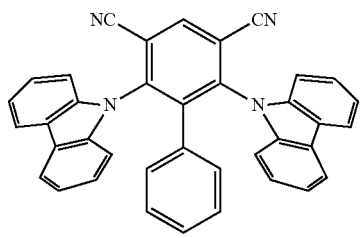
Invention Compound 3-2
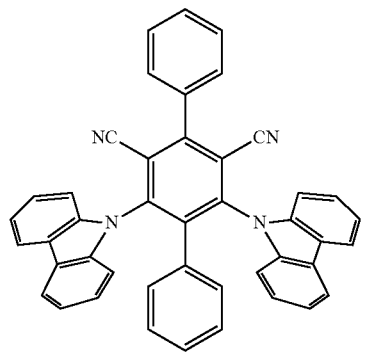
Invention Compound 3-3
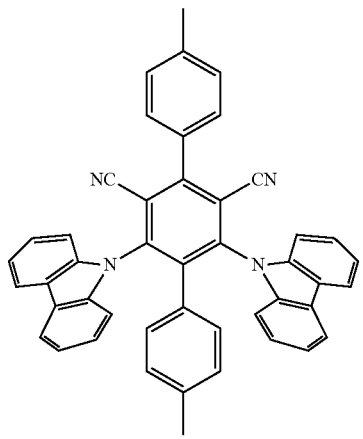
Invention Compound 3-4
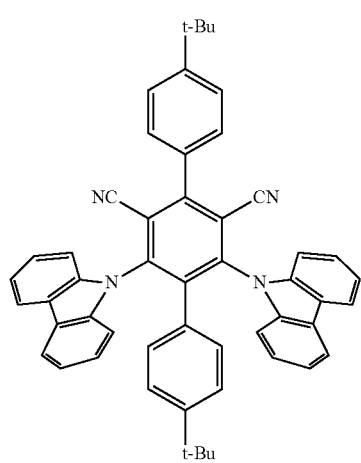
Invention Compound 3-5
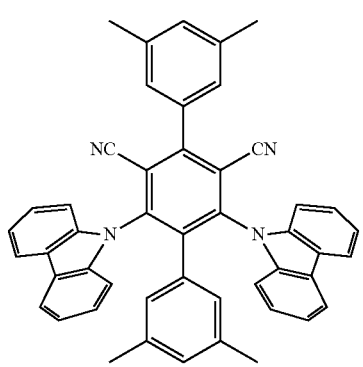
Comparative Compound 4-1
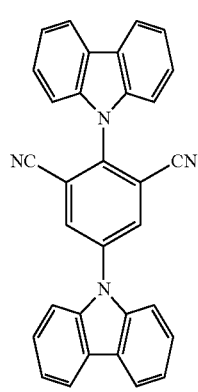
Invention Compound 4-1
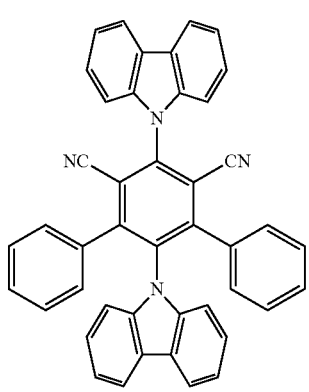

-continued
Comparative Compound 5-1
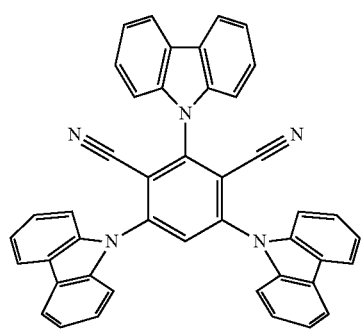
Invention Compound 5-1
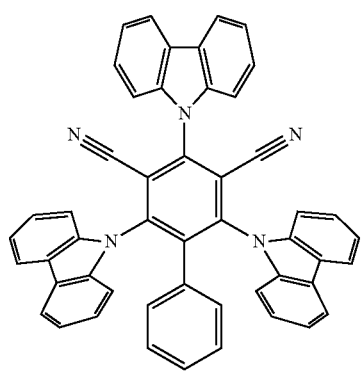
Comparative Compound 6-1
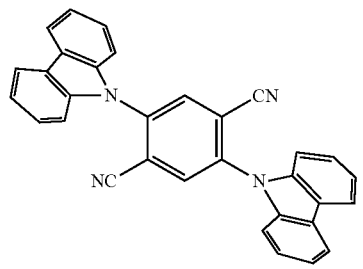
Invention Compound 6-1
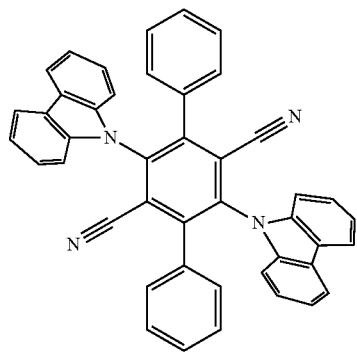
Invention Compound 6-2
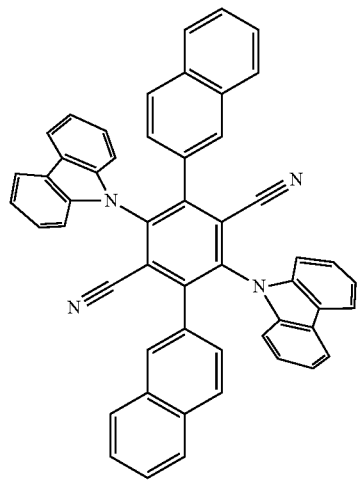
Invention Compound 6-3
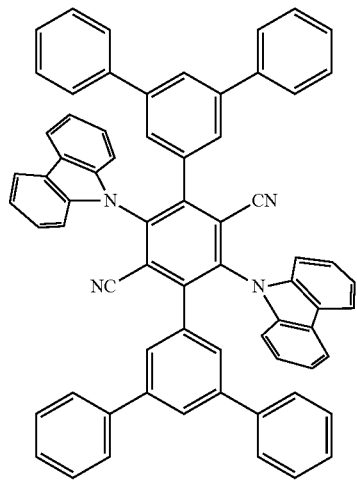

-continued
Invention Compound 6-4
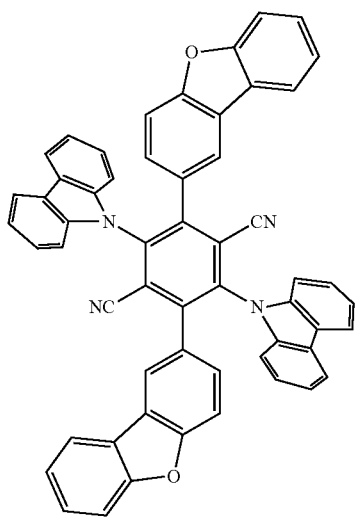
Comparative Compound 7-1
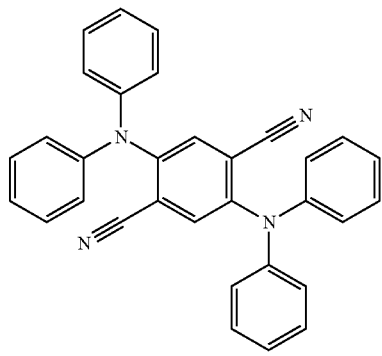
Invention Compound 7-1
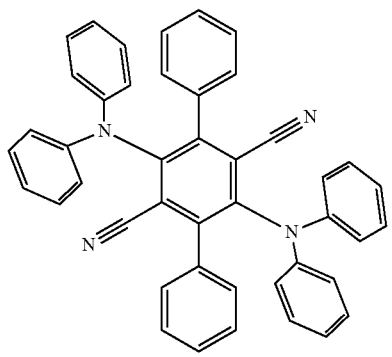
Compound Compound 8-1
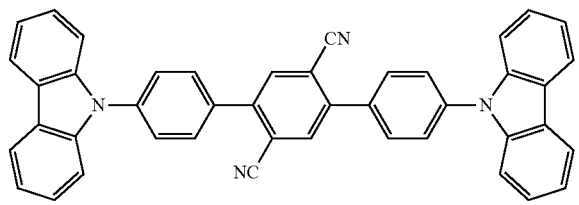
Invention Compound 8-1
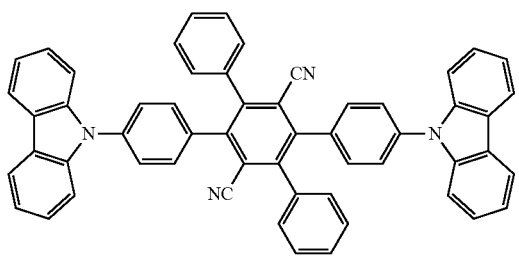
Invention Compound 8-2
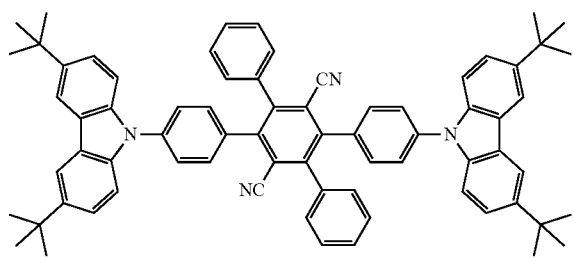
Invention Compound 8-3
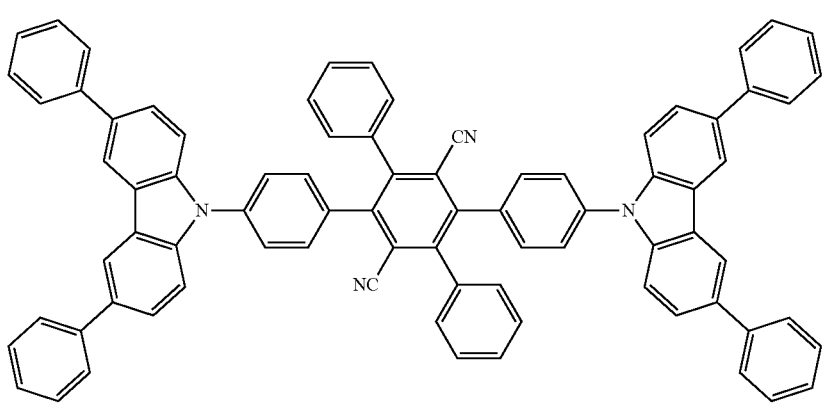

-continued
Invention Compound 8-4
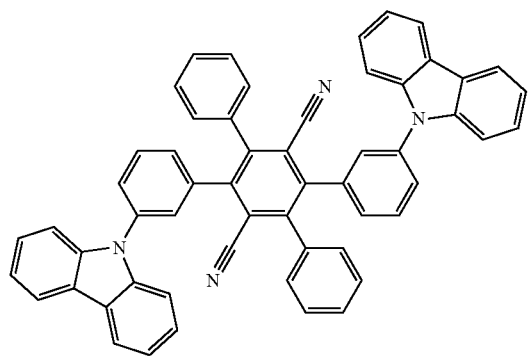
Invention Compound 8-5
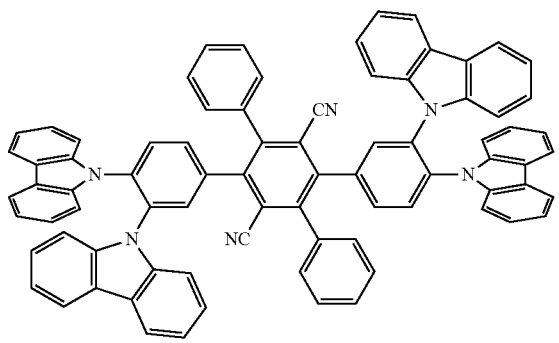
Comparative Compound 9-1
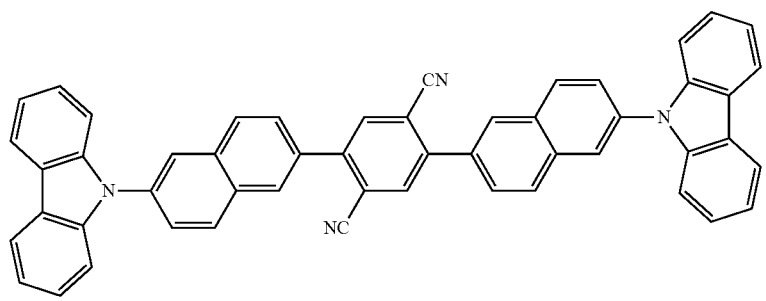
Invention Compound 9-1
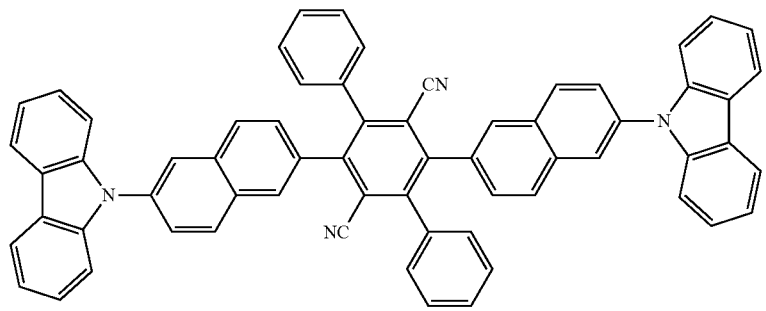
Invention Compound 9-2
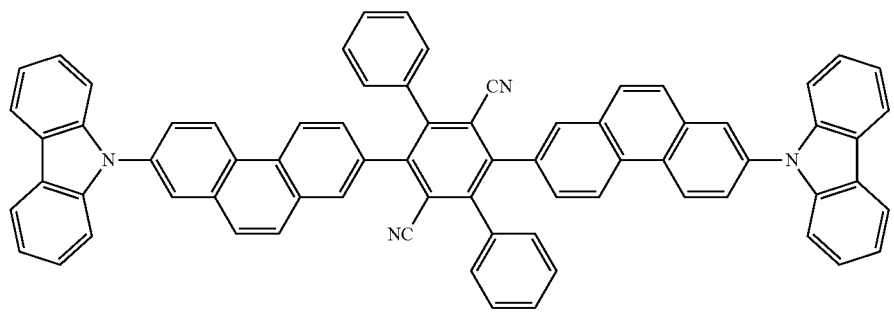

-continued
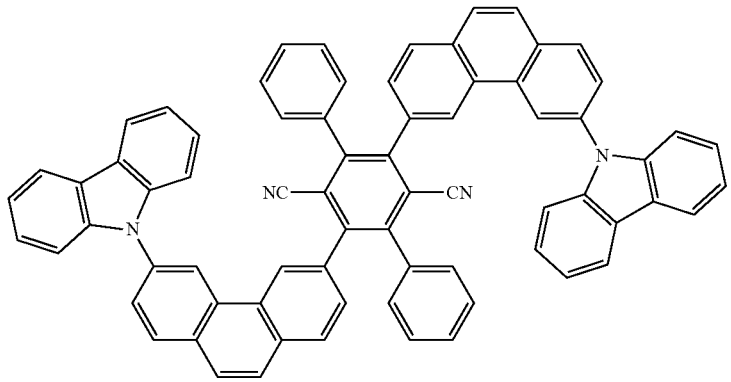
Invention Compound 9-3
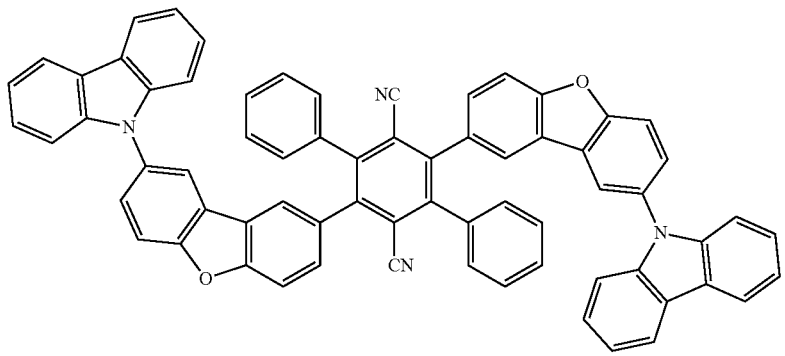
Invention Compound 9-4
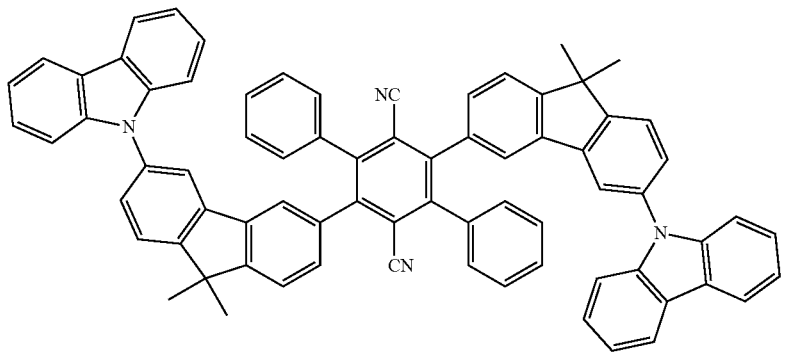
Invention Compound 9-5
Comparative Compound 10-1
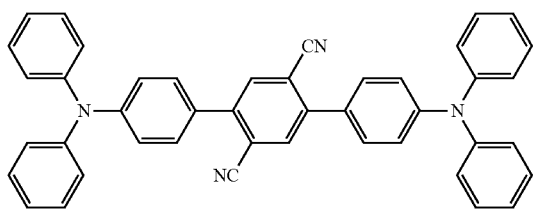
Invention Compound 10-1
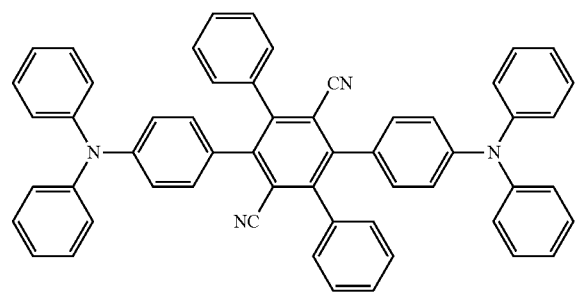

-continued
Invention Compound 10-2

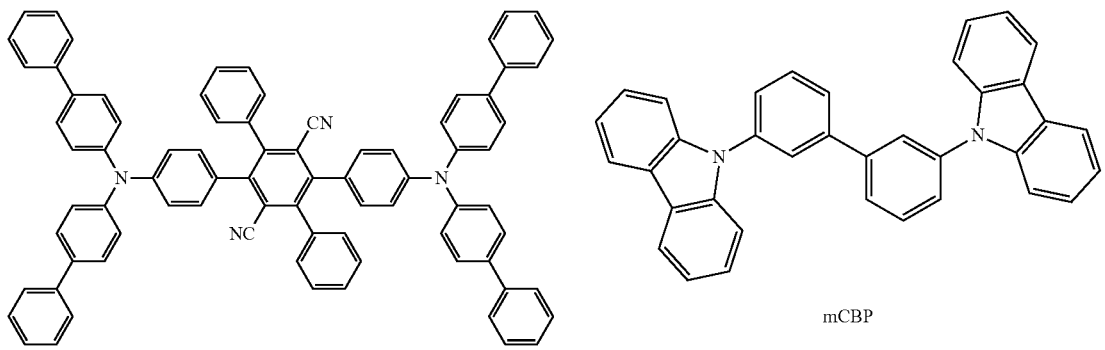

mCBP

[A] Synthesis of Compounds (Synthesis Example 1) Synthesis of Invention Compound 6-1

(1) Synthesis of Intermediate 1

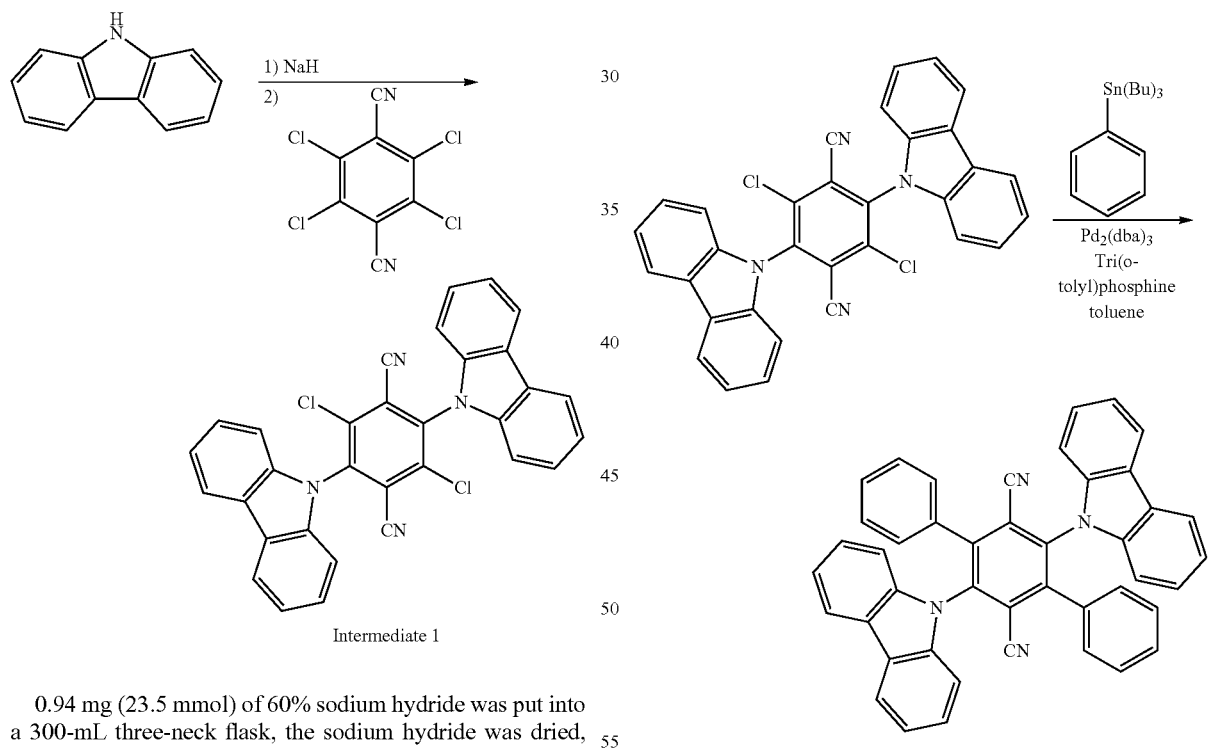

0.94 mg (23.5 mmol) of 60% sodium hydride was put into a 300-mL three-neck flask, the sodium hydride was dried, then the flask was purged with nitrogen, and 200 mL of tetrahydrofuran (dewatered solvent) was added and stirred. 3.14 g (18.8 mmol) of 9H-carbazole was added to the mixture, and in a nitrogen stream atmosphere, this was stirred at room temperature for 60 minutes. After stirring, 2.50 g (9.40 mmol) of tetrachloroterephthalonitrile was added to the mixture, and the mixture was stirred at room temperature in a nitrogen atmosphere for 12 hours. After stirring, water was added to the mixture and stirred, and the precipitate was filtered out. After filtration, the mixture was purified through silica gel column chromatography. In column chromatography, a mixed solvent of toluene/hexane was used as a developing solvent. The resultant fraction was concentrated to give a solid, which was then recrystallized with a mixed solvent of acetone and hexane to give a yellow powdery solid in a yield amount of 2.01 g and a yield of 40.3%.

$^1$H NMR (500 Hz, CDCl$_3$, δ): 8.21 (d, J=10 Hz, 2H), 7.54 (td, J=7.5 Hz, J=1 Hz, 2H), 7.45 (td, J=7.5 Hz, J=1 Hz, 2H), 7.15 (d, J=8.5 Hz, 2H)

Mass Spectroscopy Analysis: 526.0

(2) Synthesis of Invention Compound 6-1

1.55 g (2.93 mmol) of the intermediate 1, 3.2 g (8.8 mmol) of tributylphenyl stannane, 0.10 g (0.093 mmol) of tris(dibenzylideneacetone)dipalladium(0) and 0.26 g (0.88 mmol) of tri(o-tolyl)phosphine were put into a 200-mL three-neck flask, and the flaks was purged with nitrogen. 70 mL of toluene was added to the mixture, and in a nitrogen atmosphere, this was stirred at 100° C. for 24 hours. The mixture was purified through silica gel column chromatography. In column chromatography, a mixed solvent of ethyl acetate/hexane=1/9 was used as a developing solvent. The resultant fraction was concentrated to give a solid, which was then recrystallized with a mixed solvent of acetone and hexane to give a yellow powdery solid in a yield amount of 0.36 g and a yield of 20.2%.

$^1$H NMR (500 Hz, CDCl$_3$, δ): 8.03 (d, J=7.9 Hz, 4H), 7.42 (t, J=8.0 Hz, 4H), 7.28 (t, J=7.9 Hz, 4H), 7.19 (d, J=8.1 Hz, 4H), 7.14 (d, J=7.0 Hz, 4H), 7.09 (t, J=7.9 Hz, 2H), 7.42 (t, J=7.7 Hz, 4H)

Mass Spectroscopy Analysis: 610.10

(Synthesis Example 2) Synthesis of Invention Compound 8-1

(1) Synthesis of Intermediate 2

(2) Synthesis of Invention Compound 8-1

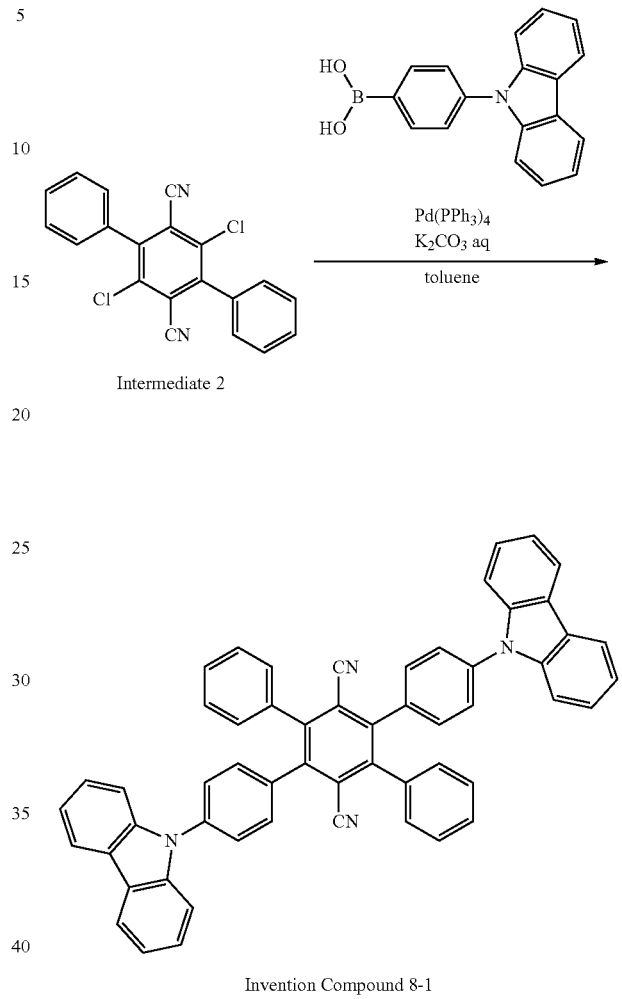

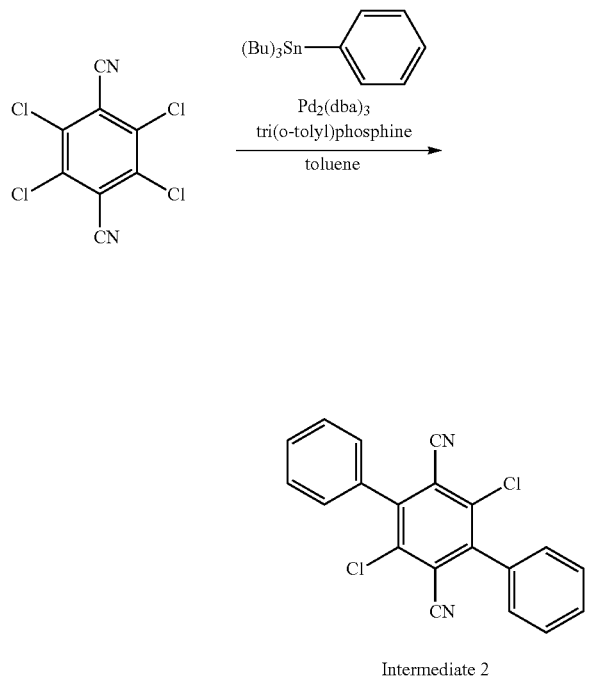

0.26 g (1.0 mmol) of tetrachloroterephthalonitrile, 0.81 g (2.2 mmol) of tributylphenyl stannane, 0.03 g (0.03 mmol) of tris(dibenzylideneacetone)dipalladium(0) and 0.09 g (0.3 mmol) of tri(o-tolyl)phosphine were put into a flask, the flask was purged with nitrogen, then 20 mL of toluene was added, and stirred at 120° C. in a nitrogen atmosphere for 24 hours. After stirring, the mixture was restored to room temperature, and purified through silica gel column chromatography. Toluene and hexane were used as a developing solvent in column chromatography. The resultant fraction was concentrated to give a solid, which was then recrystallized with dichloromethane and hexane to give an intermediate 2 in a yield amount of 0.070 g and a yield of 20%.

Mass Spectroscopy Analysis: 347.98

0.17 g (0.5 mmol) of the intermediate 2, 0.31 g (1.1 mmol) of 4-(9H-carbazolyl)phenylboronic acid and 15 mL of dewatered toluene were put into a 15-mL Schlenk tube. 0.11 g (0.1 mmol) of tetrakis(triphenylphosphine)palladium(0), and 6 mL of an aqueous solution of 2 M potassium carbonate were added to the mixture and stirred at 80° C. for 72 hours. After stirring, the mixture was restored to room temperature, and the precipitate in the mixture was taken out through filtration. The precipitate was washed with water, hexane and methanol in that order to give an invention compound 8-1.

Calculation of ΔE$_{ST}$ According to Computational Chemistry

The above-mentioned invention compounds and comparative compounds were analyzed according to computational chemistry to determine the lowest excited singlet energy level (E$_{S1}$) and the lowest excited triplet energy level (E$_{T1}$) thereof, and the energy difference ΔE$_{ST}$ therebetween was calculated and shown in Tables 6 to 15. "Relative value" of the invention compound in each Table is a relative value of ΔE$_{ST}$ of each compound as calculated on the basis of ΔE$_{ST}$, 1.00, of the corresponding comparative compound (comparative compound shown in the same Table).

TABLE 6

|  | $E_{S1}$ (eV) | $E_{T1}$ (eV) | $\Delta E_{ST}$ (eV) | Relative Value |
| --- | --- | --- | --- | --- |
| Comparative Compound 1-1 | 2.842 | 2.501 | 0.341 | 1.00 |
| Invention Compound 1-1 | 2.627 | 2.473 | 0.154 | 0.45 |

TABLE 7

|  | $E_{S1}$ (eV) | $E_{T1}$ (eV) | $\Delta E_{ST}$ (eV) | Relative Value |
| --- | --- | --- | --- | --- |
| Comparative Compound 2-1 | 2.665 | 2.489 | 0.176 | 1.00 |
| Invention Compound 2-1 | 2.598 | 2.553 | 0.045 | 0.25 |

TABLE 8

|  | $E_{S1}$ (eV) | $E_{T1}$ (eV) | $\Delta E_{ST}$ (eV) | Relative Value |
| --- | --- | --- | --- | --- |
| Comparative Compound 3-1 | 2.806 | 2.601 | 0.205 | 1.00 |
| Invention Compound 3-1 | 2.584 | 2.524 | 0.061 | 0.30 |
| Invention Compound 3-2 | 2.629 | 2.570 | 0.059 | 0.29 |
| Invention Compound 3-3 | 2.651 | 2.591 | 0.061 | 0.29 |
| Invention Compound 3-4 | 2.657 | 2.596 | 0.061 | 0.30 |
| Invention Compound 3-5 | 2.662 | 2.604 | 0.059 | 0.29 |

TABLE 9

|  | $E_{S1}$ (eV) | $E_{T1}$ (eV) | $\Delta E_{ST}$ (eV) | Relative Value |
| --- | --- | --- | --- | --- |
| Comparative Compound 4-1 | 2.704 | 2.599 | 0.105 | 1.00 |
| Invention Compound 4-1 | 2.719 | 2.663 | 0.055 | 0.53 |

TABLE 10

|  | $E_{S1}$ (eV) | $E_{T1}$ (eV) | $\Delta E_{ST}$ (eV) | Relative Value |
| --- | --- | --- | --- | --- |
| Comparative Compound 5-1 | 2.684 | 2.568 | 0.116 | 1.00 |
| Invention Compound 5-1 | 2.487 | 2.449 | 0.039 | 0.33 |

TABLE 11

|  | $E_{S1}$ (eV) | $E_{T1}$ (eV) | $\Delta E_{ST}$ (eV) | Relative Value |
| --- | --- | --- | --- | --- |
| Comparative Compound 6-1 | 2.477 | 2.294 | 0.183 | 1.00 |
| Invention Compound 6-1 | 2.498 | 2.420 | 0.079 | 0.43 |
| Invention Compound 6-2 | 2.509 | 2.426 | 0.084 | 0.46 |
| Invention Compound 6-3 | 2.493 | 2.415 | 0.078 | 0.42 |
| Invention Compound 6-4 | 2.477 | 2.414 | 0.063 | 0.35 |

TABLE 12

|  | $E_{S1}$ (eV) | $E_{T1}$ (eV) | $\Delta E_{ST}$ (eV) | Relative Value |
| --- | --- | --- | --- | --- |
| Comparative Compound 7-1 | 2.531 | 2.097 | 0.434 | 1.00 |
| Invention Compound 7-1 | 2.379 | 2.133 | 0.246 | 0.57 |

TABLE 13

|  | $E_{S1}$ (eV) | $E_{T1}$ (eV) | $\Delta E_{ST}$ (eV) | Relative Value |
| --- | --- | --- | --- | --- |
| Comparative Compound 8-1 | 2.577 | 2.419 | 0.158 | 1.00 |
| Invention Compound 8-1 | 2.706 | 2.642 | 0.064 | 0.40 |
| Invention Compound 8-2 | 2.566 | 2.516 | 0.050 | 0.32 |
| Invention Compound 8-3 | 2.554 | 2.515 | 0.039 | 0.24 |
| Invention Compound 8-4 | 2.452 | 2.375 | 0.077 | 0.49 |
| Invention Compound 8-5 | 2.586 | 2.574 | 0.012 | 0.08 |

TABLE 14

|  | $E_{S1}$ (eV) | $E_{T1}$ (eV) | $\Delta E_{ST}$ (eV) | Relative Value |
| --- | --- | --- | --- | --- |
| Comparative Compound 9-1 | 2.586 | 2.336 | 0.250 | 1.00 |
| Invention Compound 9-1 | 2.746 | 2.525 | 0.221 | 0.88 |
| Invention Compound 9-2 | 2.800 | 2.618 | 0.182 | 0.73 |
| Invention Compound 9-3 | 2.755 | 2.560 | 0.196 | 0.78 |
| Invention Compound 9-4 | 2.766 | 2.761 | 0.004 | 0.02 |
| Invention Compound 9-5 | 2.778 | 2.776 | 0.003 | 0.01 |

TABLE 15

|  | $E_{S1}$ (eV) | $E_{T1}$ (eV) | $\Delta E_{ST}$ (eV) | Relative Value |
| --- | --- | --- | --- | --- |
| Comparative Compound 10-1 | 2.517 | 2.236 | 0.281 | 1.00 |
| Invention Compound 10-1 | 2.534 | 2.434 | 0.100 | 0.35 |
| Invention Compound 10-2 | 2.452 | 2.375 | 0.077 | 0.27 |

As shown in these Tables, the invention compounds having a cyano group, an aryl group and a donor group had a smaller $\Delta E_{ST}$ value as compared with the corresponding comparative compounds (comparative compounds not having an aryl group Ar)

[C] Production and Evaluation of Thin Film (Example 1) Production and Evaluation of Thin Film of Invention Compound 6-1 Alone According to a vacuum evaporation method, the invention compound 6-1 was vapor-deposited on a quartz substrate under a condition of a vacuum degree of less than $1 \times 10^{-3}$ Pa to form thereon a thin film of the invention compound 6-1 alone in a thickness of 70 nm.

Figure 2:
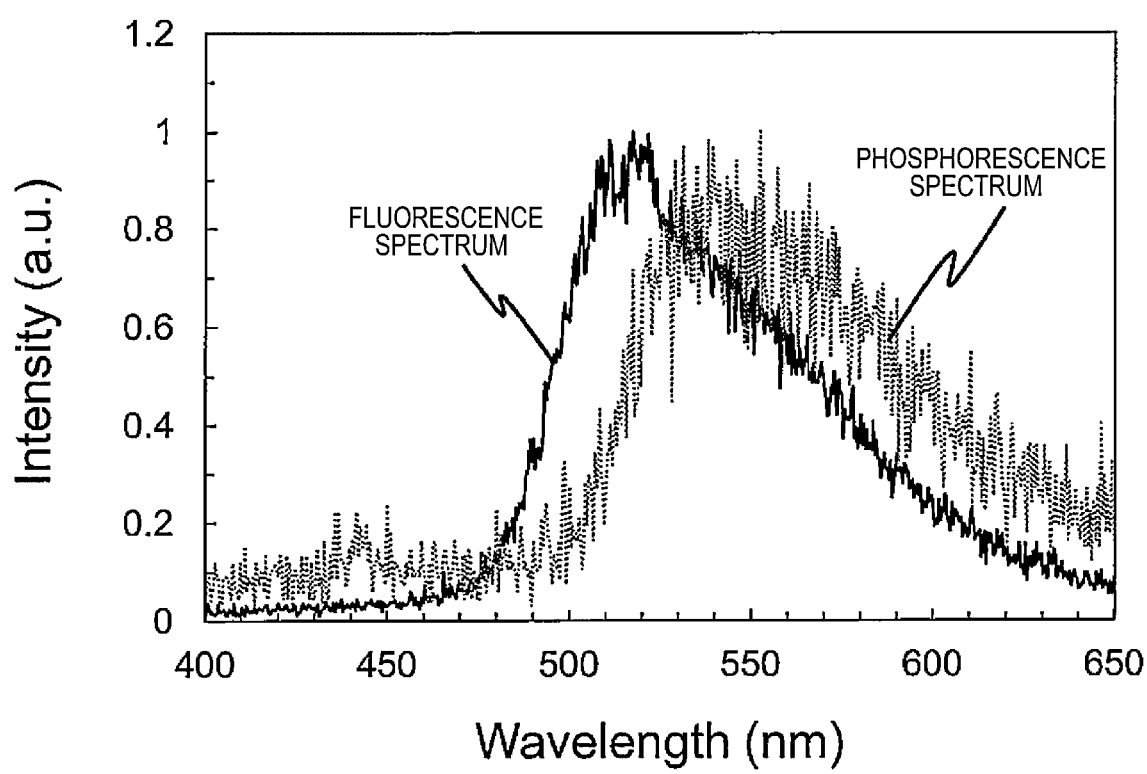
FIG. 2 This shows a fluorescence spectrum and a phosphorescence spectrum of a compound 6-1 of the invention of Example 1.
Figure 3:
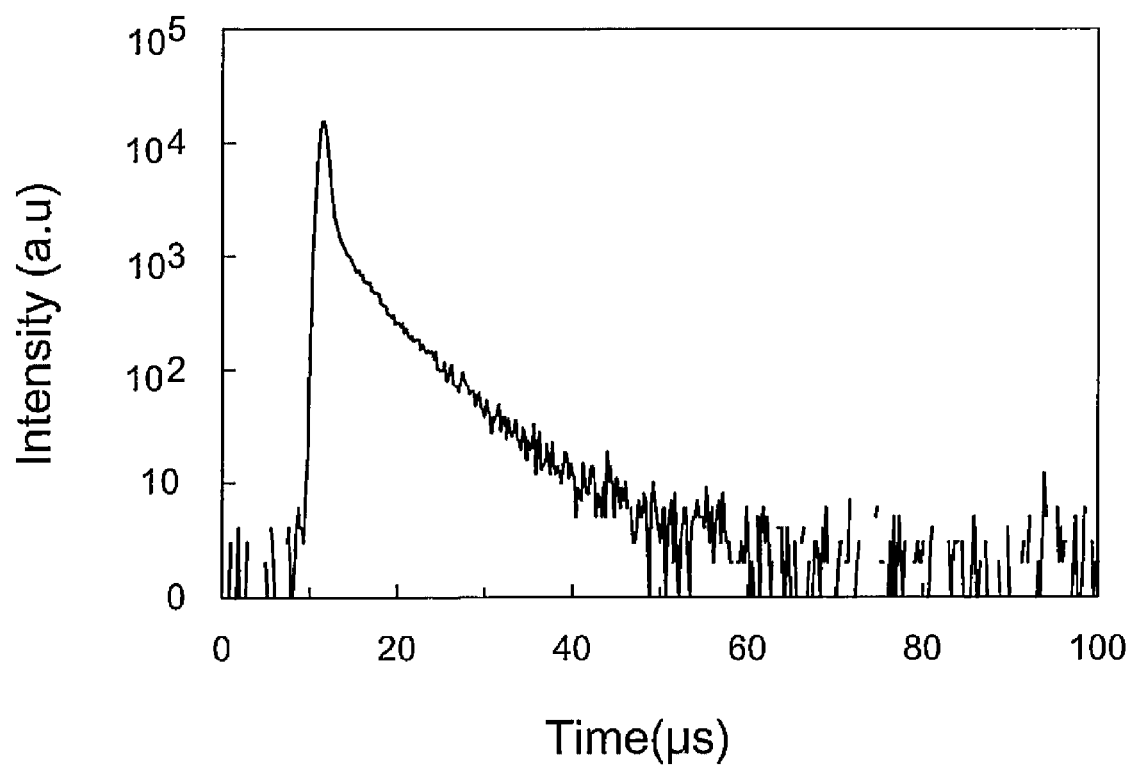
FIG. 3 This is a transient decay curve of a thin film of a compound 6-1 alone of the invention of Example 1.

Using a 337 nm excitation light, the resultant thin film was analyzed to observe the emission spectrum thereof, and the peak wavelength ($\lambda_{max}$) of the film was 530 nm. FIG. 2 shows a fluorescence spectrum and a phosphorescence spectrum of the film. FIG. 3 shows a transient decay curve in emission of the thin film observed using a 337 nm excitation light. The lifetime ($\tau_d$) of delayed fluorescence was 5.62 μs (microseconds). $\Delta E_{ST}$ was calculated and was 0.123 eV. Further, using a 300 nm excitation light, the photoluminescence quantum yield (PLQY) of the film was measured, and was 36.0% in air and 39.9% in nitrogen.

(Example 2) Production and Evaluation of Doped Thin Film with Invention Compound 6-1

According to a vacuum evaporation method, the invention compound 6-1 and mCBP were vapor-deposited from different evaporation sources on a quartz substrate under a condition of a vacuum degree of less than 1×10⁻³ Pa to form thereon a thin film having a thickness of 100 nm and having a concentration of the invention compound 6-1 of 20% by weight.

Figure 4:
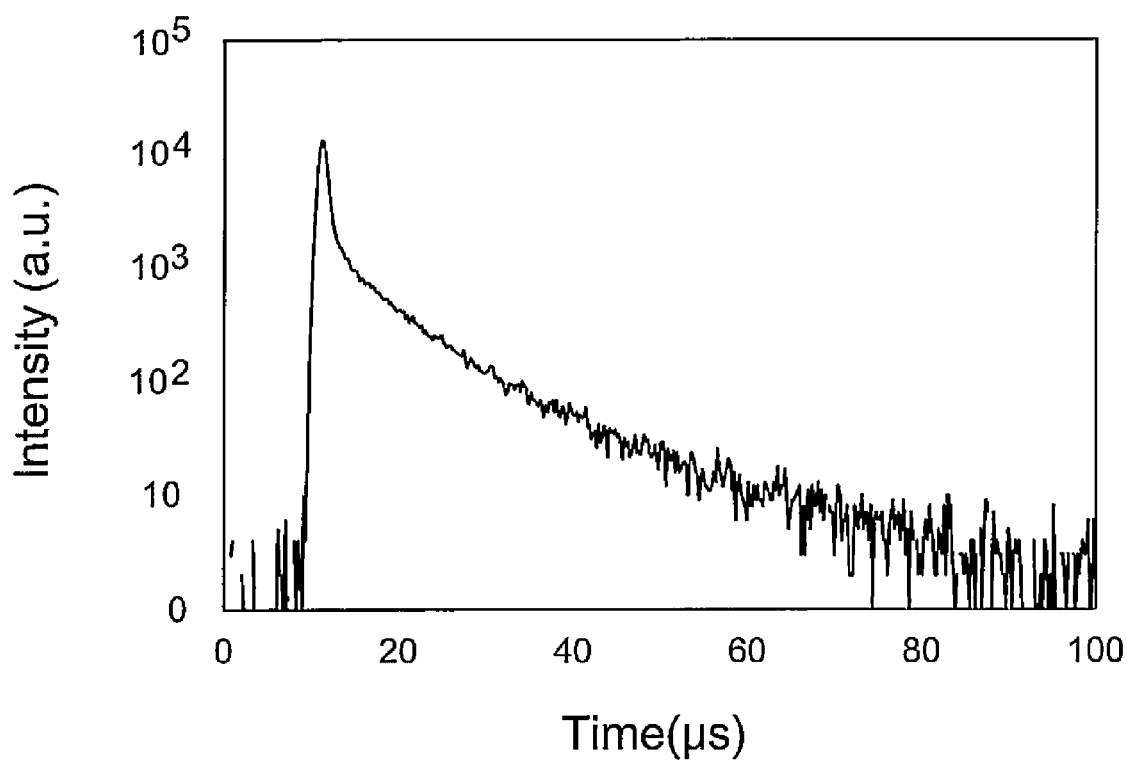
FIG. 4 This is a transient decay curve of a doped thin film with a compound 6-1 of the invention of Example 2.

Using a 337 nm excitation light, the resultant thin film was analyzed to observe the emission spectrum thereof, and the peak wavelength ($\lambda_{max}$) of the film was 518 nm. FIG. 4 shows a transient decay curve in emission of the thin film observed using a 337 nm excitation light. The lifetime ($\tau_d$) of delayed fluorescence was 9.16 μs (microseconds). Further, using a 300 nm excitation light, the photoluminescence quantum yield (PLQY) of the film was measured, and was 65.7% in nitrogen.

(Comparative Example 1) Production and Evaluation of Thin Film of Comparative Compound 6-1 Alone In the same manner as in Example 1 except that the comparative compound 6-1 was used in place of the invention compound 6-1, a thin film of the comparative compound 6-1 alone was formed in a thickness of 70 nm.

$\Delta E_{ST}$ of the resultant thin film was measured and was 0.213 eV.

(Comparative Example 2) Production and Evaluation of Doped Thin Film with Comparative Compound 6-1

In the same manner as in Example 2 except that the comparative compound 6-1 was used in place of the invention compound 6-1, a thin film having a thickness of 100 nm and having a concentration of the comparative compound 6-1 of 20% by weight was formed.

Figure 5:
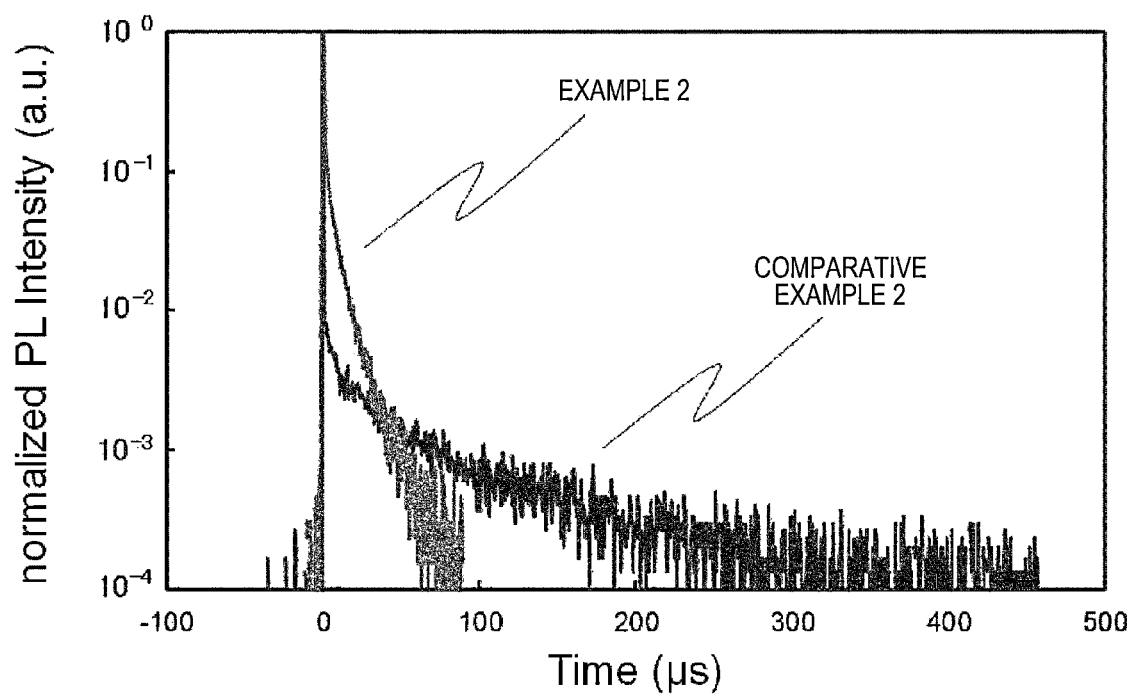
FIG. 5 This is a transient decay curve of a doped thin film with a comparative compound 6-1 of Comparative Example 2.

FIG. 5 shows a transient decay curve in emission of the resultant thin film observed using a 337 nm excitation light. In addition, the transient decay curve in emission in Example 4 shown in FIG. 4 is additionally shown in FIG. 5 by changing the scale of the horizontal axis and the vertical axis. The lifetime ($\tau_d$) of delayed fluorescence of the thin film of Comparative Example 2 was 76.8 μs (microseconds).

The measured results of Example 1 and Comparative Example 1 are compared. $\Delta E_{ST}$ of the thin film of the invention compound 6-1 produced in Example 1 was about 0.58 times $\Delta E_{ST}$ of the thin film of the comparative compound 6-1 produced in Comparative Example 1. The computational results in Table 11 are referred to. $\Delta E_{ST}$ of the invention compound 6-1 is about 0.43 times $\Delta E_{ST}$ of the thin film of the comparative compound 6-1. From these, it is confirmed that the computational results of $\Delta E_{ST}$ well correspond to the tendency of the measured value thereof. The lifetime (td) of delayed fluorescence of the thin film of Example 2 is about 0.12 times the lifetime ($\tau_d$) of delayed fluorescence of the thin film of Comparative Example 2, that is, ta of the invention compound 6-1 is far shorter than ta of the comparative compound 6-1. This is because the invention compound 6-1 has a small value of $\Delta E_{ST}$ and therefore can readily undergo reverse intersystem crossing from the excited triplet state to the excited singlet state.

The above-mentioned measurement results and computational results show that the invention compounds employed in these Examples all have a smaller value $\Delta E_{ST}$ than the corresponding comparative compounds, and accordingly, it is known that the invention compounds can readily undergo reverse intersystem crossing, that is, the invention compounds have a short delayed fluorescence lifetime. The electroluminescent devices using such a compound that has a short emission lifetime are relieved from emission efficiency reduction owing to accumulation of excitons in a high-current density region and from degradation of devices in long-term driving, and therefore exhibit excellent device performance. From these results, it is known that the compound represented by the general formula (1) can significantly contribute toward realization of such excellent light-emitting devices.

What is claimed is:

1. A compound represented by the following general formula (1):

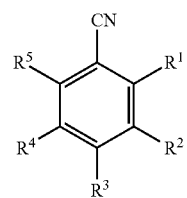

General Formula (1)

wherein R² is a cyano group,

R¹ alone or alternatively each of R¹ and R⁴ is independently an aryl group Ar optionally substituted with an alkyl group or an aryl group in which the aryl group Ar has a benzene ring that may be condensed with a ring that may optionally contain an oxygen atom or a sulfur atom in addition to carbon atoms as a ring skeleton-constituting atom, but is not condensed with a ring containing any other hetero atom than an oxygen atom and a sulfur atom as a ring skeleton-constituting atom, the total carbon number of the Ar is 6 to 30, and when R¹ and R⁴ are Ar's, these Ar's may be the same as or different from each other, each of R³ and R⁵ or alternatively each of R³, R⁴ and R⁵ is a donor group D except when one corresponds to Ar, and the two or three D's may be the same as or different from each other, D is represented by the following formula (5):

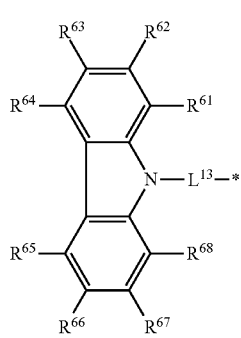

General Formula (5)

wherein $R^{61}$ to $R^{68}$ each independently represent a hydrogen atom or a substituent; $L^{13}$ represents a single bond; $R^{61}$ and $R^{62}$, $R^{62}$ and $R^{63}$, $R^{63}$ and $R^{64}$, $R^{65}$ and $R^{66}$, $R^{66}$ and $R^{67}$, $R^{67}$ and $R^{68}$ each may bond to each other to form a linking group necessary for forming a cyclic structure; and * indicates a bonding position to a carbon atom (C) constituting the ring skeleton of the benzene ring in the general formula (1).

2. The compound according to claim 1, wherein only $R^1$ is Ar.

3. The compound according to claim 1, wherein $R^1$ and $R^4$ are Ar.

* * * * *